(12) United States Patent
Hamilton et al.

(10) Patent No.: US 11,124,479 B2
(45) Date of Patent: Sep. 21, 2021

(54) OLIGOPYRROLES AS ANTAGONISTS OF ISLET AMYLOID POLYPEPTIDE OLIGOMERIZATION

(71) Applicant: New York University, New York, NY (US)

(72) Inventors: Andrew D. Hamilton, New York, NY (US); Sunil Kumar, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 16/035,131

(22) Filed: Jul. 13, 2018

(65) Prior Publication Data

US 2019/0016679 A1 Jan. 17, 2019

Related U.S. Application Data

(60) Provisional application No. 62/532,618, filed on Jul. 14, 2017.

(51) Int. Cl.

| | | |
|---|---|---|
| *A61K 31/4025* | (2006.01) | |
| *C07D 403/14* | (2006.01) | |
| *C07D 207/42* | (2006.01) | |
| *A61P 1/18* | (2006.01) | |
| *A61P 5/48* | (2006.01) | |
| *A61P 5/50* | (2006.01) | |
| *A61P 3/10* | (2006.01) | |
| *A61P 25/28* | (2006.01) | |
| *A61P 25/16* | (2006.01) | |

(52) U.S. Cl.
CPC .................. *C07D 207/42* (2013.01)

(58) Field of Classification Search
CPC .............. A61K 31/4025; C07D 403/14; C07D 207/42; A61P 1/18; A61P 5/48; A61P 5/50; A61P 3/10; A61P 25/28; A61P 25/16
USPC .......................... 514/422; 548/523, 524, 537
See application file for complete search history.

(56) References Cited

U.S. PATENT DOCUMENTS

| | | |
|---|---|---|
| 4,476,116 A | 10/1984 | Anik |
| 4,511,069 A | 4/1985 | Kalat |
| 4,778,810 A | 10/1988 | Wenig et al. |
| 5,203,840 A | 4/1993 | Graf et al. |
| 5,759,565 A | 6/1998 | Azria et al. |
| 5,860,567 A | 1/1999 | Fuchs et al. |
| 5,893,484 A | 4/1999 | Fuchs et al. |
| 6,090,947 A | 7/2000 | Dervan et al. |
| 6,227,415 B1 | 5/2001 | Ritsche et al. |
| 6,364,166 B1 | 4/2002 | Ritsche et al. |
| 6,514,496 B1 | 2/2003 | Platz et al. |
| 6,559,125 B1 | 5/2003 | Dervan et al. |
| 7,087,378 B1 | 8/2006 | Baird et al. |

FOREIGN PATENT DOCUMENTS

| | | | |
|---|---|---|---|
| EP | 0037943 A2 | 10/1981 | |
| EP | 0094157 A1 | 11/1983 | |
| EP | 0173990 A2 | 3/1986 | |
| EP | 0214898 A2 | 3/1987 | |
| EP | 0215697 A2 | 3/1987 | |
| EP | 0327756 A2 | 8/1989 | |
| EP | 0490806 A2 | 6/1992 | |
| WO | WO-03059881 A2 * | 7/2003 | ........... C07D 417/14 |
| WO | 2004093917 A2 | 11/2004 | |
| WO | 2005120551 A1 | 12/2005 | |

OTHER PUBLICATIONS

Meng, F. and D. Raleigh, "Inhibition of Glycosaminoglycan-Mediated Amyloid Formation by Islet Amyloid Polypeptide and proIAPP processing Intermediates" Journ. Mol. Biol. (2011), pp. 491-502. (Year: 2011).*
Grokhovsky, S., V. Nikolaev, B. Gottikh and A. Zhuze, "DNA sequence-specific Ligands: XI. The synthesis and binding to DNA of bis-Netropsins with the C-Ends of their Netropsin Fragments tethered by tetra- or Pentamethylene linkers" Russ. J. Bioorg. Chem. (2002), 28 (6), pp. 455-469. (Year: 2002).*
STN Registry database entry: CAS RN 185614-27-1 (Entered STN: Jan. 30, 1997) (Year: 1997).*
Turchin, K.F. et al., "Ligands with an affinity to certain pairs of DNA bases", Bioorg. Chem., 4 (8), 1978, pp. 1065-1077. (Year: 1978).*
Translation of Turchin, K.F. et al., "Ligands with an affinity to certain pairs of DNA bases", Bioorg. Chem., 4 (8), 1978, pp. 1065-1077. (Year: 2020).*
Abedini, A. et al., "Mechanisms of Islet Amyloidosis Toxicity in Type 2 Diabetes" FEBS Lett. (2013) vol. 587, No. 8, pp. 1119-1127.
Abedini, A. et al., "Time-Resolved Studies Define the Nature of Toxic IAPP Intermediates, Providing Insight for Anti-Amyloidosis Therapeutics" eLife (2016) vol. 5, No. e12977, 28 pages total.
Andreetto, E. et al., "Identification of Hot Regions of the Aβ—IAPP Interaction Interface as High-Affinity Binding Sites in both Cross- and Self-Association" Angewandte Chemie Int. Ed. (2010) vol. 49, No. 17, pp. 3081-3085.
Ashcroft, F.M. et al., "Diabetes Mellitus and the β-Cell: the Last Ten Years" Cell (2012) vol. 148, No. 6, pp. 1160-1171.
Cao, P. et al., "Analysis of the Inhibition and Remodeling of Islet Amyloid Polypeptide Amyloid Fibers by Flavanols" Biochemistry (2012) vol. 51, No. 13, pp. 2670-2683.

(Continued)

*Primary Examiner* — Joseph R Kosack
*Assistant Examiner* — Sagar Patel
(74) *Attorney, Agent, or Firm* — Troutman Pepper Hamilton Sanders LLP

(57) ABSTRACT

The invention relates to compounds and pharmaceutical compositions capable of treating amyloid diseases and other diseases characterized by oligomerization and/or fibrillation of amyloidogenic peptides such as islet amyloid polypeptide (IAPP).

16 Claims, 17 Drawing Sheets

(17 of 17 Drawing Sheet(s) Filed in Color)

(56) References Cited

OTHER PUBLICATIONS

Cao, P. et al., "Islet Amyloid Polypeptide Toxicity and Membrane Interactions" Proc. Natl. Acad. Sci. U.S.A. (2013) vol. 110, No. 48, pp. 19279-19284.
Chen, P.S. et al., "Microdetermination of Phosphorus" Angewandte Chemie (1956) vol. 28, No. 11, pp. 1756-1758.
Chenoweth, D.M. et al., "Py-Im Polyamides Distinguish Double Helical DNA and RNA" Angew. Chem. Intl. Ed. (2013) vol. 52, No. 1, pp. 415-418.
Chiti, F. et al., "Protein Misfolding, Functional Amyloid, and Human Disease" Annual Review of Biochemistry (2006) vol. 75, pp. 333-366.
Chiti, F. et al., "Amyloid Formation by Globular Proteins Under Native Conditions" Nature Chemical Biology (2009) vol. 5, pp. 15-22.
Daval, M. et al., "The Effect of Curcumin on Human Islet Amyloid Polypeptide Misfolding and Toxicity" Amyloid (2010) vol. 17, No. 0, pp. 118-128.
Davis, S.S. et al., "Absorption Enhancers for Nasal Drug Delivery" Clinical Pharmacokinetics (2003) vol. 42, Issue 13, pp. 1107-1128.
Feng, B.Y. et al., "Small-Molecule Aggregates Inhibit Amyloid Polymerization" Nature Chem Biol (2008) vol. 4, No. 3, pp. 197-199.
Garcia-Arieta, A. et al., "Spray-Dried Powders as Nasal Absorption Enhancers of Cyanocobalamin" Biol. Pharm. Bull. (2001) vol. 24, No. 12, pp. 1411-1416.
Hao, M. et al., "Vesicular and Non-Vesicular Sterol Transport in Living Cells" Journal of Biological Chemistry (2002) vol. 277, No. 1, pp. 609-617.
Hardy, J. et al., "Alzheimer's Disease: The Amyloid Cascade Hypothesis" Science (1992) vol. 256, Issue 5054, pp. 184-185.
Hardy, J. et al., "The Amyloid Hypothesis of Alzheimer's Disease: Progress and Problems on the Road to Therapeutics" Science (2002) vol. 297, No. 5580, pp. 353-356.
Hebda, J.A. et al., "A Peptidomimetic Approach to Targeting Pre-Amyloidogenic States in Type II Diabetes" Chem. Biol. (2009) vol. 16, No. 9, pp. 943-950.
Huang, C.-J. et al., "High Expression Rates of Human Islet Amyloid Plolypeptide Induce Endoplasmic Reticulum Stress-Mediated β-Cell Apoptosis, a Characteristic of Human with Type 2 but not Type 1 Diabetes" Diabetes (2007) vol. 56, pp. 2016-2027.
Jahn, T.R. et al., "The Common Architecture of Cross-β Amyloid" Journal of Molecular Biology (2010) vol. 395, Issue 4, pp. 717-727.
Kayed, R. et al., "Common Structure of Soluble Amyloid Oligomers Implies Common Mechanism of Pathogenesis" C.G. Science (2003) vol. 300, pp. 486-489.
Knight, J.D. et al., "Conserved and Cooperative Assembly of Membrane-Bound α-Helical States of Islet Amyloid Polypeptide" Biochemistry (2006) vol. 45, No. 31, pp. 9496-9508.
Kulikov, O.V. et al., "Amphiphilic Oligoamide α-Helix Peptidomimetics Inhibit Islet Amyloid Polypeptide Aggregation" Tetrahedron Letters (2015) vol. 56, Issue 23, pp. 3670-3673.
Kumar, S. et al., "A Foldamer Approach to Targeting Membrane Bound Helical States of Islet Amyloid Polypeptide" Chem. Commun. (2013) vol. 49, No. 42, pp. 4749-4751.
Kumar, S. et al., "Foldamer Scaffolds Suggest Distinct Structures are Associated with Alternative Gains-of-Function in a Preamyloid Toxin" Chem. Commun. (2016) vol. 52, No. 38, pp. 6391-6394.
Kumar, S. et al., "Foldamer-Mediated Manipulation of a Preamyloid Toxin" Nature Communications (2016) vol. 7, No. 11412, pp. 1-11.
Kumar, S. et al., "Folded Small Molecule Manipulation of Islet Amyloid Polypeptide" Chem. Biol. (2014) vol. 21, No. 6, pp. 775-781.
Kumar, S. et al., "Islet Amyloid Induced Cell Death and Bilayer Integrity loss Share a Molecular Origin Targetable with Oligopyridylamide-Based α-Helical Mimetics" Chem. Biol. (2015) vol. 22, No. 3, pp. 369-378.
Last, N.B. et al., "Common Mechanism United Membrane Poration by Amyloid and Antimicrobial Peptides" Proc. Natl. Acad. Sci. U.S.A. (2013) vol. 110, No. 16, pp. 6382-6387.
Last, N.B. et al., "Islet Amyloid Polypeptide Demonstrates a Persistent Capacity to Disrupt Membrane Integrity" Proc. Natl. Acad. Sci. U.S.A. (2011) vol. 108, No. 23, pp. 9460-9465.
Levine, H., "Thioflavine T Interaction with Synthetic Alzheimer's Disease β-Amyloid Peptides: Detection of Amyloid Aggregation in Solution" (1993) vol. 2, pp. 404-410.
Magzoub, M. et al., "Concentration-Dependent Transitions Govern the Subcellular Localization of Islet Amyloid Polypeptide" FASEB Journal (2012) vol. 26, No. 3, pp. 1228-1238.
Meng, F. et al., "The Flavanol (−)-Epigallocatechin 3-Gallate Inhibits Amyloid Formation by Islet Amyloid Polypeptide, Disaffrefates Amyolid Fibrils and Protects Cultured Cells Against AIPP Induced Toxicity" Biochemistry (2010) vol. 49, No. 37, pp. 8127-8133.
Meng, F. et al., "The Sulfated Triphenyl Methane Derivative Acid Fuchsin is a Potent Inhibitor of Amyloid Formation by Human Islet Amyloid Polypeptide and Protects Against the Toxic Effects of Amyloid Formation" Journal of Molecular Biology (2010) vol. 400, No. 3, pp. 555-566.
Mrksich, M.E. et al., "Hairpin Peptide-Turn-Peptide Motif. A New Class of Hexapeptides for Sequence-Specific Recognition in the Minor Groove of DNA" J. Am. Chem. Soc. (1994) vol. 116, pp. 7983-7988.
O'Hagan, DT et al., "Nasal Absorption Enhancers for Biosynthetic Human Growth Hormone in Rats" Pharm. Res. (1990) vol. 7, No. 7, pp. 772-776.
Ono, K. et al., "Structure-Neurotoxicity Relationships of Amyloid β-Protein Oligomers" Proc. Natl. Acad. Sci. U.S.A. (2009) vol. 106, No. 35, pp. 14745-14750.
Peacock, H. et al., "Non-Covalent S—O Interactions Control Conformation in a Scaffold that Disrupts Islet Amyloid Polypeptide Fibrillation" Chemical Science (2016) vol. 7, pp. 6435-6439.
Pilch, D.S. et al., "Binding of a Hairpin Polyamide in the Minor Groove of DNA: Sequence-Specific Enthalpic Discrimination" Proc. Natl. Acad. Sci. U.S.A. (1996) vol. 93, pp. 8306-8311.
Pithadia, A. et al., "Inhibition of IAPP Aggregation and Toxicity by Natural Products and Derivatives" Journal of Diabetes Research (2016) vol. 2016, 1-12 pages total.
Rustenbeck, I. et al., "Lipid Composition of Glucose-Stimulated Pancreatic Islets and Insulin-Secreting Tumor Cells" Lipids (1994) vol. 10, pp. 685-692.
Saraogi, I. et al., "Synthetic α-Helix Mimetics as Agonists and Antagonists of IAPP Amyloid Formation" Angew. Chem. Intl. Ed. (2010) vol. 49, No. 4, pp. 736-739.
Sciacca, M.F.M. et al., "The Role of Cholesterol in Driving IAPP-Membrane Interactions" Biophysical Journal (2016) vol. 111, pp. 140-151.
Sparks, S. et al., "Curcumin Modulates the Self-Assembly of the Islet Amyloid Polypeptide Disassembling α-Helix" Biochemical and biophysical Research Communications (2012) vol. 422, Issue 4, pp. 551-555.
Uytterhoeven, K. et al., "Two 1:1 Binding Modes for Distamycin in the Minor Groove of d(GGCCAATTGG)" Eur. J. Biochem. (2002) vol. 269, pp. 2868-2877.
Wade, W. et al., "Design of Peptides That Bind in the Minor Groove of DNA at 5'-(A,T)G(A,T)C(A,T)-3' Sequences by a Dimeric Side-by-Side Motif" J. Am. Chem. Soc. (1992) vol. 114, pp. 8783-8794.
Warnock, D.E. et al., "Determination of Plasma Membrane Lipid Mass and Composition in Cultured Chinese Hamster Ovary Cells Using High Gradient Magnetic Affinity Chromatography" Journal of Biological Chemistry (1993) vol. 268, pp. 10145-10153.
Westermark, P. et al., "Islet Amyloid Polypeptide, Islet Amyloid, and Diabetes Mellitus" Physiol. Rev. (2011) vol. 91, pp. 795-826.
Wolfe, L.S. et al., "Protein-Induced Photophysical Changes to the Amyloid Indicator Dye Thioflavin T" Proc. Natl. Acad. Sci. U.S.A. (2010) vol. 107, No. 39, pp. 16863-16868.
Yan, K.-M. et al., "IAPP Mimic Blocks Aβ and IAPP Suggests a Molecular Link Between Alzheimer's Disease and Type II Diabetes" Angewandte Chemie Int. Ed. (2007) vol. 46, No. 8, pp. 1246-1252.

(56) References Cited

OTHER PUBLICATIONS

Yan, L.-M. et al., "Design of a Mimic of Nonamyloidogenic and Bioactive Human Islet Amyloid Polypeptide (IAPP) as Nanomolar Affinity Inhibitor of IAPP Cytotoxic Fibrillogenesis" Proc. Natl. Acad. Sci. U.S.A. (2006) vol. 103, No. 7, pp. 2046-2051.

* cited by examiner

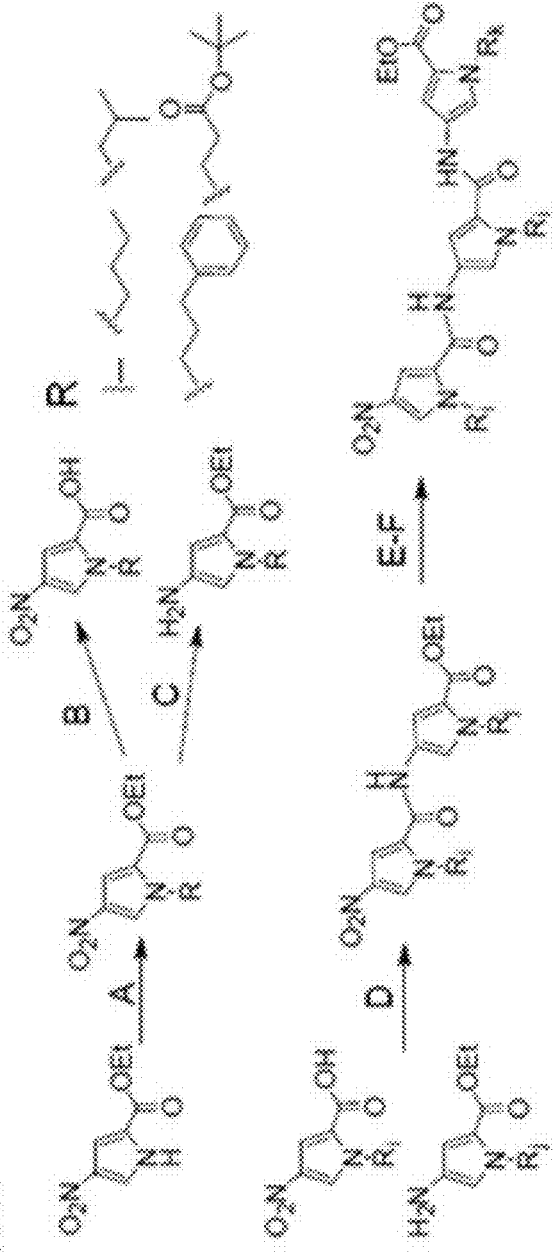
FIG. 1A
FIG. 1B
KCNTATCATQ
RLANFLVHSS
NNFGAILSSTN
VGSNTY-NH$_2$
IAPP
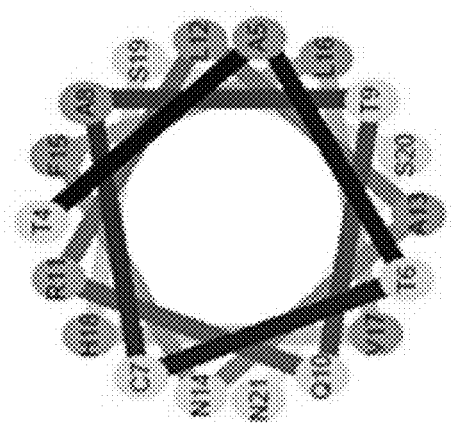
FIG. 1C

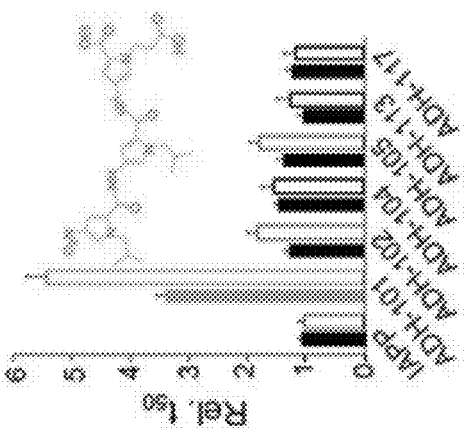
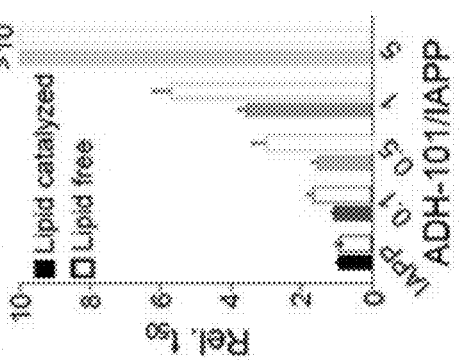
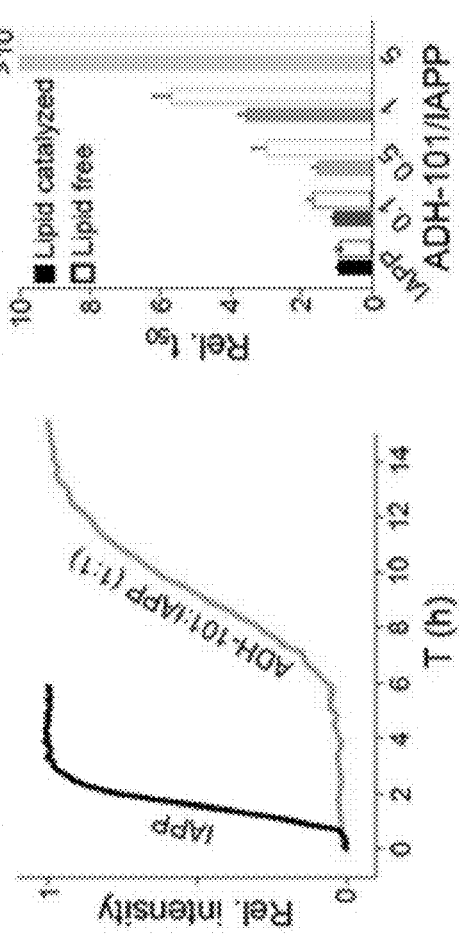
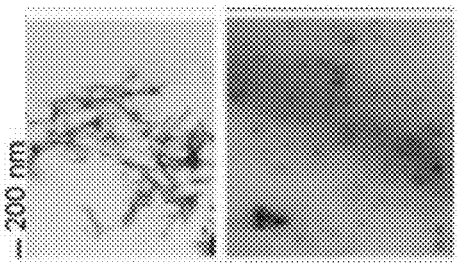
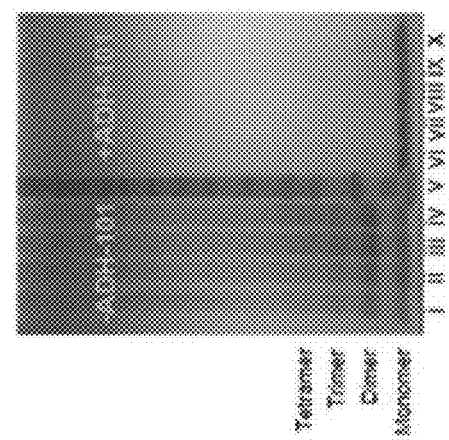
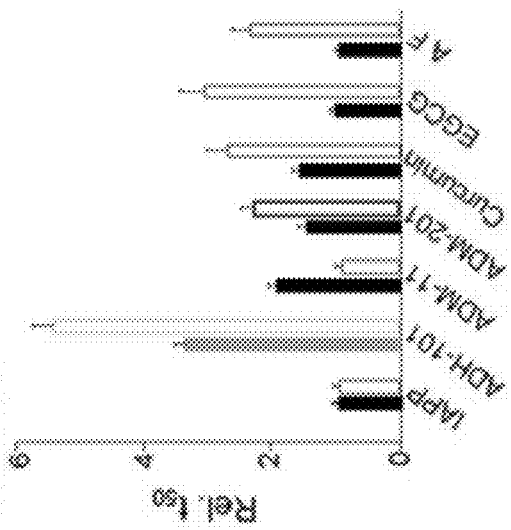

OLIGOPYRROLES AS ANTAGONISTS OF ISLET AMYLOID POLYPEPTIDE OLIGOMERIZATION

CROSS-REFERENCE TO RELATED APPLICATIONS

This application claims priority to U.S. Provisional Patent Application No. 62/532,618, filed on Jul. 14, 2017, the contents of which are herein incorporated by reference in its entirety.

FIELD OF THE INVENTION

The present invention relates to compounds and pharmaceutical compositions capable of treating diseases associated with oligomerization and/or fibrillation of amyloidogenic peptides such as Islet Amyloid Polypeptide (IAPP).

BACKGROUND

The pathophysiological aggregation of proteins is associated with more than 40 clinical conditions, including neurodegenerative and organ localized diseases (Chiti, F.; Dobson, C. M. *Annu. Rev. Biochem.* 2006, 75, 333-366). Most of these disorders share a common theme, where the soluble functional protein proceeds via a series of conformational switches and eventually terminates into insoluble amyloid fibers rich in β-sheet structures (Chiti, F.; Dobson, C. M. *Nat. Chem. Biol.* 2009, 5, 15-22; Jahn, T. R.; Makin, O. S.; Morris, K. L.; Marshall, K. E.; Tian, P.; Sikorski, P.; Serpell, L. C. *J. Mol. Biol.* 2010, 395, 717-727; Kayed, R.; Head, E.; Thompson, J. L.; McIntire, T. M.; Milton, S. C.; Cotman, C. W.; Glabe, C. G. *Science* 2003, 300, 486).

Islet amyloid polypeptide (IAPP) is one such peptide, which is associated with the pathology of diabetes mellitus, specifically diabetes mellitus type 2 (DM2). IAPP is a 37 residue neuropancreatic hormone peptide, co-secreted from β-cells within the islets of Langerhans in the pancreas (Westermark, P.; Andersson, A.; Westermark, G. T. *Physiol. Rev.* 2011, 91, 795). The loss of β-cell mass in islets containing IAPP amyloid deposits suggests a potential role of IAPP in the etiology of DM2 (Ashcroft, F.; Rorsman, P. *Cell* 2012, 148, 1160-1171).

Membrane bound helical intermediates are very important targets as these structures are sampled by many intrinsically disordered proteins such as α-synuclein in Parkinson's disease and Aβ-peptide in Alzheimer's disease. IAPP samples a series of conformations starting from random coil conformation to β-sheet structure via membrane bound α-helical intermediates. The mechanism of cytotoxicity induced by IAPP is still highly debatable; however, the prevailing view is that oligomeric intermediates are the key cytotoxic structures which gain toxic functions upon interaction with the cell membranes (Ashcroft, F.; Rorsman, P. *Cell* 2012, 148, 1160-1171; Abedini, A.; Schmidt, A. M. *FEBS Lett.* 2013, 587, 1119-1127; Cao, P.; Abedini, A.; Wang, H.; Tu, L.; Zhang, X.; Schmidt, A. M.; Raleigh, D. P. *Proc. Natl. Acad. Sci. U.S.A.* 2013, 110, 19279-19284; Knight, J. D.; Hebda, J. A.; Miranker, A. D. *Biochemistry* 2006, 45, 9496-9508; Magzoub, M.; Miranker, A. D. *FASEB J.* 2012, 26, 1228-1238; Abedini, A.; Plesner, A.; Cao, P.; Ridgway, Z.; Zhang, J.; Tu, L.; Middleton, C. T.; Chao, B.; Sartori, D. J.; Meng, F.; Wang, H.; Wong, A. G.; Zanni, M. T.; Verchere, C. B.; Raleigh, D. P.; Schmidt, A. M. *eLife* 2016, 5, e12977). It has been proposed that IAPP oligomers colocalize at the mitochondria and render β-cells dysfunctional (Magzoub, M.; Miranker, A. D. *FASEB J.* 2012, 26, 1228-1238). Regardless, the oligomers are either directly involved in the toxic insult of the β-cells, or indirectly induce protein aggregation, which is toxic to the cells. In essence, strategies that disrupt as well as stabilize the membrane bound helical intermediates would be desirable from both mechanistic and therapeutic points of view.

Numerous small molecules have been identified as antagonists of IAPP fibrillation either via deliberate design or high-throughput screening. These include foldamers, natural products, acid fuchsin, and di-substituted N-methyl derivatives of IAPP (Saraogi, I.; Hebda, J.; Becerril, J.; Estroff, L.; Miranker, A.; Hamilton, A. *Angew. Chem. Intl. Ed.* 2010, 49, 736-739; Kumar, S.; Miranker, A. D. *Chem. Commun.* 2013, 49, 4749-4751; Kumar, S.; Brown, M.; Nath, A.; Miranker, A. *Chem. Biol.* 2014, 21, 775-781; Kumar, S.; Birol, M.; Schlamadinger, D. E.; Wojcik, S. P.; Rhoades, E.; Miranker, A. D. *Nat Commun* 2016, 7, 1-11; Peacock, H.; Luo, J.; Yamashita, T.; Luccarelli, J.; Thompson, S.; Hamilton, A. D. *Chem. Sci.*, 2016, 7, 6435-6439; Pithadia A., Brender J. R., Fierke C. A., and Ramamoorthy A. *J Diabetes Res.* 2016, 1-12; Meng, F.; Abedini, A.; Plesner, A.; Middleton, C. T., Potter, K. J.; Zanni, M. T.; Verchere, C. B.; Raleigh, D. P. *J. Mol. Biol.* 2010, 400, 555-566; Yan, L.; Tatarek-Nossol, M.; Velkova, A.; Kazantzis, A.; Kapurniotu, A. *Proc. Natl. Acad. Sci. U.S.A.* 2006, 103, 2046-2051). The mode of action of these molecules varies as they target various facets of IAPP.

Foldamers, including oligopyridylamides, oligobenzamides, and oligoquinolines, have been identified as potent antagonists of membrane catalyzed IAPP fibrillation, and their antagonist activity can be enhanced significantly by careful surface modifications. The ability to manipulate foldamer design to mimic the desired protein sequence makes them an important class of molecules as potential therapeutics.

Poly-(pyrrole/imidazole) is a class of foldamers that has been known to target various nucleic acids in a sequence specific manner (Wade, W. S.; Mrksich, M.; Dervan, P. B. *J. Am. Chem. Soc.* 1992, 114, 8783-8794; Mrksich, M.; Parks, M. E.; Dervan, P. B. *J. Am. Chem. Soc.* 1994, 116, 7983-7988; see also U.S. Pat. Nos. 6,090,947; 6,559,125; 7,087, 378).

Derived from natural products distamycin and netropsin, they have been engineered by Dervan et al as a means to target various sequences of DNA. The scaffolds utilize pyrrole and imidazole to develop 'pairing rules' to target a broad range of DNA sequences with high affinity and specificity. To achieve DNA sequence specificity, the modifications were employed either at the backbone or at the scaffold (imidazole or pyrrole). However, no effort has been directed to modifying the exterior functionalities on the convex surface. Furthermore, no attempt to develop functionalized oligopyrroles to mimic protein fold has been reported.

Polyamides adjust their topology to a convex shape to complement the topology of the minor groove of DNA. The distance between the nitrogen atom of the first pyrrole and third pyrrole of DNA-bound distamycin is ~12.7 Å, which is within the vicinity of the distance between the first carbon and the third carbon of the side chain functionalities of a tripyridylamide (~11.2 Å) (Uytterhoeven, K.; Sponer, J.; Van Meervelt, L. *Eur. J. Biochem.* 2002, 269, 2868-2877). The surface functionalities of tripyridylamides are spatially oriented in a well-defined arrangement to mimic the side chain residues of one helical surface at positions i, i+3/i+4, and i+7, and in the way act as antagonists of the membrane-bound α-helical intermediates of IAPP.

Previously, certain oligopyridylamide-based α-helical mimetics have been used to target the membrane-associated α-helical conformation of IAPP and were found to be strong antagonists of membrane-catalyzed IAPP aggregation. Structure-activity relationship studies were conducted to optimize the inhibitory activity against IAPP self-assembly via charge complementarity and hydrophobic interactions. In addition to the solution biophysical assays, the α-helical mimetics were very effective in rescuing an insulin secreting cell line from IAPP-mediated cytotoxicity.

As discussed above, several disease-specific amyloidogenic proteins share similar structural and functional properties. These proteins proceed through a series of conformation switches starting from the native disordered state to soluble oligomeric intermediates which eventually terminate into highly ordered intractable fiber aggregates. An increasing body of evidence suggests that soluble oligomers are the predominant cytotoxic species associated with various amyloid-related diseases. Therefore, elucidation of the structural details of these oligomeric intermediates is essential for mechanistic and therapeutic purposes. Enormous efforts have been directed to identify and characterize these oligomers with limited success because of their complex and dynamic nature.

Protein misfolding is associated with the onset of many neurogenerative and organ-localized conditions. The continuous increase in the number of patients suffering from these diseases creates a social and economic burden on the modern society. For some of these diseases there are methods to alleviate the symptoms but not the cause. Therefore, there is a pressing need for drug like ligands for the prevention/cure of the above mentioned diseases.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

As specified above, there is a great need in the art to treat diseases and conditions associated with oligomerization and/or fibrillation of an amyloidogenic peptide. The present invention addresses these and other needs by providing new compounds, pharmaceutical compositions, and methods of treatment based on such compounds and pharmaceutical compositions. The compounds of the invention are useful for altering structures of one or more amyloidogenic peptides including, without limitation, AP, islet amyloid polypeptide (IAPP), α-synuclein, AA amyloid, PrP, β$_2$-microglobulin amyloid, transthyretin, prealbumin, and procalcitonin. Some of the compounds of the invention are useful for altering the structure of IAPP, and may be useful for treating diseases and disorders associated with IAPP oligomerization and/or fibrillation, such as diabetes mellitus type 2.

Various non-limiting embodiments of the invention are described below.

In one implementation, the compounds of the invention (e.g., the modulators of oligomerization of amyloidogenic peptides, such as IAPP) have the structure of formula (I):

In one embodiment, the compounds of the invention (e.g., the modulators of oligomerization of amyloidogenic peptides, such as AP and/or IAPP) have the structure of formula (I):

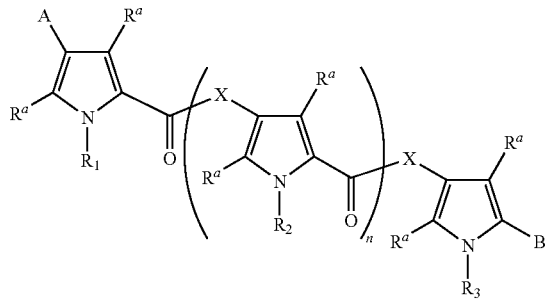

(I)

and pharmaceutically acceptable salts thereof.

In formula (I), $R^a$ is independently selected at each occurrence from hydrogen, $C_1$-$C_{12}$ hydrocarbons, —F; —Cl; —Br; —I; —OH, —OR*; —SO$_3$H; —NO; —NO$_2$; —NO$_3$; —O—NO; —N$_3$; —NH$_2$; —NHR*; and —N(R*)$_2$;

In some embodiments, $R^a$ is present at 0, 1, or 2 different positions on the ring.

In some embodiments, $R^a$ is hydrogen at all occurrences.

X is independently at each occurrence selected from —O—; —S—; —NH—; —NR*—; and —C(R*)$_2$.

In some embodiments X is —NH— or —NR*—, such that —(C=O)—X— is an amide bond, at all occurrences. In some embodiments X is NH—.

In some embodiments X is not —O—. In some embodiments X is not —S—. In some embodiments X is not C(R*)$_2$.

$R_1$, $R_2$, and/or $R_3$ are independently at each occurrence selected from hydrogen or a straight chained, branched or cyclic aliphatic $C_2$-$C_{20}$ hydrocarbon; an aromatic $C_6$-$C_{20}$ hydrocarbon; a heteroaromatic $C_2$-$C_{20}$ hydrocarbon; an aryl $C_6$-$C_{20}$ hydrocarbon; a heteroaryl $C_2$-$C_{20}$ hydrocarbon, a $C_2$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_3$H; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof.

In some embodiments $R_1$, $R_2$, and/or $R_3$ are independently at each occurrence selected from a straight chained, branched or cyclic aliphatic $C_2$-$C_{20}$ hydrocarbon; an aromatic $C_6$-$C_{20}$ hydrocarbon; a heteroaromatic $C_2$-$C_{20}$ hydrocarbon; an aryl $C_6$-$C_{20}$ hydrocarbon; a heteroaryl $C_2$-$C_{20}$ hydrocarbon, a $C_2$-$C_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3^+$; —(C=O)—R*; —CHO; —CO$_2$H; —CO$_2$R*; —(C=O)—S—R*; —O—(C=O)—H; —O—(C=O)—R*; and combinations thereof.

In some embodiments $R_1$, $R_2$, and/or $R_3$ are independently at each occurrence a straight chained, branched or cyclic aliphatic $C_2$-$C_{20}$ hydrocarbon, optionally substituted with one or more of —$NH_2$; —NHR*; —N(R*)$_2$; —N(R*)$_3^+$; —(C=O)—R*; —$CO_2H$; or —$CO_2R$*; and combinations thereof.

In some embodiments $R_1$, $R_2$, and/or $R_3$ are independently at each occurrence a straight chained, branched or cyclic $C_2$-$C_{20}$ hydrocarbon, optionally substituted with one or more of —$NH_2$; —NHR*; —N(R*)$_2$.

In some embodiments $R_1$, $R_2$, and/or $R_3$ are independently at each occurrence a straight chained, branched or cyclic aliphatic $C_2$-$C_{20}$ hydrocarbon, optionally substituted with —$CO_2H$. In some embodiments $R_1$, $R_2$, and/or $R_3$ may independently at each occurrence be —$CH_2CO_2H$.

In some embodiments $R_1$, $R_2$, and/or $R_3$ at all occurrences do not contain —$CO_2H$. In some embodiments $R_1$, $R_2$, and/or $R_3$ are not —$CH_2CO_2H$ at all occurrences.

In some embodiments $R_1$, $R_2$, and/or $R_3$ are independently at each occurrence selected from an aromatic $C_6$-$C_{20}$ hydrocarbon; a heteroaromatic $C_2$-$C_{20}$ hydrocarbon; an aryl $C_6$-$C_{20}$ hydrocarbon; or a heteroaryl $C_2$-$C_{20}$ hydrocarbon optionally containing 1-8 heteroatoms selected from halogen, O, N, and S, and each of which is optionally substituted with one or more of —$NH_2$; —NHR*; —N(R*)$_2$; —N(R*)$_3^+$; —(C=O)—R*; —CHO; —$CO_2H$; —$CO_2R$*; —(C=O)—S—R*; —O—(C=O)—H; —O—(C=O)—R*.

In some embodiments, $R_1$, $R_2$, and/or $R_3$ are independently at each occurrence selected from a substituted or unsubstituted phenyl, benzyl, naphthyl, indolyl, pyrrolidinyl, pyrrolyl, imidazolyl, pyrazolyl, oxazolyl, isoxazolyl, thiazolyl, isothiazolyl, histidinyl (i.e., —$CH_2$-imidazole), triazolyl, pyridyl, pyranyl, diazinyl, oxazinyl, thiazinyl, or triazinyl.

A is selected from —OH, —OR*; —NO; —$NO_2$; —$NO_3$; —O—NO; —$N_3$; NHR*, N(R*)$_2$; —N(R*)—OH; —O—N(R*)$_2$; —N(R*)—O—R*; —CN; —NC; —(C=O)—R*; —CHO; —$CO_2H$; —$CO_2R$*; —(C=O)—S—R*; —O—(C=O)—H; —O—(C=O)—R*; —S—(C=O)—R*; —(C=O)—$NH_2$; —(C=O)—N(R*)$_2$; —(C=O)—$NHNH_2$; —O—(C=O)—$NHNH_2$; —(C=S)—$NH_2$; —(C=S)—N(R*)$_2$; —N(R*)—CHO; —N(R*)—(C=O)—R*; —SCN; —NCS; —NSO; —SSR*; —$SO_2R$*; —$SO_3H$; —$SO_2$—N(R*)$_2$; —S(=O)—OR*; —S(=O)—R*; —Si(R*)$_3$; —$CF_3$; —O—$CF_3$; —P(R*)$_2$; —O—P(=O)(OR*)$_2$; —P(=O)(OR*)$_2$; $C_1$-$C_8$ perfluorocarbon; an aliphatic $C_1$-$C_{12}$ hydrocarbon; an aromatic $C_1$-$C_{12}$ hydrocarbon; and a $C_1$-$C_{12}$ heteroaryl, with a proviso that A is not —N(R*)—(C=O)—H or —N(R*)—(C=O)—$CH_3$.

In some embodiments A is selected from —$NO_2$; —$NH_2$; —NHR*. In some embodiments A is —$NO_2$.

In some embodiments A is not —N(R*)—(C=O)—R*, or, more specifically, A is not —N(R*)—(C=O)—H, or —N(R*)—(C=O)—$CH_3$. In some embodiments A is not $NH_2$; —NHR*; or —N(R*)$_2$. In some embodiments A is not hydrogen. In some embodiments A is not a halide.

B is selected from hydrogen, —F; —Cl; —Br; —I; —OH, —OR*; —NO; —$NO_2$; —$NO_3$; —O—NO; —$N_3$; —$NH_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —$CO_2H$; —$CO_2R$*; —(C=O)—S—R*; —O—(C=O)—H; —O—(C=O)—R*; —S—(C=O)—R*; —(C=O)—$NH_2$; —O—(C=O)—$NHNH_2$; —(C=S)—$NH_2$; —(C=S)—N(R*)$_2$; —N(R*)—CHO; —N(R*)—(C=O)—R*; —SCN; —NCS; —NSO; —SSR*; —$SO_2R$*; —$SO_3H$; —$SO_2$—N(R*)$_2$; —S(=O)—OR*; —S(=O)—R*; —Si(R*)$_3$; —$CF_3$; —O—$CF_3$; —P(R*)$_2$; —O—P(=O)(OR*)$_2$; —P(=O)(OR*)$_2$; $C_1$-$C_8$ perfluorocarbon; an aliphatic $C_1$-$C_{12}$ hydrocarbon; an aromatic $C_1$-$C_{12}$ hydrocarbon; and a $C_1$-$C_{12}$ heteroaryl.

In some embodiments B is selected from —(C=O)—R*; —$CO_2H$; —$CO_2R$*. In some embodiments B may be —$CO_2R$*, where R* is a hydrogen or a $C_1$-$C_{12}$ hydrocarbon. In some embodiments B is —$CO_2R$* and R* is selected from hydrogen, methyl, ethyl, propyl, or butyl groups.

In some embodiments B is not —$CO_2H$. In some embodiments B is not —(C=O)—NHR*.

R* is independently selected at each occurrence from hydrogen or $C_1$-$C_{12}$ hydrocarbons each of which optionally contains 1-8 heteroatoms selected from halogen, O, N, and S and combinations thereof.

n is 0 or 1.

In some embodiments, n is 0, i.e., the compound of formula (I) is a dipyrrole. In other embodiments n is 1, i.e., the compound of formula (I) is a tripyrrole.

In one embodiment, the compounds of the invention are oligopyrrolamides.

In another embodiment, a compound of the invention has the following structural formula:

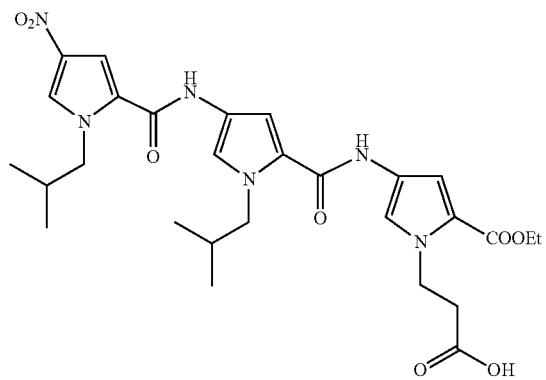

(ADH-101)

In yet another embodiment, a compound of the invention has the following structural formula:

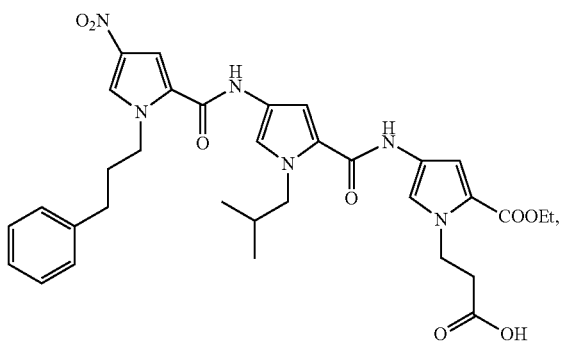

(ADH-120)

or a pharmaceutically acceptable salt thereof.

In one aspect of the invention, pharmaceutical compositions comprising the above compounds as active agents optionally in combination with a pharmaceutically acceptable carrier, additive or excipient are provided. The pharmaceutical compositions comprising an effective amount of one or more of the compounds of the invention may be formulated as a pharmaceutical dosage form for administration to a subject.

In one aspect, compounds and/or pharmaceutical compositions of the invention may be used for altering the structure of an amyloidogenic peptide. In some embodiments, compounds and/or pharmaceutical compositions according to the invention may be useful for altering structures of amyloidogenic peptides including, without limitation, islet amyloid polypeptide (IAPP), Aβ, α-synuclein, AA amyloid, PrP, $β_2$-microglobulin amyloid, transthyretin, prealbumin, and procalcitonin. In some embodiments compounds and/or pharmaceutical compositions according to the invention may be useful for altering the structure of IAPP.

In one aspect, compounds and/or pharmaceutical compositions of the invention may be used for modulating oligomerization of an amyloidogenic peptide. In some embodiments, compounds and/or pharmaceutical compositions according to the invention may be useful for modulating oligomerization of amyloidogenic peptides including, without limitation, islet amyloid polypeptide (IAPP), Aβ, α-synuclein, AA amyloid, PrP, $β_2$-microglobulin amyloid, transthyretin, prealbumin, and procalcitonin. In some embodiments compounds and/or pharmaceutical compositions according to the invention may be useful for modulating oligomerization of IAPP.

In one aspect, compounds and/or pharmaceutical compositions of the invention may be used for inhibiting oligomerization of an amyloidogenic peptide. In some embodiments, compounds and/or pharmaceutical compositions according to the invention may be useful for inhibiting oligomerization of amyloidogenic peptides including, without limitation, islet amyloid polypeptide (IAPP), Aβ, α-synuclein, AA amyloid, PrP, $β_2$-microglobulin amyloid, transthyretin, prealbumin, and procalcitonin. In some embodiments compounds and/or pharmaceutical compositions according to the invention may be useful for inhibiting oligomerization of IAPP.

In one aspect, compounds and/or pharmaceutical compositions of the invention may be used for inhibiting (i.e., reducing, diminishing, or decreasing) cytotoxicity of an amyloidogenic peptide. In some embodiments, compounds and/or pharmaceutical compositions according to the invention may be useful for inhibiting cytotoxicity of amyloidogenic peptides including, without limitation, islet amyloid polypeptide (IAPP), aβ, α-synuclein, AA amyloid, PrP, $β_2$-microglobulin amyloid, transthyretin, prealbumin, and procalcitonin. In some embodiments compounds and/or pharmaceutical compositions according to the invention may be useful for inhibiting cytotoxicity of IAPP.

In one aspect, compounds and/or pharmaceutical compositions of the invention may be used for treating diseases and/or conditions associated with a formation of oligomers or fibers of amyloidogenic peptides. In some embodiments, compounds and/or pharmaceutical compositions according to the invention may be useful for treating diseases and/or conditions associated with a formation of oligomers or fibers of amyloidogenic peptides including, without limitation, islet amyloid polypeptide (IAPP), Aβ, α-synuclein, AA amyloid, PrP, $β_2$-microglobulin amyloid, transthyretin, prealbumin, and procalcitonin. In some embodiments compounds and/or pharmaceutical compositions according to the invention may be useful for treating diseases and/or conditions associated with a formation of oligomers or fibers of IAPP.

In one aspect, compounds and/or pharmaceutical compositions according to the invention may be useful for treating diseases selected from insulinoma, diabetes mellitus (including type I diabetes and type II diabetes), hyperglycemia, and islet rejection following pancreatic islet transplantation.

In one aspect, compounds and/or pharmaceutical compositions according to the invention may be useful for treating diseases selected from Alzheimer's Disease (AD), Parkinson's disease, Mild Cognitive Impairment (MCI), inclusion body myositis, cerebral amyloid angiopathy, systemic AA amyloidosis, Lewy body diseases including Lewy body dementia, multiple system atrophy, Down's syndrome, hereditary cerebral hemorrhage with amyloidosis of the Dutch type, inclusion body myositosis, amyloidosis associated with chronic inflammation, various forms of malignancy and Familial Mediterranean Fever, inflammation-associated amyloidosis, amyloidosis associated with multiple myeloma and other B-cell dyscrasias, amyloidosis associated with the prion diseases (including, e.g., Creutzfeldt-Jakob disease, Gerstmann-Straussler syndrome, kuru and animal scrapie), amyloidosis associated with long-term hemodialysis or carpal tunnel syndrome, amyloidosis associated with senile cardiac amyloid and Familial Amyloidotic Polyneuropathy, amyloidosis associated with endocrine tumors such as medullary carcinoma of the thyroid.

In another aspect of the invention, methods for modulating oligomerization and/or fibrillation of amyloidogenic peptides with compounds and/or pharmaceutical compositions of the present invention are provided. In some embodiments, methods of modulating oligomerization and/or fibrillation of amyloidogenic peptides are provided, including, without limitation, methods of modulating oligomerization and/or fibrillation of islet amyloid polypeptide (IAPP), Aβ, α-synuclein, AA amyloid, PrP, $β_2$-microglobulin amyloid, transthyretin, prealbumin, and procalcitonin.

In another aspect of the invention, methods for inhibiting oligomerization and/or fibrillation of amyloidogenic peptides with compounds and/or pharmaceutical compositions of the present invention are provided. In some embodiments, methods of inhibiting oligomerization and/or fibrillation of amyloidogenic peptides are provided, including, without limitation, methods of inhibiting oligomerization and/or fibrillation of islet amyloid polypeptide (IAPP), Aβ, α-synuclein, AA amyloid, PrP, $β_2$-microglobulin amyloid, transthyretin, prealbumin, and procalcitonin.

In one aspect, methods of altering the structure of an amyloidogenic peptide with compounds and/or pharmaceutical compositions of the present invention are provided. In some embodiments, methods of altering structures of amyloidogenic peptides including, without limitation, islet amyloid polypeptide (IAPP), Aβ, α-synuclein, AA amyloid, PrP, $β_2$-microglobulin amyloid, transthyretin, prealbumin, and procalcitonin with compounds and/or pharmaceutical compositions of the present invention are provided. In some embodiments methods of altering the structure of IAPP with compounds and/or pharmaceutical compositions of the present invention are provided.

In one aspect, methods of inhibiting cytotoxicity of an amyloidogenic peptide with compounds and/or pharmaceutical compositions of the present invention are provided. In some embodiments, methods of inhibiting cytotoxicity of amyloidogenic peptides including, without limitation, islet amyloid polypeptide (IAPP), Aβ, α-synuclein, AA amyloid, PrP, $β_2$-microglobulin amyloid, transthyretin, prealbumin, and procalcitonin with compounds and/or pharmaceutical compositions of the present invention are provided. In some embodiments methods of inhibiting cytotoxicity of IAPP with compounds and/or pharmaceutical compositions of the present invention are provided.

In one aspect, methods of treating diseases and/or conditions associated with a formation of oligomers or fibers of amyloidogenic peptides with compounds and/or pharmaceutical compositions of the present invention are provided. In some embodiments, methods of treating diseases and/or conditions associated with a formation of oligomers or fibers of amyloidogenic peptides including, without limitation, islet amyloid polypeptide (IAPP), Aβ, α-synuclein, AA amyloid, PrP, β$_2$-microglobulin amyloid, transthyretin, prealbumin, and procalcitonin with compounds and/or pharmaceutical compositions of the present invention are provided. In some embodiments methods of treating diseases and/or conditions associated with a formation of oligomers or fibers of amyloidogenic peptides of IAPP with compounds and/or pharmaceutical compositions of the present invention are provided.

In one aspect, methods of treating diseases and/or conditions associated with a formation of oligomers or fibers of amyloidogenic peptides with compounds according to the invention which are capable of inhibiting oligomerization of an amyloidogenic peptide and/or pharmaceutical compositions comprising such compounds are provided. In some embodiments, methods of treating diseases and/or conditions associated with a formation of oligomers or fibers of amyloidogenic peptides including, without limitation, islet amyloid polypeptide (IAPP), Aβ, α-synuclein, AA amyloid, PrP, β$_2$-microglobulin amyloid, transthyretin, prealbumin, and procalcitonin with compounds according to the invention capable of inhibiting oligomerization of an amyloidogenic peptide and/or pharmaceutical compositions comprising such compounds are provided. In some embodiments methods of treating diseases and/or conditions associated with a formation of oligomers or fibers of amyloidogenic peptides of IAPP with compounds according to the invention which are capable of inhibiting oligomerization of an amyloidogenic peptide and/or pharmaceutical compositions comprising such compounds are provided.

In one aspect, methods of treating diseases selected from insulinoma, diabetes mellitus (including type I diabetes and type II diabetes), hyperglycemia, and islet rejection following pancreatic islet transplantation with compounds and/or pharmaceutical compositions of the inventions are provided.

In one aspect, methods of treating diseases selected from Alzheimer's Disease (AD), Parkinson's disease, Mild Cognitive Impairment (MCI), inclusion body myositis, cerebral amyloid angiopathy, systemic AA amyloidosis, Lewy body diseases including Lewy body dementia, multiple system atrophy, Down's syndrome, hereditary cerebral hemorrhage with amyloidosis of the Dutch type, inclusion body myositosis, amyloidosis associated with chronic inflammation, various forms of malignancy and Familial Mediterranean Fever, inflammation-associated amyloidosis, amyloidosis associated with multiple myeloma and other B-cell dyscrasias, amyloidosis associated with the prion diseases (including, e.g., Creutzfeldt-Jakob disease, Gerstmann-Straussler syndrome, kuru and animal scrapie), amyloidosis associated with long-term hemodialysis or carpal tunnel syndrome, amyloidosis associated with senile cardiac amyloid and Familial Amyloidotic Polyneuropathy, amyloidosis associated with endocrine tumors such as medullary carcinoma of the thyroid with compounds and/or pharmaceutical compositions of the inventions are provided.

These and other aspects of the present invention will become apparent to those skilled in the art after a reading of the following detailed description of the invention, including the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1C illustrate the synthesis and structures of some compounds according to embodiments of the disclosure. FIG. 1(A) shows a generic scheme for the synthesis of oligopyrroles according to an embodiment of the disclosure. (A) Alkyl halide, acetone, K$_2$CO$_3$, reflux, 12 h. (B) NaOH (1M), MeOH, 65° C., 6 h. (C) H$_2$ (1 atm), Pd/C, EtOAc, r.t., 12 h. (D) PyBOP, DIPEA, r.t., 6 h. (E) NaOH (1M), MeOH, 65° C., 6 h. (F) Oligopyrrole-NH$_2$, PyBOP, DIPEA, r.t., 6 h. FIG. 1(B) depicts the primary sequence of IAPP with amidation at the C-terminal and a conserved disulphide bond between cysteines at position 2 and 7. FIG. 1(C) depicts a helical wheel representation of the helical subdomain of IAPP spanning residues 4 to 21. The blue, green, and yellow balls represent the positively charged, polar, and hydrophobic residues, respectively.

FIGS. 2A-2G illustrate the antiamyloidogenic effect of some compounds according to embodiments of the disclosure on the aggregation kinetics of IAPP under de novo and lipid membrane conditions. FIG. 2(A) ThT fluorescence time courses of lipid catalyzed (750 μM, LUVs, DOPG: DOPC, 3:7, d=100 nm) aggregation kinetics of 15 μM IAPP in the absence and presence of ADH-101 at the indicated stoichiometric ratios. FIG. 2(B) demonstrates inhibition of IAPP (15 μM lipid condition and 15 μM for lipid free) aggregation using various doses of ADH-101. FIG. 2(C) illustrates the comparison of $t_{50}$ for 15 μM IAPP aggregation of ADH-101 and its various analogs at equimolar ratio. FIG. 2(D) shows a statistical analysis of IAPP amyloid inhibition by the indicated molecules at an equimolar ratio. FIG. 2(E) illustrates the oligomerization of 15 μM IAPP in the presence and absence of equimolar ratio of ADH-101 monitored using PICUP-SDS-PAGE-silver staining. Lane (i): IAPP, 0.5 h; (ii): IAPP, 1 h; (iii): IAPP, 2 h; (iv): IAPP, 5 h; (v): Marker; (vi): IAPP+ADH-101, 0.5 h; (vii): IAPP+ADH-101, 1 h; (viii): IAPP+ADH-101, 2 h; (ix): IAPP+ADH-101, 5 h; (x)*: IAPP+ADH-101, 5 h. FIGS. 2(F) and 2(G) demonstrate negatively stained TEM images of 10 μM IAPP incubated for 12 h in the absence (FIG. 2(F)) and presence (FIG. 2(G)) of ADH-101 at an equimolar ratio. All error bars represent SDs from a minimum of three independent experiment. *ADH-101 and the cross linking agent were pre-incubated for 2 h before adding them to IAPP. It was performed to address the potential cross linking of ADH-101 to itself.

FIG. 5(A) shows the representative kinetic profiles of 5 μM IAPP mediated membrane leakage in the absence and presence of ADH-101 at an equimolar ratio. The relative leakage was determined using the change in the fluorescence of lipid-encapsulated fluorescein dye. FIG. 5(B) shows statistical analysis of the relative change in the leakage of LUVs (250 μM) mediated by IAPP in the absence and presence of indicated small molecules at an equimolar ratio. LUVs: DOPG:DOPC, 3:7, d=100 nm. All error bars represent SDs from a minimum of three independent experiments. Buffer: 50 mM NaPi, 150 mM KCl, pH 7.4.

FIG. 7(A) shows representative amyloid kinetic profiles of 3 μM $A\beta_{42}$ in the absence and presence of ADH-101 at an equimolar ratio. FIG. 7(B) shows a comparison of the effect of ADH-101 on the aggregation kinetics of IAPP and $A\beta_{42}$ at equimolar ratio. [IAPP]=15 μM, ThT=7.5 μM, [Aβ42]=3 μM, ThT=1.5 μM. Buffer: 50 mM NaPi, 150 mM KCl, pH 7.4.

FIG. 8(A) depicts representative kinetic profiles of IAPP fibrillation probed by the change in the fluorescence intensity of ThT dye as a function of time. FIG. 8(B) shows a sigmoidal fit to extract the $t_{50}$ of one of the traces presented in FIG. 8(C). FIG. 8(C) shows normalized profiles of three independent readings of lipid catalyzed aggregation (750 LUVs, DOPG:DOPC, 3:7, d=100 nm) kinetics of 15 μM IAPP in phosphate buffer. The error bars reported for the kinetic assays in FIGS. 2 and 4 were the standard deviations from three independent experiments.

FIG. 12(A) is the plot of absorption values with increasing concentrations of ADH-101 under indicated conditions. FIG. 12(B) is a DLS plot of 25 μM ADH-101 under the identical conditions used in FIG. 12(A). Buffer conditions: 150 mM KCl, 50 mM NaPi, pH 7.4.

FIGS. 13(A) and 13(C) show representative kinetic curves of seed catalyzed (10% v,v) fibrillation of 10 μM IAPP (lipid membrane, DOPG:DOPC, 3:7, 750 μM, 100 nm) in the absence and presence of various doses of ADH-101. FIGS. 13(B) and 13(D) show statistics of repeats of seeded kinetics of IAPP fibrillation. All error bars represent SDs from a minimum of three independent experiment. Buffer: 50 mM NaPi, 150 mM KCl, pH 7.4.

DETAILED DESCRIPTION

Figure 3A:
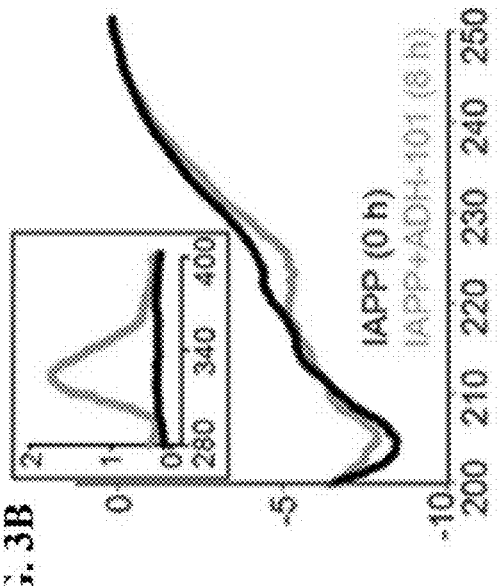
FIGS. 3(A)-3(D) illustrate time dependent structural transition of IAPP in the absence and presence of ADH-101. CD spectra of freshly prepared 15 μM IAPP incubated in phosphate buffer at the indicated time courses in the absence (FIGS. 3A and 3C) and presence (FIGS. 3B and 3D) of ADH-101 at an equimolar ratio. The solution conditions are identical in FIGS. 3C and 3D except presence of lipid membranes. Lipid membrane system (3C, 3D): [DOPG: DOPC, 3:7, d=100 nm]=750 μM. Phosphate buffer: 50 mM NaPi, 150 mM KCl, pH 7.4.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

Definitions

Unless defined otherwise, all technical and scientific terms used herein have the same meaning as commonly understood by one of ordinary skill in the art to which this invention belongs.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

A "subject" or "patient" or "individual" or "animal", as used herein, refers to humans, veterinary animals (e.g., cats, dogs, cows, horses, sheep, pigs, etc.) and experimental animal models of diseases (e.g., mice, rats). In a preferred embodiment, the subject is a human.

As used herein the term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "oligomerization", as it relates to amyloidogenic peptides, refers to a chemical process that converts individual peptide molecules into a chain consisting of a finite number of the peptide molecules. These chains are referred to as "oligomers", and they are typically soluble. As stated above, it is believed that these soluble oligomers, and not the later-stage insoluble fibrils, that are the key neurotoxic species.

The term "aggregation", as it relates to amyloidogenic peptides, refers to a process of conversion of soluble peptide oligomers into non-specific insoluble material. Under certain conditions amyloidogenic peptide oligomers aggregate into fibrils, a process referred to as fibrillation.

The term "fibrillation", as it relates to amyloidogenic peptides, refers to a process of forming fibrils. As stated above, the soluble oligomers of amyloidogenic peptides undergo the process of fibrillation, where they combine into insoluble fibrils.

The term "modulating oligomerization" or "modulating fibrillation" may refer to promoting, or agonizing, or, alternatively, inhibiting, or antagonizing, the formation of oligomers and/or fibers of a protein or a peptide.

The term "altering the structure" of a protein or a peptide refers to changing, modifying, adjusting, shifting, transforming, or causing to change, modify, adjust, shift, or transform the structural conformation of a protein or a peptide, including secondary or tertiary structure of a protein or a peptide.

The term "oligopyrrole" refers to a compound having a plurality of pyrrole rings connected via a covalent linkage, including, without limitation, an amide bond, an ester, a thioester, a ketone, and the like. The term "oligopyrrolamide" refers to a compound having a plurality of pyrrole rings connected via amide bonds. The term "dipyrrolamide" refers to a compound having two pyrrole rings connected via an amide (—(C=O)—NH—) bond. The term "tripyrrolamide" refers to a compound having three pyrrole rings connected via amide bonds. The term "tetrapyrrolamide" refers to a compound having four pyrrole rings connected via amide bonds.

Compounds of the Invention

In accordance with the foregoing objective and others, the present invention provides compounds, pharmaceutical compositions, and methods for treating diseases and conditions associated with oligomerization and/or fibrillation of an amyloidogenic peptide (e.g., islet amyloid polypeptide, or IAPP).

The compounds of the invention are useful for altering structures of one or more amyloidogenic peptides including, without limitation, islet amyloid polypeptide (IAPP), Aβ, α-synuclein, AA amyloid, PrP, $β_2$-microglobulin amyloid, transthyretin, prealbumin, and procalcitonin. Some of the compounds of the invention which are useful for altering the structure of IAPP. Without wishing to be bound by any theory, it is postulated that some of the compounds of the invention may induce α-helical conformation of IAPP, which surprisingly and unexpectedly not only inhibits the formation of IAPP fibrils, but also suppresses IAPP oligomerization in solution.

As stated above, oligopyridylamides have emerged as powerful tools to gain insight into the kinetic pathways of amyloidogenic proteins. Oligopyridylamides have been designed with two carboxylate functionalities to complement the two positive charges, R11 and H18, separated by two turns on the α-helical surface of IAPP.

Herein, a library of novel oligopyrroles has been designed by introducing functional groups at the N-positions, including, without limitation, carboxylate, alkyl (linear and branched), and benzyl groups. Without wishing to be bound by any theory, it is postulated that the N-substituted oligopyrroles may adopt a shape complementary to the side chain residues of the membrane bound α-helical intermediates of amyloidogenic peptides (e.g., IAPP), and modulate their structure and functions.

It has been surprisingly discovered that the inhibition of oligomerization and/or fibrillation of IAPP and $Aβ_{42}$ appears to be specific to the side chain functionalities present on the oligopyrrole compounds of the invention.

It has been surprisingly discovered that tripyrrole ADH-101 (shown below), is an effective antagonist of oligomerization, fibrillation, and/or aggregation of IAPP.

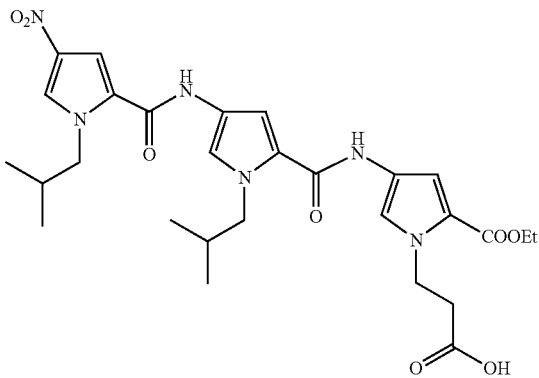

(ADH-101)

It has further been surprisingly discovered that tripyrrole ADH-120 (shown below), is an effective antagonist of oligomerization, fibrillation, and/or aggregation of IAPP.

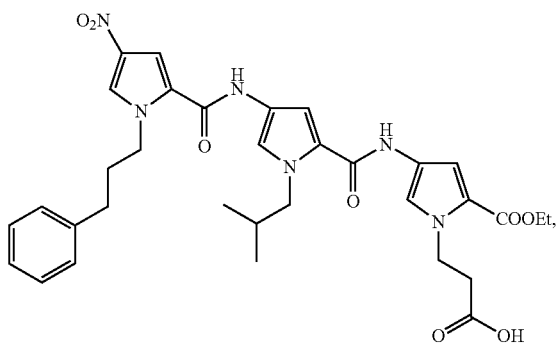

(ADH-120)

In one embodiment, the compounds of the invention (e.g., the modulators of oligomerization of amyloidogenic peptides, such as Aβ and/or IAPP) have the structure of formula (I):

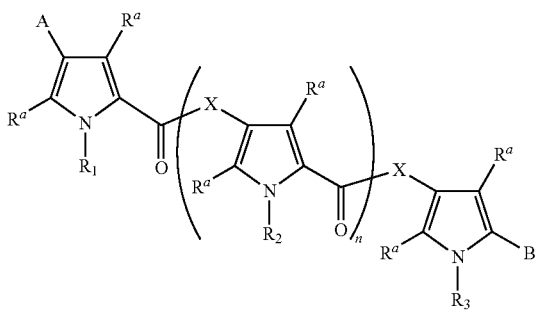

(I)

and pharmaceutically acceptable salts thereof.

In formula (I), $R^a$ is independently selected at each occurrence from hydrogen, $C_1$-$C_{12}$ hydrocarbons, —F; —Cl; —Br; —I; —OH, —OR*; —SO$_3$H; —NO; —NO$_2$; —NO$_3$; —O—NO; —N$_3$; —NH$_2$; —NHR*; and —N(R*)$_2$;

In some embodiments, $R^a$ is present at 0, 1, or 2 different positions on the ring.

In some embodiments, $R^a$ is hydrogen at all occurrences.

X is independently at each occurrence selected from —O—; —S—; —NH—; —NR*—; and —C(R*)$_2$.

In some embodiments X is —NH— or —NR*—, such that —(C=O)—X— is an amide bond, at all occurrences. In some embodiments X is —NH—, i.e. the compound is an oligopyrrolamide.

In some embodiments X is not —O—. In some embodiments X is not —S—. In some embodiments X is not C(R*)$_2$.

$R_1$, $R_2$, and/or $R_3$ are independently at each occurrence selected from hydrogen or a straight chained, branched or cyclic aliphatic $C_2$-$C_{20}$ hydrocarbon; an aromatic $C_6$-$C_{20}$ hydrocarbon; a heteroaromatic $C_2$-$C_{20}$ hydrocarbon; an aryl $C_6$-$C_{20}$ hydrocarbon; a heteroaryl $C_2$-$C_{20}$ hydrocarbon, a $C_2$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_3$H; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof.

In some embodiments $R_1$, $R_2$, and/or $R_3$ are independently at each occurrence selected from a straight chained, branched or cyclic aliphatic $C_2$-$C_{20}$ hydrocarbon; an aromatic $C_6$-$C_{20}$ hydrocarbon; a heteroaromatic $C_2$-$C_{20}$ hydrocarbon; an aryl $C_6$-$C_{20}$ hydrocarbon; a heteroaryl $C_2$-$C_{20}$ hydrocarbon, a $C_2$-$C_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3^+$; —(C=O)—R*; —CHO; —CO$_2$H; —CO$_2$R*; —(C=O)—S—R*; —O—(C=O)—H; —O—(C=O)—R*; and combinations thereof.

In some embodiments $R_1$, $R_2$, and/or $R_3$ are independently at each occurrence a straight chained, branched or cyclic aliphatic $C_2$-$C_{20}$ hydrocarbon, optionally substituted with one or more of —NH$_2$; —NHR*; —N(R*)$_2$; —N(R*)$_3^+$; —(C=O)—R*; —CO$_2$H; or —CO$_2$R*; and combinations thereof.

In some embodiments $R_1$, $R_2$, and/or $R_3$ are independently at each occurrence a straight chained, branched or cyclic $C_2$-$C_{20}$ hydrocarbon, optionally substituted with one or more of —NH$_2$; —NHR*; —N(R*)$_2$.

In some embodiments $R_1$, $R_2$, and/or $R_3$ are independently at each occurrence a straight chained, branched or cyclic aliphatic $C_2$-$C_{20}$ hydrocarbon, optionally substituted with —CO$_2$H. In some embodiments $R_1$, $R_2$, and/or $R_3$ may independently at each occurrence be —CH$_2$CO$_2$H.

In some embodiments $R_1$, $R_2$, and/or $R_3$ at all occurrences do not contain —CO$_2$H. In some embodiments $R_1$, $R_2$, and/or $R_3$ are not —CH$_2$CO$_2$H at all occurrences.

In some embodiments $R_1$, $R_2$, and/or $R_3$ are independently at each occurrence selected from an aromatic $C_6$-$C_{20}$ hydrocarbon; a heteroaromatic $C_2$-$C_{20}$ hydrocarbon; an aryl $C_6$-$C_{20}$ hydrocarbon; or a heteroaryl $C_2$-$C_{20}$ hydrocarbon optionally containing 1-8 heteroatoms selected from halogen, O, N, and S, and each of which is optionally substituted with one or more of —NH$_2$; —NHR*; —N(R*)$_2$; —N(R*)$_3^+$; —(C=O)—R*; —CHO; —CO$_2$H; —CO$_2$R*; —(C=O)—S—R*; —O—(C=O)—H; —O—(C=O)—R*.

In some embodiments, $R_1$, $R_2$, and/or $R_3$ are independently at each occurrence selected from a substituted or unsubstituted phenyl, benzyl, naphthyl, indolyl, pyrrolidinyl, pyrrolyl, imidazolyl, pyrazolyl, oxazolyl, isoxazolyl, thiazolyl, isothiazolyl, histidinyl (i.e., —CH$_2$-imidazole), triazolyl, pyridyl, pyranyl, diazinyl, oxazinyl, thiazinyl, or triazinyl.

A is selected from —OH, —OR*; —NO; —NO$_2$; —NO$_3$; —O—NO; —N$_3$; NHR*, N(R*)$_2$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_3$H; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; $C_1$-$C_8$ perfluorocarbon; an aliphatic $C_1$-$C_{12}$ hydrocarbon; an aromatic $C_1$-$C_{12}$ hydrocarbon; and a $C_1$-$C_{12}$ heteroaryl, with a proviso that A is not —N(R*)—(C=O)—H or —N(R*)—(C=O)—CH$_3$.

In some embodiments A is selected from —NO$_2$; —NH$_2$; —NHR*. In some embodiments A is —NO$_2$.

In some embodiments A is not —N(R*)—(C=O)—R*, or, more specifically, A is not —N(R*)—(C=O)—H, or —N(R*)—(C=O)—CH$_3$. In some embodiments A is not NH$_2$; —NHR*; or —N(R*)$_2$. In some embodiments A is not hydrogen. In some embodiments A is not a halide.

B is selected from hydrogen, —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_3$H; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; $C_1$-$C_8$ perfluorocarbon; an aliphatic $C_1$-$C_{12}$ hydrocarbon; an aromatic $C_1$-$C_{12}$ hydrocarbon; and a $C_1$-$C_{12}$ heteroaryl.

In some embodiments B is selected from —(C=O)—R*; —CO$_2$H; —CO$_2$R*. In some embodiments B may be —CO$_2$R*, where R* is a hydrogen or a $C_1$-$C_{12}$ hydrocarbon. In some embodiments B is —CO$_2$R* and R* is selected from hydrogen, methyl, ethyl, propyl, or butyl groups.

In some embodiments B is not —CO$_2$H. In some embodiments B is not —(C=O)—NHR*.

R* is independently selected at each occurrence from hydrogen or $C_1$-$C_{12}$ hydrocarbons each of which optionally contains 1-8 heteroatoms selected from halogen, O, N, and S and combinations thereof.

n is 0 or 1.

In some embodiments, n is 0, i.e., the compound of formula (I) is a dipyrrole. In other embodiments n is 1, i.e., the compound of formula (I) is a tripyrrole. In some embodiments, n is 0, and X is —NH—, i.e., the compound of formula (I) is a dipyrrolamide. In other embodiments n is 1, and X is —NH—, i.e., the compound of formula (I) is a tripyrrolamide.

In one embodiment, the compounds of the invention are oligopyrrolamides.

In one embodiment, the compounds of the invention have the structure of formula (II):

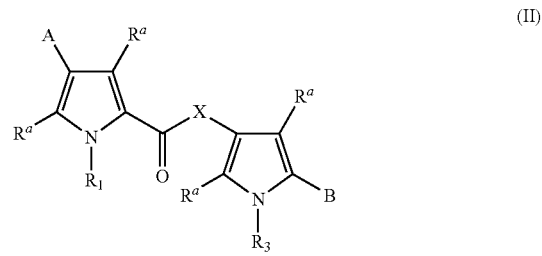

and pharmaceutically acceptable salts thereof, wherein $R^a$, $R_1$, $R_3$, A, B, and X are as described above, i.e. the compounds of formula (II) are dipyrroles. In some embodiments X is —NH—, i.e. the compounds of formula (II) are dipyrrolamides.

In one embodiment, the compounds of the invention have the structure of formula (III):

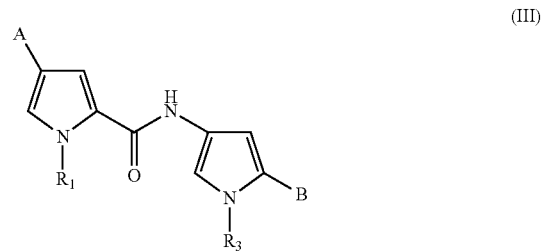

and pharmaceutically acceptable salts thereof, wherein $R_1$, $R_3$, A, and B, are as described above.

In some embodiments, the compounds of formula (III) have $R_1$ and/or $R_3$ independently selected from a straight chained, branched or cyclic aliphatic $C_2$-$C_{20}$ hydrocarbon; an aromatic $C_6$-$C_{20}$ hydrocarbon; a heteroaromatic $C_2$-$C_{20}$ hydrocarbon; an aryl $C_6$-$C_{20}$ hydrocarbon; a heteroaryl $C_2$-$C_{20}$ hydrocarbon, a $C_2$-$C_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3^+$; —(C=O)—R*; —CHO; —CO$_2$H; —CO$_2$R*; —(C=O)—S—R*; —O—(C=O)—H; —O—(C=O)—R*; SO$_3$H and combinations thereof.

In some embodiments, the compounds of formula (III) have $R_1$ and/or $R_3$ independently selected from a straight chained, branched or cyclic aliphatic $C_2$-$C_{20}$ hydrocarbon; an aromatic $C_6$-$C_{20}$ hydrocarbon; a heteroaromatic $C_2$-$C_{20}$ hydrocarbon; an aryl $C_6$-$C_{20}$ hydrocarbon; a heteroaryl $C_2$-$C_{20}$ hydrocarbon, a $C_2$-$C_{12}$ perfluorocarbon, or a combination thereof, each of which is optionally substituted with one or more of —(C=O)—R*; —CO$_2$H; —CO$_2$R*; and combinations thereof.

In some embodiments, the compounds of formula (III) have A selected from —NO$_2$; —N(R*)—(C=O)—R*, —N(R*)$_2$, where R* is hydrogen or an aliphatic $C_1$-$C_{12}$ hydrocarbon.

In some embodiments A is not —N(R*)—(C═O)—H or —N(R*)—(C═O)—CH$_3$.

In some embodiments, the compounds of formula (III) have B selected from —(C═O)—R*; —CO$_2$H; —CO$_2$R*, where R* is hydrogen or an aliphatic C$_1$-C$_{12}$ hydrocarbon.

In one embodiment, the compounds of the invention have the structure of formula (IV):

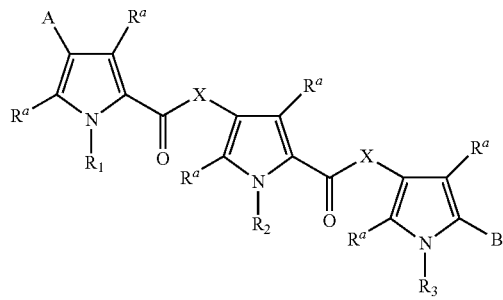

(IV)

and pharmaceutically acceptable salts thereof, wherein R$^a$, R$_1$, R$_2$, R$_3$, A, B, and X are as described above, i.e. the compounds of formula (IV) are tripyrroles. In some embodiments X is —NH—, i.e. the compounds of formula (IV) are tripyrrolamides.

In one embodiment, the compounds of the invention have the structure of formula (V):

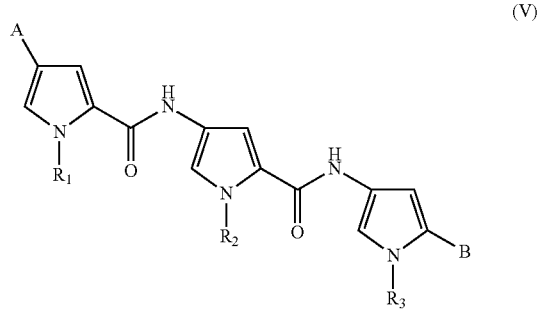

(V)

and pharmaceutically acceptable salts thereof, wherein R$^a$, R$_1$, R$_2$, R$_3$, A, B, and X are as described above.

In some embodiments, the compounds of formula (V) have R$_1$, R$_2$, and/or R$_3$ independently selected from a straight chained, branched or cyclic aliphatic C$_2$-C$_{20}$ hydrocarbon; an aromatic C$_6$-C$_{20}$ hydrocarbon; a heteroaromatic C$_2$-C$_{20}$ hydrocarbon; an aryl C$_6$-C$_{20}$ hydrocarbon; a heteroaryl C$_2$-C$_{20}$ hydrocarbon, a C$_2$-C$_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3^+$; —(C═O)—R*; —CHO; —CO$_2$H; —CO$_2$R*; —(C═O)—S—R*; —O—(C═O)—H; —O—(C═O)—R*; —SO$_3$H; and combinations thereof.

In some embodiments, the compounds of formula (V) have R$_1$, R$_2$, and/or R$_3$ independently selected from a straight chained, branched or cyclic aliphatic C$_2$-C$_{20}$ hydrocarbon; an aromatic C$_6$-C$_{20}$ hydrocarbon; a heteroaromatic C$_2$-C$_{20}$ hydrocarbon; an aryl C$_6$-C$_{20}$ hydrocarbon; a heteroaryl C$_2$-C$_{20}$ hydrocarbon, a C$_2$-C$_{12}$ perfluorocarbon, or a combination thereof, each of which is optionally substituted with one or more of —(C═O)—R*; —CO$_2$H; —CO$_2$R*; SO$_3$H and combinations thereof.

In some embodiments, the compounds of formula (V) have A selected from —NO$_2$; —N(R*)—(C═O)—R*, —N(R*)$_2$, where R* is hydrogen or an aliphatic C$_1$-C$_{12}$ hydrocarbon.

In some embodiments A is not —N(R*)—(C═O)—H or —N(R*)—(C═O)—CH$_3$.

In some embodiments, the compounds of formula (V) have B selected from —(C═O)—R*; —CO$_2$H; —CO$_2$R*, where R* is hydrogen or an aliphatic C$_1$-C$_{12}$ hydrocarbon.

In another embodiment, a compound of the invention has the following structural formula:

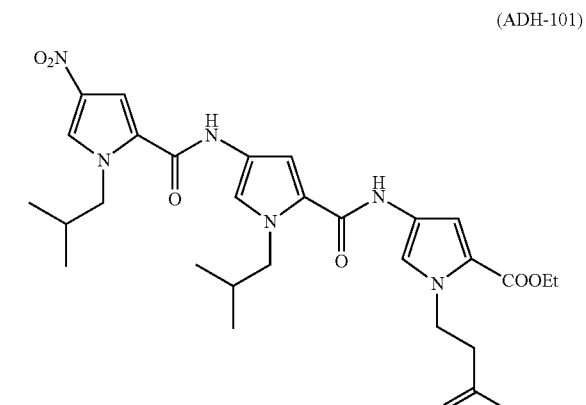

(ADH-101)

In yet another embodiment, a compound of the invention has the following structural formula:

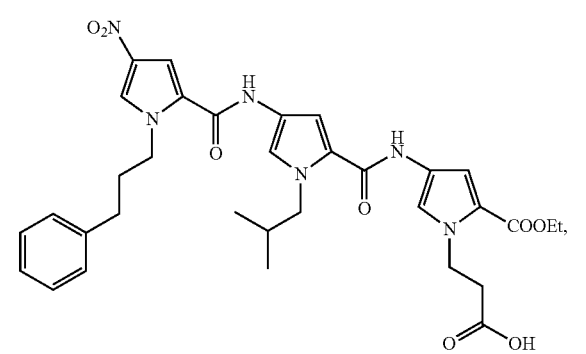

(ADH-120)

or a pharmaceutically acceptable salt thereof.

Some exemplary non-limiting embodiments of the compounds of the invention (and their monomer precursors) are shown below:
ADH-101
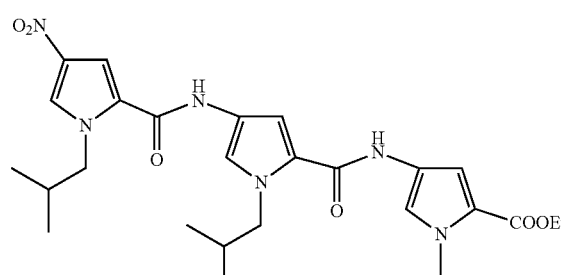
ADH-102
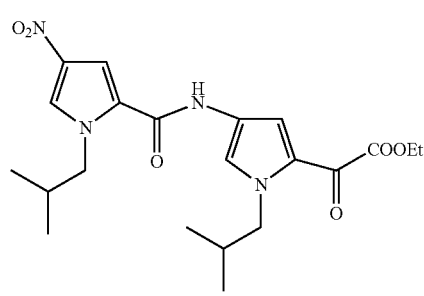
ADH-103
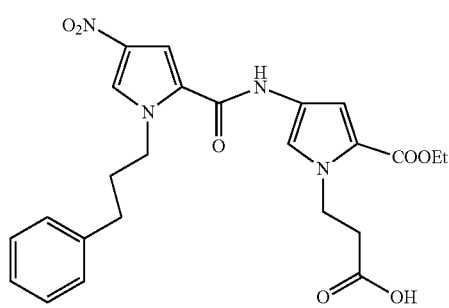
ADH-104
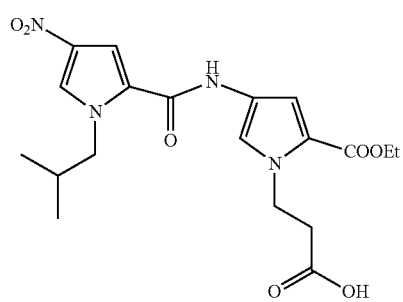
ADH-105
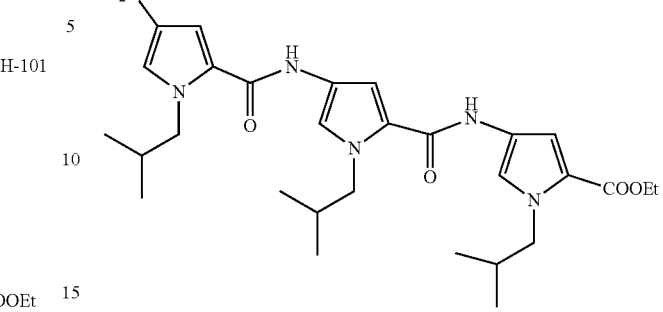
ADH-106
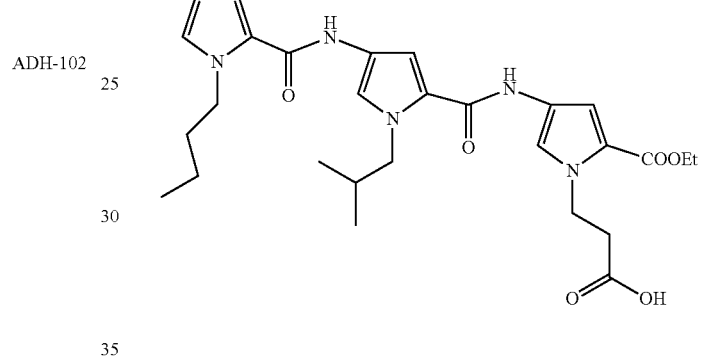
ADH-107
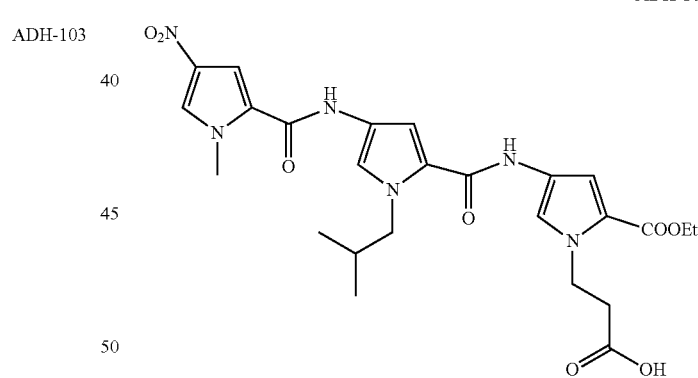
ADH-108
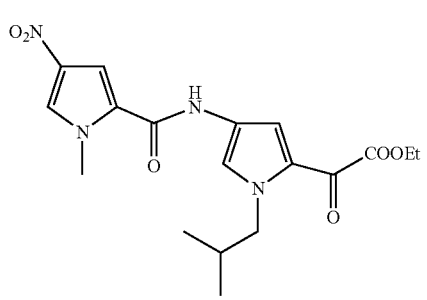

ADH-109
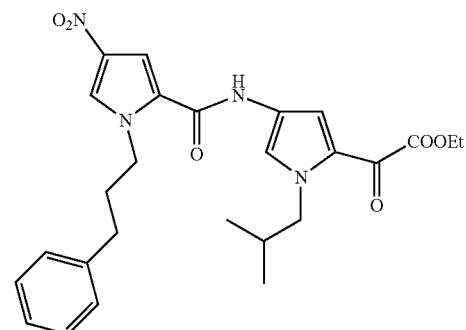
ADH-110
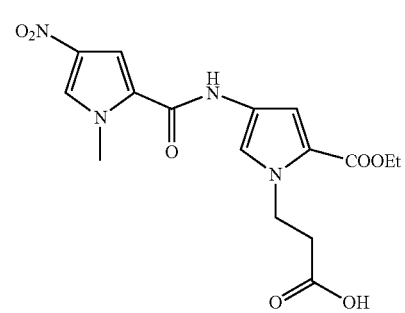
ADH-111
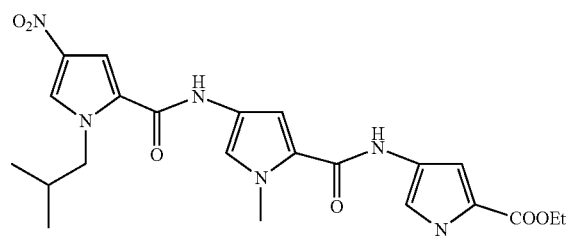
ADH-112
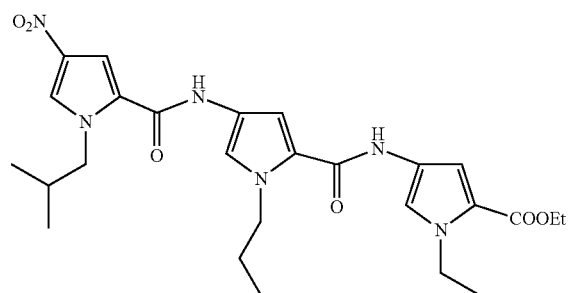
ADH-113
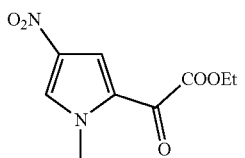
ADH-114
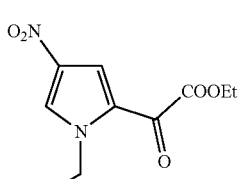
ADH-115
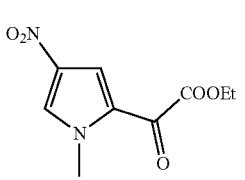
ADH-116
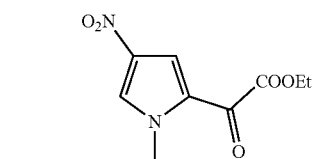
ADH-117
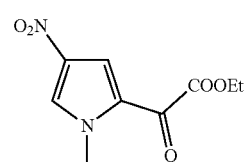
ADH-118
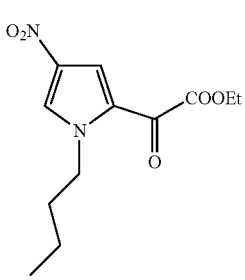

-continued

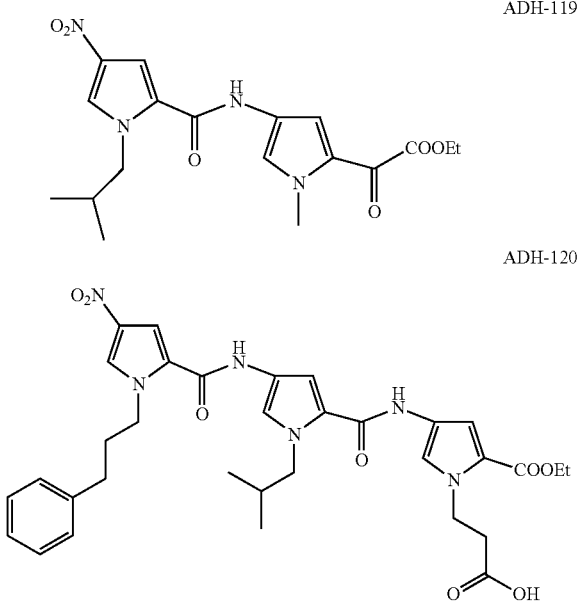

ADH-119

ADH-120

In one aspect of the invention, pharmaceutical compositions comprising the above compounds as active agents optionally in combination with a pharmaceutically acceptable carrier, additive or excipient are provided. The pharmaceutical compositions comprising an effective amount of one or more of the compounds of the invention may be formulated as a pharmaceutical dosage form for administration to a subject.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The present application also includes salts of the compounds described herein. As used herein, "salts" refers to derivatives of the disclosed compounds wherein the parent compound is modified by converting an existing acid or base moiety to its salt form. Examples of salts include, but are not limited to, mineral acid (such as HCl, HBr, $H_2SO_4$) or organic acid (such as acetic acid, benzoic acid, trifluoroacetic acid salts of basic residues such as amines; alkali (such as Li, Na, K, Mg, Ca) or organic (such as trialkylammonium) salts of acidic residues such as carboxylic acids; and the like. The salts of the present application can be synthesized from the parent compound which contains a basic or acidic moiety conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred.

The present application also includes pharmaceutically acceptable salts of the compounds described herein. The "pharmaceutically acceptable salts" include a subset of the "salts" described above which are conventional non-toxic salts of the parent compound formed, for example, from non-toxic inorganic or organic acids. Lists of suitable salts are found in Remington's Pharmaceutical Sciences, 17th ed., Mack Publishing Company, Easton, Pa., 1985, p. 1418 and Journal of Pharmaceutical Science, 66, 2 (1977). The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts and Greene, *Greene Protective Groups in Organic Synthesis,* 4th Ed., John Wiley & Sons: New York, 2006.

Pharmaceutical Compositions and Dosage Forms

The present invention also provides pharmaceutical compositions comprising the compounds described herein. When employed as pharmaceuticals, the compounds of the invention can be administered in the form of pharmaceutical compositions which is a combination of the compounds of the invention and a pharmaceutically acceptable carrier. These compositions can be prepared in a manner well known in the pharmaceutical art, and can be administered by a variety of routes. Such pharmaceutical compositions can be administered systemically. The term "systemic" as used herein includes parenteral, topical, transdermal, oral, by inhalation/pulmonary, rectal, nasal, buccal, and sublingual administration. The term "parenteral" as used herein includes subcutaneous, intradermal, intravenous, intramuscular, intracranial, and intraperitoneal administration. Preferably, the compounds are administered intramuscularly, subcutaneously, orally, or intranasally in therapeutically effective amounts to treat diseases associated with a formation of oligomers and/or fibers of amyloidogenic peptides (e.g., IAPP).

Pharmaceutical compositions containing the compounds of the invention can be prepared in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In some embodiments, the pharmaceutical composition of the invention is in liquid form. Liquid forms include, by way of non-limiting example, emulsions, solutions, suspensions, syrups, slurries, dispersions, colloids and the like. In some embodiments, a pharmaceutical composition described herein is in liquid, semi-solid or solid (e.g., powder) form.

In specific embodiments, a pharmaceutical composition described herein is in semi-solid form, e.g., a gel, a gel matrix, a cream, a paste, or the like. In some embodiments, semi-solid forms comprise a liquid vehicle. In some embodiments, the pharmaceutical composition of the invention is a solid dosage form, such a tablet, a granule, a sachet, or a powder. Also provided are pharmaceutical compositions comprising a compound of the invention or a pharmaceutically acceptable salt thereof in the form of a dissolving tablet, a dissolving wafer, a capsule, or a gel capsule. In certain embodiments, solid dosage forms described herein comprise a solid vehicle (e.g., as used in a tablet), and/or a gaseous vehicle (e.g., as used in DPI).

In some embodiments, a composition is in a unit dose formulation for oral, intranasal, or other administration to a patient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, the compounds or compositions described herein are administered intranasally. As used herein, "nasal delivery-enhancing agents" include agents which enhance the release or solubility (e.g., from a formulation delivery vehicle), diffusion rate, penetration capacity and timing, uptake, residence time, stability, effective half-life, peak or sustained concentration levels, clearance and other desired nasal delivery characteristics (e.g., as measured at the site of delivery, or at a selected target site of activity such as the brain) of the compounds or compositions of the invention. Enhancement of mucosal delivery can thus occur by any of a variety of mechanisms, for example by increasing the diffusion, transport, persistence or stability of the compounds or compositions of the invention, enzyme inhibition, increasing membrane fluidity, modulating the availability or action of calcium and other ions that regulate intracellular or paracellular permeation, solubilizing mucosal membrane components (e.g., lipids), changing nonprotein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, increasing nasal blood flow and other mechanisms. Suitable mucosal delivery enhancing agents will be clear to a person skilled in the art of pharmacology and are further described hereafter.

Compositions of the invention can be simple aqueous (e.g., saline) solutions. Alternatively, they can contain various additional ingredients which enhance stability and/or nasal delivery of the compounds of the invention. Such additional ingredients are well known in the art. Non-limiting examples of useful additional ingredients for enhancing nasal delivery include, e.g., (a) aggregation inhibitory agents (e.g., polyethylene glycol, dextran, diethylaminoethyl dextran, and carboxymethyl cellulose), (b) charge modifying agents, (c) pH control agents, (d) degradative enzyme inhibitors (e.g., amastatin and bestatin [see, e.g., O'Hagan et al., *Pharm. Res.* 1990, 7: 772-776 and WO 05/120551]; (e) mucolytic or mucus clearing agents (e.g., n-acetyl-cysteine, propyl gallate and cysteine methionine dimers, chaotropes [see, e.g., WO 04/093917]), (f) ciliostatic agents; (g) membrane penetration enhancing agents, (h) modulatory agents of epithelial junction physiology, such as nitric oxide (NO) stimulators, chitosan, and chitosan derivatives; (i) vasodilator agents, (j) selective transport-enhancing agents, and (k) stabilizing delivery vehicles, carriers, supports or complex-forming agents. See, e.g., EP 037943, EP 094157, EP 173990, EP 214898, EP 215697, EP 327756, EP 490806, U.S. Pat. Nos. 4,476,116, 5,759,565, WO 04/093917 and WO 05/120551.

Non-limiting examples of membrane penetration-enhancing agents useful in the compositions of the invention include, e.g., (i) a surfactant (e.g., Tween 80, Poloxamer 188, polysorbates; see also EP 490806, U.S. Pat. No. 5,759, 565, and WO04/093917), (ii) a bile salt or bile salt derivative (e.g., unsaturated cyclic ureas and Transcutol), (iii) a phospholipid or fatty acid additive, mixed micelle, liposome, or carrier, (iv) an alcohol, (v) an enamine, (vi) a nitric oxide donor compound (e.g., S-nitroso-N-acetyl-DL-penicillamine, NOR1, NOR4, which are preferably co-administered with an NO scavenger such as carboxy-PITO or doclofenac sodium), (vii) a long-chain amphipathic molecule (e.g., deacylmethyl sulfoxide, azone, sodium lauryl sulfate, oleic acid) (viii) a small hydrophobic penetration enhancer, (ix) sodium salicylate or a salicylic acid derivative (e.g., acetyl salicylate, choline salicylate, salicylamide, etc.), (x) a glycerol ester of acetoacetic acid, (xi) a cyclodextrin or betacyclodextrin derivative, (xii) a medium-chain fatty acid including mono- and diglycerides (e.g., sodium caprate—extracts of coconut oil, Capmul), (xiii) a chelating agent (e.g., citric acid, salicylates), (xiv) an amino acid or salt thereof (e.g. monoaminocarboxlic acids such as glycine, alanine, phenylalanine, proline, hydroxyproline, etc.; hydroxyamino acids such as serine; acidic amino acids such as aspartic acid, glutamic acid, etc; and basic amino acids such as lysine etc., inclusive of their alkali metal or alkaline earth metal salts), (xv) an N-acetylamino acid or salt thereof, (xvi) an enzyme degradative to a selected membrane component, (xvii) an inhibitor of fatty acid synthesis, (xviii) an inhibitor of cholesterol synthesis, (xix) cationic polymers, or any combination thereof. The membrane penetration-enhancing agent can be also selected from small hydrophilic molecules, including but not limited to, dimethyl sulfoxide (DMSO), dimethylformamide, ethanol, propylene glycol, and the 2-pyrrolidones. Additional membrane penetration enhancers include emulsifiers (e.g. sodium oleyl phosphate, sodium lauryl phosphate, sodium lauryl sulfate, sodium myristyl sulfate, polyoxyethylene alkyl ethers, polyoxyethylene alkyl esters, etc.), caproic acid, lactic acid, malic acid and citric acid and alkali metal salts thereof, pyrrolidonecarboxylic acids, alkylpyrrolidonecarboxylic acid esters, N-alkylpyrrolidones, proline acyl esters, and the like; mixed micelles; glycerol esters of acetoacetic acid (e.g., glyceryl-1,3-diacetoacetate or 1,2-isopropylideneglycerine-3-acetoacetate), and triglycerides (e.g., amylodextrin, Estaram 299, Miglyol 810); cyclodextrins and β-cyclodextrin derivatives (e.g., 2-hydroxypropyl-β-cyclodextrin and heptakis (2,6-di-O-methyl-β-cyclodextrin) which can be optionally conjugated with Peptide and further optionally formulated in an oleaginous base; and N-acetylamino acids (N-acetylalanine, N-acetylphenylalanine, Nacetylserine, N-acetylglycine, N-acetyllysine, N-acetylglutamic acid, N-acetylproline, Nacetylhydroxyproline, etc.) and their salts (alkali metal salts and alkaline earth metal salts), as well as other penetration-promoting agents that are physiologically compatible for intranasal delivery. See, e.g., WO 04/093917, WO 05/120551 and Davis and Ilium (*Clin. Pharmacokinet* 2003, 42: 1107-1128).

Non-limiting examples of useful absorption enhancers include, e.g., surfactants, glycosides, cyclodextrin and glycols. Non-limiting examples of useful bioadhesive agents include, e.g., carbopol, cellulose agents, starch, dextran, and chitosan.

In various embodiments of the invention, a compound of the invention is combined with one or more of the nasal delivery-enhancing agents recited above. These nasal delivery-enhancing agents may be admixed, alone or together, with the nasal carrier and with the compound of the invention, or otherwise combined therewith in a pharmaceutically acceptable formulation or delivery vehicle. For nasal delivery-enhancing agents to be of value within the invention, it is generally desired that any significant changes in permeability of the mucosa be reversible within a time frame appropriate to the desired duration of drug delivery.

Furthermore, there should be no substantial, cumulative toxicity, nor any permanent deleterious changes induced in the barrier properties of the nasal mucosa with long term use.

In addition to the compound of the invention, the nasal carrier and, optionally, one or more further additives and/or agents, the composition of the invention may further comprise one or more additional therapeutic ingredients (or active substances). These therapeutic ingredients can be any compound that elicits a desired activity or therapeutic or biological response in the subject. Non-limiting examples of useful additional therapeutic ingredients is provided in the Combination Treatments section, below.

The proportion of each further component in the nasal composition of the invention may vary depending on the components used. For example, but without being limiting, the amount of nasal carrier may be in the range of from 0.1 to 99.9% by weight of the total weight or volume of the composition. When present, the amount surfactant may be in the range from about 0.01 to about 10% or higher and preferably about 0.05 to about 1.0% by weight of the total volume or weight of the composition, the amount depending on the specific surfactant used. The amount is generally kept as low as possible since above a certain level no further enhancement of absorption can be achieved and also too high of a surfactant level may cause irritation of the nasal mucosa. The amount of delivery enhancing agents may be at least 0.1%, suitably in the range from about 0.5 to 10% of the total weight of the composition. Where the composition is liquid, the enhancing agent may suitably be present in an amount of from 0.1 to 5% w/v of the total composition. Preserving agents may be present in an amount of from about 0.002 to 0.02% by weight of the total weight or volume of the composition.

The useful delivery volume of the pharmaceutical compositions of the invention is limited by the size of the nasal cavity. Suitable delivery volumes will be clear to a person skilled in the art of pharmacology. Preferably, the total composition quantity administered at each nasal application comprises from about 0.02 to 0.5 ml, preferably about 0.07 to 0.3 ml, typically about 0.09-0.1 ml.

The liquid compositions of the invention may be prepared by bringing into intimate admixture a compound the invention in the liquid carrier optionally together with the further ingredients, additives and/or agents. The solid nasal composition of the invention may be prepared in conventional manner. A compound of the invention may be admixed with the carrier particles, e.g. a polymer base or cellulose product in conventional manner, optionally with further ingredients, additives and/or agents as indicated above e.g. a mucosal delivery enhancing agent or surfactant such as disclosed. A compound of the invention may be in solution e.g. an aqueous or alcoholic solution when being mixed with the carrier particles and the solvent evaporated, e.g. under freeze-drying or spray drying. Such drying may be effected under the conventional conditions. Alternatively the mixture may be compacted or granulated and then be pulverized and/or sieved. If desired the particles may be coated. In one embodiment of the invention, the nasal composition is prepared by lyophilisation. A homogeneous solution, preferably aqueous, containing a compound of the invention and optionally containing further ingredients, additives and/or agents as discussed above, is prepared and then submitted to lyophilisation in analogy with known lyophilisation procedures, and to subsequent drying. The resulting powder may then be dissolved in a liquid excipient or nasal carrier before administration, e.g. to reconstitute nasal drops, gel or spray. Alternatively it may be administered as such in the form of lyophilized powder or it may be mixed with further ingredients, additives and/or agents as discussed above. For example, a lyophilized powder comprising a compound of the invention but free of any nasal carrier may be prepared and then admixed with the desired nasal carrier or mixture of nasal carriers.

The present invention encompasses any delivery device that is suitable for nasal administration of the compositions of the invention. Preferably, such means administers a metered dosage of the composition. The composition of the present invention may be packed in any appropriate form or container as long as a means is provided to deliver the composition to the nasal mucosa. Non-limiting examples of useful intranasal delivery devices include, e.g., instillation catheters, droppers, unit-dose containers, squeeze bottles pump sprays, airless and preservative-fee sprays, compressed air nebulizers, metered-dose inhalers, insufflators and pressurized metered dose inhalers.

For administration of a liquid in drop form, compositions of the invention can be placed in a container provided with a conventional dropper/closure device, e.g. comprising a pipette or the like, preferably delivering a substantially fixed volume of composition/drop.

For administration of an aqueous solution as a nasal spray, the aqueous solution may be dispensed in spray form by a variety of methods known to those skilled in the art. For example, such compositions will be put up in an appropriate atomising device, e.g. in a pump-atomiser, or the like. The atomising device will be provided with appropriate means, such as a spray adaptor for delivery of the aqueous spray to the naris. Preferably it will be provided with means ensuring delivery of a substantially fixed volume of composition/actuation (i.e. per spray-unit). Examples of nasal sprays include nasal actuators produced by Ing. Erich Pfeiffer GmbH, Radolfzell, Germany (see U.S. Pat. Nos. 4,511,069, 4,778,810, 5,203,840, 5,860,567, 5,893,484, 6,227,415, and 6,364,166. Additional aerosol delivery forms may include, e.g., compressed air-, jet-, ultrasonic-, and piezoelectric nebulizers.

Alternatively the spray may be bottled under pressure in an aerosol device. The propellant may be a gas or a liquid (e.g. a fluorinated and/or chlorinated hydrocarbon). The spray composition may be suspended or dissolved in a liquid propellant. Stabilizing and/or suspending agents and/or co-solvents may be present.

A dry powder may be readily dispersed in an inhalation device as described in U.S. Pat. No. 6,514,496 and Garcia-Arieta et al., *Biol. Pharm. Bull.* 2001; 24: 1411-1416.

If desired a powder or liquid may be filled into a soft or hard capsule or in a single dose device adapted for nasal administration. The powder may be sieved before filled into the capsules such as gelatine capsules. The delivery device may have means to break open the capsule. The powdery nasal composition can be directly used as a powder for a unit dosage form. The contents of the capsule or single dose device may be administered using e.g. an insufflator. Preferably it will be provided with means ensuring dosing of a substantially fixed amount of composition.

In another embodiment, the composition of the invention can be provided as a nasal insert having the compound of the invention dispersed therein. The insert may be retained in the naris, but flushed by the nasal mucus, and may be designed to release the compound of the invention at the same place in the naris. Suitable nasal insert types include nasal plugs, tampons and the like. Further examples of nasal inserts, their characteristics and preparation are described in EP 490806.

In one aspect, a composition or unit dosage form according to the invention is formulated for sublingual administration, wherein the unit dosage form is a film including one or more disintegrants (e.g., materials that favor disintegration or fast dissolution by virtue of their solubility in water, such as hydrolyzed starches, sugars, and glycerin, which may play a dual role as a plasticizer and disintegrant) and a plasticizing agent, the film having a first portion including apomorphine hydrochloride, and a second portion including pH neutralizing agent, wherein the unit dosage form includes from 0.5 to 5 mg, from 4 to 10 mg, or from 8 to 20 mg of apomorphine hydrochloride and the pH neutralizing agent is present in an amount sufficient to produce a solution having a pH of between 3.0 and 6.0, preferably between 4.5 and 6.5, (e.g., a pH of between 2.5 and 4.5, 3.0 and 6.0, 3.5 and 6.5, 4.5 and 6.5, or 5.0 and 6.0) when the unit dosage form is placed in unbuffered water at pH 7 (e.g., the pH observed within 5 minutes of placing the unit dosage form in 1, 5, or 10 mL of unbuffered water). The film can include from 1 to 50% (w/w) (e.g., 1±0.75%, 2±1.5%, 3±0.5%, 5±2%, 7.5±2.5%, 10±2%, 14±3%, 18±4%, 22±5%, 25±5%, 30±5%, 35±5%, 40±5%, 45±5%, or 50±5% (w/w)) of the one or more disintegrants. In certain embodiments, the unit dosage form further includes a high molecular weight polymer having a weight average molecular weight of greater than 60 KDa selected from hydroxypropyl cellulose, hydroxypropyl methyl cellulose, hydroxyethyl cellulose, carboxymethyl cellulose, and methyl cellulose. In other embodiments, the unit dosage form further includes a low molecular weight polymer having a weight average molecular weight of from 5 KDa to 50 KDa selected from hydroxypropyl cellulose, hydroxypropyl methyl cellulose, hydroxyethyl cellulose, carboxymethyl cellulose, and methyl cellulose. The pH neutralizing agent can be an organic base (e.g., pyridoxine, meglumine, or any organic base described herein) or an inorganic base (e.g., magnesium hydroxide, sodium bicarbonate, or an inorganic base described herein). In particular embodiments, the unit dosage form includes 35±5% (w/w) disintegrant, from 0.5 to 5 mg, from 4 to 10 mg, or from 8 to 20 mg of apomorphine hydrochloride and pyridoxine present in an amount sufficient to produce a solution having a pH of between 4.5 and 6.5 when the unit dosage form is placed in unbuffered water at pH 7. Suitable film for oral administration of the compositions according to the invention is disclosed in, e.g., U.S. Pat. No. 8,846,074.

In some embodiments, a composition or unit dosage form described herein is administered as an emulsion, a solution, a suspension, a syrup, a slurry, a dispersion, a colloid, a dissolving tablet, a dissolving wafer, a capsule, a gel capsule, a semi-solid, a solid forma gel, a gel matrix, a cream, a paste, a tablet, a granule, a sachet, a powder, or the like. In certain aspects, about 0.000001 mg to about 2000 mg, about 0.00001 mg to about 1000 mg, or about 0.0001 mg to about 750 mg, about 0.001 mg to about 500 mg, about 0.01 mg to about 250 mg, about 0.1 mg to about 100 mg, about 0.5 mg to about 75 mg, about 1 mg to about 50 mg, about 2 mg to about 40 mg, about 5 mg to about 20 mg, or about 7.5 mg to about 15 mg of compound of formula (I) per day or per dose is administered to an individual.

In some embodiments, the compound of the invention is present in a composition or a unit dose of a composition described herein in an amount of from about 0.01 mg to about 10 mg (e.g., about 0.1-10 mg, about 0.25-5 mg, about 0.25-2.5 mg, about 1-2 mg or about 2-3 mg, about 0.5 mg to about 2 mg, about 1 to about 2 mg, about 1 mg, or about 2 mg). In some embodiments, the amount of corticosteroid administered daily or in a unit dose is between about 0.5 mg and about 3 mg, between about 0.5 mg and about 4 mg, or between about 0.35 mg and about 4 mg. In other embodiments, the amount of the compound present in a unit dose or administered daily is between about 1 and about 3 mg, or between about 1 and about 2 mg, or between about 2 and about 3 mg.

In certain aspects, about 0.05 mg to about 50 mg, about 0.25 mg to about 20 mg, about 0.25 mg to about 15 mg, about 0.25 mg to about 10 mg, or about 0.25 mg to about 5 mg (e.g., about 0.1 to about 5 mg, about 0.25 to about 2.5 mg, about 0.3 mg to about 2 mg, about 0.5 mg to about 1 mg, about 0.7 mg to about 1.5 mg, about 0.375 mg, about 0.75 mg, about 1 mg, about 1.25 mg, about 1.5 mg or about 2 mg) of the compound per day or per dose is administered to a patient.

In some embodiments, the compound is present in a unit dose in an amount of between about 5 mg and about 500 mg. In some embodiments, the amount of the compound administered daily or in a unit dose is between about 5 mg and about 300 mg. In other embodiments, the amount of the compound present in a unit dose or administered daily is between about 5 and about 250 mg, or between about 5 and about 200 mg, between about 5 mg and about 150 mg, between about 5 mg and about 100 mg, or between about 5 and about 50 mg.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid pre-formulation composition containing a homogeneous mixture of a compound according to the invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.000001 to about 2000 mg of the active ingredient of the present application.

The tablets or pills containing a compound according to the invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present application can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9. It will be understood that use of certain of the foregoing excipients, carriers, or stabilizers will result in the formation of pharmaceutical salts.

The therapeutic dosage of the compounds of the invention can vary according to, for example, the particular use for which the treatment is made, the manner of administration of the compound, the health and condition of the patient, and the judgment of the prescribing physician. The proportion or concentration of the compounds of the invention in a pharmaceutical composition can vary depending upon a number of factors including dosage, chemical characteristics (e.g., hydrophobicity), and the route of administration. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The present application also includes pharmaceutical kits useful, for example, in the treatment or prevention of diseases associated with a formation of oligomers and/or fibers of amyloidogenic peptides, such as IAPP, which include one or more containers containing a pharmaceutical composition comprising a therapeutically effective amount of the compounds of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Delivery devices are important not only for delivering the compounds of the invention, but also for providing an appropriate environment for storage. This would include protection from microbial contamination and chemical degradation. The device and formulation should be compatible so as to avoid potential leaching or adsorption. The delivery device (or its packaging) can be optionally provided with a label and/or with instructions for use indicating that the composition should be used intranasally.

Methods of Use

In one aspect, compounds and/or pharmaceutical compositions of the invention may be used for altering the structure of an amyloidogenic peptide. In some embodiments, compounds and/or pharmaceutical compositions according to the invention may be useful for altering the conformation and/or structures of amyloidogenic peptides including, without limitation, islet amyloid polypeptide (IAPP), A$\beta$, $\alpha$-synuclein, AA amyloid, PrP, $\beta_2$-microglobulin amyloid, transthyretin, prealbumin, and procalcitonin. In some embodiments compounds and/or pharmaceutical compositions according to the invention may be useful for altering the structure of IAPP.

In one aspect, compounds and/or pharmaceutical compositions of the invention may be used to induce an $\alpha$-helical conformation in all or a part of an amyloidogenic peptide. In some embodiments, compounds and/or pharmaceutical compositions according to the invention may be used to promote or induce an $\alpha$-helical conformation in all or a part of amyloidogenic peptides including, without limitation, islet amyloid polypeptide (IAPP), A$\beta$, $\alpha$-synuclein, AA amyloid, PrP, $\beta_2$-microglobulin amyloid, transthyretin, prealbumin, and procalcitonin. In some embodiments compounds and/or pharmaceutical compositions according to the invention may be used to promote or induce an $\alpha$-helical conformation in all or a part of A$\beta$, or its A$\beta_{42}$ alloform. In some embodiments compounds and/or pharmaceutical compositions according to the invention may be used to promote or induce an $\alpha$-helical conformation in all or a part of IAPP. In some embodiments compounds and/or pharmaceutical compositions according to the invention may be used to promote or induce an $\alpha$-helical conformation in all or a part of $\alpha$-synuclein.

In one aspect, compounds and/or pharmaceutical compositions of the invention may be used to inhibit, hinder or prevent an α-helical conformation in all or a part of an amyloidogenic peptide. In some embodiments, compounds and/or pharmaceutical compositions according to the invention may be used to inhibit, hinder or prevent an α-helical conformation in all or a part of amyloidogenic peptides including, without limitation, islet amyloid polypeptide (IAPP), Aβ, α-synuclein, AA amyloid, PrP, β$_2$-microglobulin amyloid, transthyretin, prealbumin, and procalcitonin. In some embodiments compounds and/or pharmaceutical compositions according to the invention may be used to inhibit, hinder or prevent an α-helical conformation in all or a part of Aβ, or its Aβ$_{42}$ alloform. In some embodiments compounds and/or pharmaceutical compositions according to the invention may be used to inhibit, hinder or prevent an α-helical conformation in all or a part of IAPP. In some embodiments compounds and/or pharmaceutical compositions according to the invention may be used to inhibit, hinder or prevent an α-helical conformation in all or a part of α-synuclein.

In one aspect, compounds of the invention may exhibit selectivity and/or specificity for one or more particular amyloidogenic peptides, i.e. the compounds of the invention may selectively and/or specifically bind one or more particular amyloidogenic peptides. In one aspect, compounds of the invention may exhibit selectivity and/or specificity for one or more particular amyloidogenic peptides, i.e. the compounds of the invention may selectively and/or specifically bind one or more particular amyloidogenic peptides including, without limitation, islet amyloid polypeptide (IAPP), α-synuclein, AA amyloid, PrP, (32-microglobulin amyloid, transthyretin, prealbumin, and procalcitonin. In one embodiment, compounds of the invention may exhibit selectivity and/or specificity for AP, or its Aβ$_{42}$ alloform. In another embodiment, compounds of the invention may exhibit selectivity and/or specificity for IAPP. In another embodiment, compounds of the invention may exhibit selectivity and/or specificity for α-synuclein.

In another aspect, compounds and/or pharmaceutical compositions of the invention may be used for inhibiting oligomerization of an amyloidogenic peptide. In some embodiments, compounds and/or pharmaceutical compositions according to the invention may be useful for inhibiting oligomerization of amyloidogenic peptides including, without limitation, islet amyloid polypeptide (IAPP), Aβ, α-synuclein, AA amyloid, PrP, β$_2$-microglobulin amyloid, transthyretin, prealbumin, and procalcitonin. In some embodiments compounds and/or pharmaceutical compositions according to the invention may be useful for inhibiting oligomerization of IAPP.

In another aspect, compounds and/or pharmaceutical compositions of the invention may be used for inhibiting (i.e., reducing, diminishing, decreasing, or antagonizing) cytotoxicity of an amyloidogenic peptide. In some embodiments, compounds and/or pharmaceutical compositions according to the invention may be useful for inhibiting cytotoxicity of amyloidogenic peptides including, without limitation, islet amyloid polypeptide (IAPP), Aβ, α-synuclein, AA amyloid, PrP, β$_2$-microglobulin amyloid, transthyretin, prealbumin, and procalcitonin. In some embodiments compounds and/or pharmaceutical compositions according to the invention may be useful for inhibiting cytotoxicity of IAPP.

In another aspect, compounds and/or pharmaceutical compositions of the invention may be used for treating diseases and/or conditions associated with a formation of oligomers or fibers of amyloidogenic peptides. In some embodiments, compounds and/or pharmaceutical compositions according to the invention may be useful for treating diseases and/or conditions associated with a formation of oligomers or fibers of amyloidogenic peptides including, without limitation, islet amyloid polypeptide (IAPP), Aβ, α-synuclein, AA amyloid, PrP, β$_2$-microglobulin amyloid, transthyretin, prealbumin, and procalcitonin. In some embodiments compounds and/or pharmaceutical compositions according to the invention may be useful for treating diseases and/or conditions associated with a formation of oligomers or fibers of IAPP.

In another aspect, compounds and/or pharmaceutical compositions according to the invention may be useful for treating diseases selected from insulinoma, diabetes mellitus (including type I diabetes and type II diabetes), hyperglycemia, and islet rejection following pancreatic islet transplantation.

In another aspect, compounds and/or pharmaceutical compositions according to the invention may be useful for treating diseases selected from Alzheimer's Disease (AD), Parkinson's disease, Mild Cognitive Impairment (MCI), inclusion body myositis, cerebral amyloid angiopathy, systemic AA amyloidosis, Lewy body diseases including Lewy body dementia, multiple system atrophy, Down's syndrome, hereditary cerebral hemorrhage with amyloidosis of the Dutch type, inclusion body myositosis, amyloidosis associated with chronic inflammation, various forms of malignancy and Familial Mediterranean Fever, inflammation-associated amyloidosis, amyloidosis associated with multiple myeloma and other B-cell dyscrasias, amyloidosis associated with the prion diseases (including, e.g., Creutzfeldt-Jakob disease, Gerstmann-Straussler syndrome, kuru and animal scrapie), amyloidosis associated with long-term hemodialysis or carpal tunnel syndrome, amyloidosis associated with senile cardiac amyloid and Familial Amyloidotic Polyneuropathy, amyloidosis associated with endocrine tumors such as medullary carcinoma of the thyroid.

In another aspect of the invention, methods for modulating oligomerization and/or fibrillation of amyloidogenic peptides with compounds and/or pharmaceutical compositions of the present invention are provided. In some embodiments, methods of inhibiting oligomerization and/or fibrillation of amyloidogenic peptides are provided, including, without limitation, methods of inhibiting oligomerization and/or fibrillation of islet amyloid polypeptide (IAPP), Aβ, or its Aβ$_{42}$ alloform, α-synuclein, AA amyloid, PrP, β$_2$-microglobulin amyloid, transthyretin, prealbumin, and procalcitonin.

In one aspect, methods of altering the structure of an amyloidogenic peptide with compounds and/or pharmaceutical compositions of the present invention are provided. In some embodiments, methods of altering structures of amyloidogenic peptides including, without limitation, islet amyloid polypeptide (IAPP), Aβ, or its Aβ$_{42}$ alloform, α-synuclein, AA amyloid, PrP, β$_2$-microglobulin amyloid, transthyretin, prealbumin, and procalcitonin with compounds and/or pharmaceutical compositions of the present invention are provided. In some embodiments methods of altering the structure of IAPP with compounds and/or pharmaceutical compositions of the present invention are provided.

In one aspect, methods of inhibiting cytotoxicity of an amyloidogenic peptide with compounds and/or pharmaceutical compositions of the present invention are provided. In some embodiments, methods of inhibiting cytotoxicity of amyloidogenic peptides including, without limitation, islet amyloid polypeptide (IAPP), Aβ, or its Aβ$_{42}$ alloform, α-synuclein, AA amyloid, PrP, β$_2$-microglobulin amyloid, transthyretin, prealbumin, and procalcitonin with compounds and/or pharmaceutical compositions of the present invention are provided. In some embodiments methods of inhibiting cytotoxicity of IAPP with compounds and/or pharmaceutical compositions of the present invention are provided.

In one aspect, methods of treating diseases and/or conditions associated with a formation of oligomers or fibers of amyloidogenic peptides with compounds and/or pharmaceutical compositions of the present invention are provided. In some embodiments, methods of treating diseases and/or conditions associated with a formation of oligomers or fibers of amyloidogenic peptides including, without limitation, islet amyloid polypeptide (IAPP), Aβ, α-synuclein, AA amyloid, PrP, β$_2$-microglobulin amyloid, transthyretin, prealbumin, and procalcitonin with compounds and/or pharmaceutical compositions of the present invention are provided. In some embodiments methods of treating diseases and/or conditions associated with a formation of oligomers or fibers of amyloidogenic peptides of IAPP with compounds and/or pharmaceutical compositions of the present invention are provided.

In one aspect, methods of treating diseases selected from insulinoma, diabetes mellitus (including type I diabetes and type II diabetes), hyperglycemia, and islet rejection following pancreatic islet transplantation.

In another aspect, compounds and/or pharmaceutical compositions according to the invention may be useful for treating diseases selected from Alzheimer's Disease (AD), Parkinson's disease, Mild Cognitive Impairment (MCI), inclusion body myositis, cerebral amyloid angiopathy, systemic AA amyloidosis, Lewy body diseases including Lewy body dementia, multiple system atrophy, Down's syndrome, hereditary cerebral hemorrhage with amyloidosis of the Dutch type, inclusion body myositis, amyloidosis associated with chronic inflammation, various forms of malignancy and Familial Mediterranean Fever, inflammation-associated amyloidosis, amyloidosis associated with multiple myeloma and other B-cell dyscrasias, amyloidosis associated with the prion diseases (including, e.g., Creutzfeldt-Jakob disease, Gerstmann-Straussler syndrome, kuru and animal scrapie), amyloidosis associated with long-term hemodialysis or carpal tunnel syndrome, amyloidosis associated with senile cardiac amyloid and Familial Amyloidotic Polyneuropathy, amyloidosis associated with endocrine tumors such as medullary carcinoma of the thyroid with compounds and/or pharmaceutical compositions of the inventions are provided.

Although the methods of the invention may be used in a mammal, for example a human, of any age, in certain examples, the individual is an infant or a child, for example a person under the age of 18, or 16, or 14, or 12, or 10, or 8, or 6, or 5, or 4, or 3, or 2, or 1 years of age. In certain other examples, the individual is an adult, for example an elderly person, for example a person over the age of 50, 55, 60, 65, or 70 years.

Combination Treatment

In one embodiment of any of the above methods, the method further comprises administering a therapeutic or preventive treatment to the subject. In certain aspects, the method comprises administering compounds and/or compositions of the present invention formulated together with one or more antidiabetic agents. Alternatively, the compositions of the present invention comprise a compound of the invention independently formulated with one or more antidiabetic agents i.e., separately formulated.

Suitable antidiabetic agents include, but are not limited to, sulfonylureas, biguanides, glitazones and other PPARγ agonists, α-glucosidase inhibitors, potassium channel antagonists, aldose reductase inhibitors, glucagon antagonists, activators of RXR, activators of PPARα, activators of PPARδ, insulin therapy or other anti-obesity agents. The administration of a composition comprising i) a compound of Formula I, which are PPARγ modulators and known to increase peripheral tissue sensitivity to insulin, with ii) an antidiabetic agent such as insulin therapy, or a stimulator of insulin secretion, and the like, may increase the efficacy of either agent alone. In addition to increased efficacy, the combination therapy of the present invention may allow for a concomitant reduction in the dose of the agents. The combination therapy of a compound of the invention and one or more of another antidiabetic agents (e.g., biguanides, glitazones, RXR ligands, PPARγ agonists, etc.) may result in a reduction in the side effects normally associated with certain antidiabetic agents.

In certain aspects, compounds of the invention are administered in combination with antidiabetic agents that are ineffective for stimulation of insulin secretion or insulin sensitivity, such as α-glucosidase inhibitors, potassium channel antagonists, aldose reductase inhibitors, glucagon antagonists, RXR ligands, PPARα agonists, PPARδ agonists, and anti-obesity agents.

Since the present invention has an aspect that relates to a combination of active ingredients which can be administered separately, the invention also relates to combining separate pharmaceutical compositions in kit form. The kit comprises two separate pharmaceutical compositions: a compound of the present invention or a pharmaceutically acceptable salt and a second compound such as an antidiabetic agent as described above. The kit comprises a container for containing the separate components such as a divided bottle or a divided foil packet, however, the separate components can also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Effective combination amounts for various uses will depend on, for example, the particular antidiabetic agent, the exact inventive compound employed, the manner of administration, the weight and general state of health of the patient, and the judgment of the prescribing physician. In one embodiment, composition or formulation to be administered will contain a quantity of a compound(s) according to Formula I in an amount effective to treat the disease/condition of the subject being treated. The amount of antidiabetic agent will depend in part to the chemical class.

EXAMPLES

The following examples illustrate specific aspects of the instant description. The examples should not be construed as limiting, as the examples merely provide specific understanding and practice of the embodiments and their various aspects.

Materials.

Thioflavin T (ThT) was purchased from Acros Organics (Fair Lawn, N.J.). Lipids [dioleoylphosphatidylglycerol (DOPG) and dioleoylphosphatidylcholine (DOPC)] were purchased from Avanti Polar Lipids, Inc. (Alabaster, Ala.). The 96-well plates (black, w/flat bottom) were bought from Greiner Bio-One (Monroe, N.C.). All of the chemicals were purchased from commercial suppliers and used without further purification. Silica plates (w/UV254, aluminum backed, 200 micron) and silica gel (standard grade, particle size=40-63 micron, 230×400 mesh) for flash column chromatography were purchased from Sorbent Technologies (Atlanta, Ga.). Dry solvents were purchased from Sigma Aldrich (St. Louis, Mich.) or VWR (Bridgeport, N.J.). Ethyl 4-nitro-1H-pyrrole-2-carboxylate, Alkyl iodides, triethylamine (dry), PyBOP (benzotriazol-1-yl-oxytripyrrolidinophosphonium hexafluorophosphate), tert-butyl bromoacetate, tetra-n-butylammonium iodide, trifluoroacetic acid (TFA), and triethylsilane (TES) were purchased from Sigma Aldrich (St. Louis, Mich.). Human islet amyloid polypeptide (IAPP) was purchased from Anaspec (Fremont, Calif.) with >98% purity. $A\beta_{42}$ was used without further purification while IAPP was re-purified using in-house purification method.

Preparation of IAPP.

IAPP (~2 mg) was solubilized in 7 M guanidinium hydrochloride. The solution was filtered (0.2 micron) and transferred to C-18 spin column, washed twice with water (400 μL each) followed by 10% acetonitrile in water, 0.1% formic acid (v/v) and then eluted into 200 μL of 50% acetonitrile in water, 0.1% formic acid (v/v). The concentration of IAPP (oxidized form) was calculated using absorbance measurements at 280 nm ($\varepsilon$=1400 $M^{-1}$ $cm^{-1}$). The IAPP solution was divided into several aliquots (20-50 μL, 1-2 mM), lyophilized, and stored as a white solid at −80° C. Fresh stock solution of IAPP was prepared in water for each experiment.

Example 1: Compound Synthesis and Characterization

A library of N-substituted oligopyrrolamides with varying convex surface functionalities and lengths was synthesized. Briefly, ethyl 4-nitro-2-carboxylate pyrrole was N-substituted with various functionalities by refluxing with the desired alkyl bromide in acetone at 65° C. (FIG. 1A). The N-substituted monopyrroles were then saponified or reduced for coupling purposes (FIG. 1A). The oligopyrrolamides were synthesized by coupling an oligopyrrole-acid and monopyrrole-amine in the presence of PyBOP and DIPEA in DMF under inert atmosphere (FIG. 1A). The acid sensitive tert-butyl oligopyrrolamides were treated with a deprotection conditions (DCM: TFA: TES, 75:20:5, v/v) to afford the final compounds as yellow solids.

TABLE 1

% yield of exemplary compounds according to the invention

| Compound | % yield |
|---|---|
| N-Tert-Butyl ADH-117 | 80 |
| ADH-113 | 86 |
| ADH-113_COOH | 95 |
| ADH-117 | 98 |
| ADH-102 | 91 |
| ADH-102_COOH | 94 |
| N-Tert-Butyl ADH-104 | 88 |
| ADH-104 | 96 |
| ADH-105 | 85 |
| N-Tert-Butyl ADH-101 | 82 |
| ADH-101 | 93 |

General Method for the N-Substitution of Pyrroles.

To a solution of ethyl 4-nitro-1H-pyrrole-2-carboxylate (184 mg, 1 mmol) in acetone (25 mL) were added $K_2CO_3$ (415 mg, 3 mmol) and alkyl iodide (3 mmol), and the reaction started at 65° C. with constant stirring for 12 h. The reaction mixture was then cooled to room temperature and concentrated on a rotary evaporator. The reaction mixture was then partitioned between water (100 mL) and ethylacetate (100 mL), and extracted with ethylacetate (3×100 mL). The organic layer was dried over $Na_2SO_4$ and concentrated on a rotary evaporator. Column chromatography (0 to 25% ethylacetate in hexane, v/v) afforded the desired product as an off white solid (see Table 1, above, for % yield).

General Method for the Reduction of Pyrroles.

To a solution of nitropyrrole (0.3 mmol) in EtOAc (10 mL) was added Pd/C (10% by wt.). The reaction proceeded with constant stirring in the atmosphere of $H_2$ (g) at room temperature. The progress of the reaction was monitored using TLC. The completion of the reaction was confirmed by the disappearance of the starting material. The reaction mixture was filtered, and the filtrate was dried over a rotary evaporator to afford the desired product as a brown oil, which was used in subsequent steps without further characterization.

General Method for the Amide Coupling

To a solution of 6-(O-alkyl/amine/benzyl/carboxylic acid)-5-nitropicolinic acid (0.5 mmol) in dimethylformamide (10 mL, anhydrous) were added PyBOP (1 mmol) and diisopropylethylamine (0.48 mmol), and the reaction was stirred for 20 min. at room temperature. 5-amino-6-(O-alkyl/amine/benzyl/carboxylic acid) picolinic acid (0.4 mmol) in dimethylformamide (10 mL, anhydrous) was added and the reaction mixture was stirred at room temperature for 4 hours in the atmosphere of argon. The reaction solution was poured in water (30 mL) and extracted with ethylacetate (30 mL×3). The volatiles were removed on a rotary evaporator. Column chromatography (0 to 40% ethylacetate in hexane, v/v) afforded the desired product as a yellow solid (see Table 1, above, for % yield).

General Method for the Deprotection of N-Substituted Oligopyrroles

To a solution of N-substituted oligopyrrole (0.05 mmol) in dichloromethane (4 mL) was added triethylsilane (0.25 mL) followed by the addition of trifluoroacetic acid (0.75 mL), and the reaction started with constant stirring. The progress of the reaction was monitored using TLC. The deprotection of the acid sensitive tert-butyl group was confirmed by the disappearance of the starting material. The reaction solution was dried on a rotary evaporator and washed with cold diethyl ether (3×5 mL), which afforded the desired product as a yellow solid (see Table 1, above, for % yield).

Synthesis of N-Tert-Butyl ADH-117

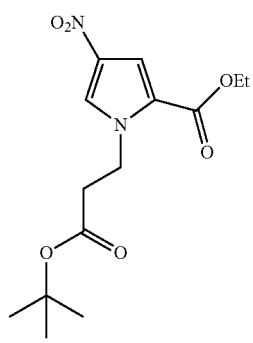 [SMILES: CCOC(=O)c1cc([N+](=O)[O-])cn1CCC(=O)OC(C)(C)C]

To a solution of ethyl 2-(4-nitro-1H-pyrrol-2-yl)-2-oxoacetate (1 gm, 5.43 mmol) in acetone (35 mL), were added K₂CO₃ (2.6 g, 18.5 mmol), tert-butyl 3-bromopropanoate (3.62 mL, 20 mmol), and tetra-n-butylammonium iodide (166.2 mg, 0.5 mmol). The reaction proceeded at 65° C. with constant stirring for 12 hours. The reaction mixture was then cooled to room temperature and concentrated on a rotary evaporator. The reaction mixture was then partitioned between water (100 mL) and ethylacetate (100 mL), and extracted with ethylacetate (3×100 mL). The organic layer was dried over Na₂SO₄ and concentrated on a rotary evaporator. Column chromatography (0 to 30% ethylacetate in hexane, v/v) afforded the desired product as a yellow solid (see Table 1, below, for % yield). ¹H NMR (600 MHz, Chloroform-d) δ 7.78-7.73 (d, J=2.0 Hz, 1H), 7.46-7.43 (d, J=2.0 Hz, 1H), 4.64-4.56 (t, J=6.3 Hz, 2H), 4.36-4.28 (q, J=7.1 Hz, 2H), 2.80-2.74 (t, J=6.3 Hz, 2H), 1.45-1.41 (s, 9H), 1.40-1.36 (t, J=7.1 Hz, 3H). ¹³C NMR (151 MHz, CDCl₃) δ 169.8, 160.0, 135.3, 127.9, 122.2, 113.2, 81.8, 77.2, 77.0, 76.8, 61.0, 46.1, 36.6, 28.0, 14.2. MS-ESI (m/z): calculated for $C_{14}H_{21}N_2O_6$ (M+H): 312.1321, found 312.1321. Anal. Calcd for $C_{14}H_{21}N_2O_6$: C, 53.84; H, 6.45; N, 8.97; O, 30.74. Found: C, 53.90; H, 6.55; N, 8.79. Characterization Data for ADH-113, ADH-117, ADH-102, ADH-101, and Other Exemplary Compounds and Intermediates According to the Invention

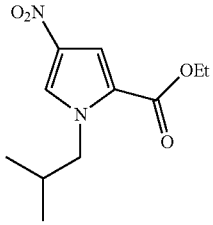

ADH-113

¹H NMR (600 MHz, Chloroform-d) δ 7.60-7.58 (d, J=2.0 Hz, 1H), 7.47-7.43 (d, J=2.0 Hz, 1H), 4.35-4.27 (q, J=7.1 Hz, 2H), 4.18-4.14 (d, J=7.4 Hz, 2H), 2.16-2.05 (dt, J=13.5, 6.8 Hz, 1H), 1.40-1.34 (t, J=7.1 Hz, 3H), 0.94-0.90 (d, J=6.7 Hz, 6H). ¹³C NMR (151 MHz, CDCl₃) δ 160.1, 135.2, 127.2, 122.6, 113.1, 77.2, 77.0, 76.8, 60.9, 57.5, 29.9, 19.7, 14.2, 14.1. MS-ESI (m/z): calculated for $C_{11}H_{16}N_2O_4$ (M+H): 241.1188, found 241.1181. Anal. Calcd for $C_{11}H_{16}N_2O_4$: C, 54.99; H, 6.71; N, 11.66; O, 26.64. Found: C, 55.11; H, 6.79; N, 11.51.

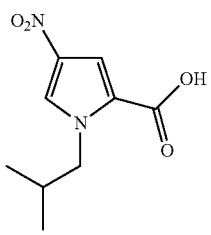

ADH-113_COOH

¹H NMR (600 MHz, DMSO-d₆) δ 13.27-13.07 (s, 1H), 8.28-8.23 (d, J=2.0 Hz, 1H), 7.32-7.28 (d, J=2.1 Hz, 1H), 4.24-4.17 (d, J=7.4 Hz, 2H), 2.09-1.99 (hept, J=6.9 Hz, 1H), 0.86-0.80 (d, J=6.7 Hz, 6H). ¹³C NMR (151 MHz, CDCl₃) δ 161.4, 134.6, 129.4, 123.8, 112.5, 56.4, 29.8, 19.7. MS-ESI (m/z): calculated for $C_9H_{12}N_2O_4$ (M−H): 211.0719, found 211.0717. Anal. Calcd for $C_9H_{12}N_2O_4$: C, 50.94; H, 5.70; N, 13.20; O, 30.16. Found: C, 51.20; H, 5.81; N, 13.11.

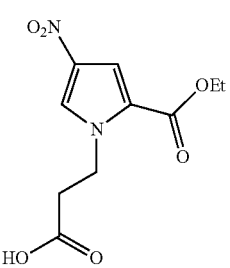

ADH-117

¹H NMR (600 MHz, DMSO-d₆) δ 12.59-12.39 (s, 1H), 8.31-8.17 (d, J=2.1 Hz, 1H), 7.40-7.24 (d, J=2.1 Hz, 1H), 4.62-4.50 (t, J=7.0 Hz, 2H), 4.34-4.21 (q, J=7.1 Hz, 2H), 2.86-2.70 (t, J=7.1 Hz, 2H), 1.36-1.24 (t, J=7.1 Hz, 3H). ¹³C NMR (151 MHz, DMSO) δ 172.3, 159.7, 134.8, 129.6, 122.7, 112.5, 65.4, 61.2, 15.6, 14.5. MS-ESI (m/z): calculated for $C_{10}H_{13}N_2O_6$ (M+H): 257.0774 found 257.0769. Anal. Calcd for $C_{10}H_{13}N_2O_6$: C, 46.88; H, 4.72; N, 10.93; O, 37.47. Found: C, 46.99; H, 4.81; N, 10.81.

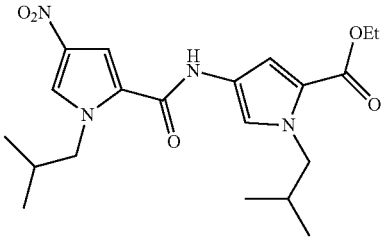

ADH-102

¹H NMR (600 MHz, Chloroform-d) δ 7.61-7.58 (d, J=1.9 Hz, 1H), 7.39-7.34 (d, J=2.1 Hz, 1H), 7.19-7.15 (d, J=1.9 Hz, 1H), 6.88-6.84 (d, J=2.0 Hz, 1H), 4.30-4.25 (q, J=7.2 Hz, 2H), 4.24-4.20 (d, J=7.4 Hz, 2H), 4.12-4.08 (d, J=7.4 Hz, 2H), 2.20-2.06 (m, 2H), 1.37-1.32 (t, J=7.1 Hz, 3H), 0.95-0.89 (dd, J=12.5, 6.7 Hz, 12H). ¹³C NMR (151 MHz, CDCl₃) δ 160.9, 157.4, 135.0, 126.5, 126.0, 120.7, 120.5, 120.0, 108.8, 107.2, 60.0, 57.3, 56.5, 30.2, 30.0, 19.9, 19.7, 14.4. MS-ESI (m/z): calculated for $C_{20}H_{28}N_4O_5$ (M+H): 405.2138 found 405.2133. Anal. Calcd for $C_{20}H_{28}N_4O_5$: C, 59.39; H, 6.98; N, 13.85; O, 19.78. Found: C, 59.55; H, 7.04; N, 13.69.

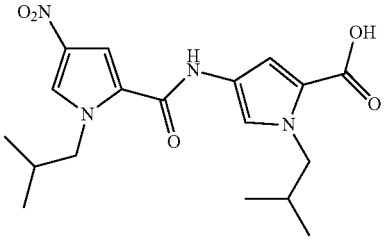

ADH-102_COOH

¹H NMR (600 MHz, DMSO-d₆) δ 12.41-12.01 (s, 1H), 10.53-10.09 (s, 1H), 8.24-8.18 (d, J=2.0 Hz, 1H), 7.61-7.55 (d, J=2.0 Hz, 1H), 7.44-7.39 (d, J=2.0 Hz, 1H), 6.89-6.84 (d, J=2.0 Hz, 1H), 4.29-4.24 (d, J=7.4 Hz, 2H), 4.14-4.08 (d, J=7.3 Hz, 2H), 2.10-2.03 (dq, J=13.8, 7.0, 6.5 Hz, 1H), 2.02-1.94 (m, 1H), 0.85-0.78 (dd, J=6.7, 4.5 Hz, 12H). ¹³C NMR (151 MHz, DMSO) δ 162.2, 157.4, 134.3, 128.4, 126.3, 122.2, 120.5, 119.8, 109.4, 108.6, 56.3, 55.3, 30.4, 29.8, 20.0, 19.8. MS-ESI (m/z): calculated for $C_{18}H_{24}N_4O_5$ (M+H): 377.1825 found 377.1820. Anal. Calcd for $C_{18}H_{24}N_4O_5$: C, 57.44; H, 6.43; N, 14.88; O, 21.25. Found: C, 57.66; H, 6.51; N, 14.75.

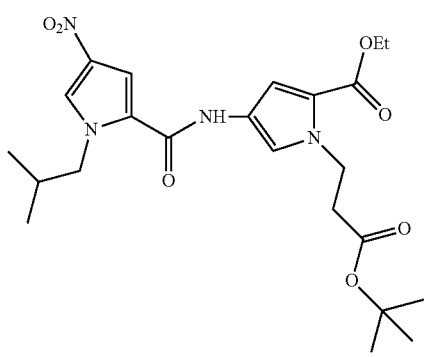

ADH-104

N-Tert-Butyl

¹H NMR (600 MHz, Chloroform-d) δ 7.64-7.60 (s, 1H), 7.60-7.58 (d, J=1.9 Hz, 1H), 7.45-7.41 (d, J=2.1 Hz, 1H), 7.20-7.16 (d, J=1.9 Hz, 1H), 6.88-6.86 (d, J=2.0 Hz, 1H), 4.57-4.50 (t, J=6.9 Hz, 2H), 4.31-4.25 (q, J=7.1 Hz, 2H), 4.24-4.20 (d, J=7.3 Hz, 2H), 2.80-2.68 (t, J=6.9 Hz, 2H), 2.19-2.00 (dt, J=13.5, 6.8 Hz, 1H), 1.45-1.43 (s, 10H), 1.38-1.33 (t, J=7.1 Hz, 3H), 0.94-0.89 (d, J=6.6 Hz, 7H). ¹³C NMR (151 MHz, CDCl₃) δ 170.4, 160.7, 157.4, 135.0, 126.5, 125.9, 121.0, 120.5, 119.7, 109.2, 107.2, 81.1, 60.2, 57.3, 45.2, 37.4, 30.0, 28.1, 19.7, 14.4. MS-ESI (m/z): calculated for $C_{23}H_{32}N_4O_7$ (M+Na): 499.2169 found 499.2160. Anal. Calcd for $C_{23}H_{32}N_4O_7$: C, 57.97; H, 6.77; N, 11.76; O, 23.50. Found C, 58.03; H, 6.80; N, 11.61.

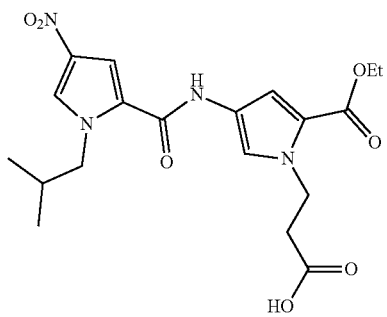

ADH-104

¹H NMR (600 MHz, DMSO-d₆) δ 12.50-12.22 (s, 1H), 10.34-10.21 (s, 1H), 8.24-8.16 (d, J=1.9 Hz, 1H), 7.60-7.54 (d, J=2.0 Hz, 1H), 7.50-7.40 (d, J=2.0 Hz, 1H), 6.99-6.92 (d, J=2.0 Hz, 1H), 4.49-4.43 (t, J=6.9 Hz, 2H), 4.28-4.24 (t, J=7.4 Hz, 2H), 4.25-4.18 (q, J=7.1 Hz, 2H), 2.73-2.65 (t, J=7.0 Hz, 2H), 2.09-2.00 (hept, J=6.9 Hz, 1H), 1.31-1.26 (t, J=7.1 Hz, 3H), 0.86-0.79 (d, J=6.7 Hz, 6H). ¹³C NMR (151 MHz, DMSO) δ 172.7, 160.5, 157.4, 134.4, 128.5, 126.2, 122.7, 120.6, 118.8, 109.5, 108.6, 60.1, 56.3, 44.8, 36.3, 29.8, 19.8, 14.7. MS-ESI (m/z): calculated for $C_{19}H_{24}N_4O_7$ (M+H): 421.1723 found 421.1719. Anal. Calcd for $C_{19}H_{24}N_4O_7$: C, 54.28; H, 5.75; N, 13.33; O, 26.64. Found C, 54.44; H, 5.87; N, 13.19.

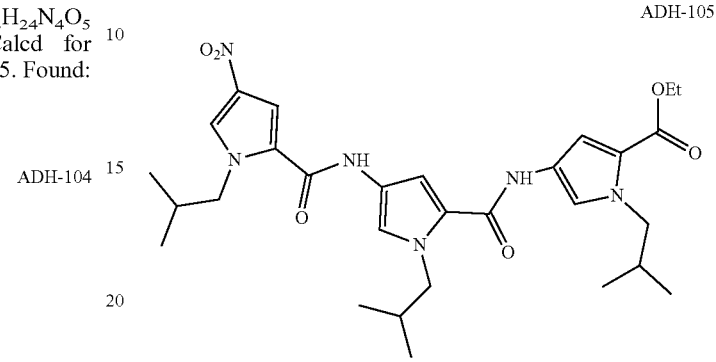

ADH-105

¹H NMR (600 MHz, Chloroform-d) δ 7.64-7.62 (d, J=1.9 Hz, 1H), 7.59-7.55 (s, 1H), 7.50-7.46 (s, 1H), 7.43-7.39 (d, J=2.1 Hz, 1H), 7.22-7.19 (d, J=1.9 Hz, 1H), 7.19-7.15 (d, J=1.9 Hz, 1H), 6.85-6.83 (d, J=2.0 Hz, 1H), 6.74-6.71 (d, J=1.9 Hz, 1H), 4.32-4.27 (q, J=7.1 Hz, 2H), 4.27-4.24 (d, J=7.5 Hz, 2H), 4.22-4.18 (d, J=7.5 Hz, 2H), 4.14-4.10 (d, J=7.3 Hz, 2H), 2.24-2.08 (dddt, J=29.7, 20.6, 13.8, 6.9 Hz, 3H), 1.39-1.36 (t, J=7.1 Hz, 3H), 0.97-0.95 (d, J=6.7 Hz, 6H), 0.94-0.91 (d, J=6.6 Hz, 12H). MS-ESI (m/z): calculated for $C_{29}H_{40}N_6O_6$ (M+H₂O)⁺: 585.3037 found 585.3030. Anal. Calcd for $C_{29}H_{40}N_6O_6$: C, 61.25; H, 7.09; N, 14.78; O, 16.88. Found C, 61.42; H, 7.11; N, 14.74.

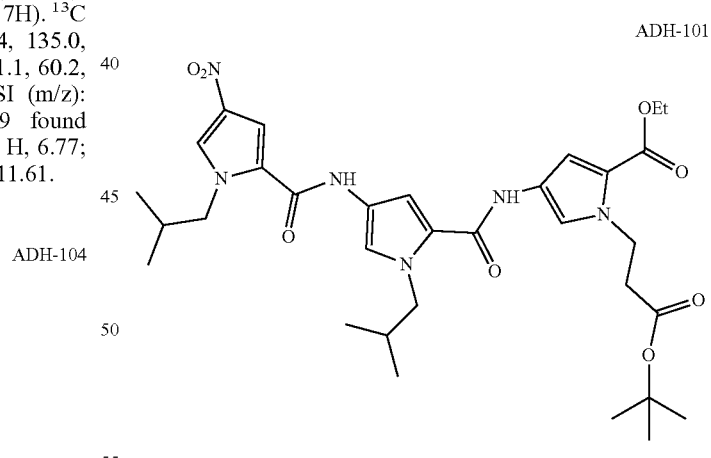

ADH-101

N-Tert-Butyl

¹H NMR (600 MHz, Chloroform-d) δ 7.82-7.71 (s, 1H), 7.65-7.60 (d, J=1.9 Hz, 1H), 7.54-7.49 (s, 1H), 7.49-7.44 (d, J=2.2 Hz, 1H), 7.27-7.23 (d, J=1.9 Hz, 1H), 7.21-7.17 (d, J=1.9 Hz, 1H), 6.88-6.85 (d, J=2.1 Hz, 1H), 6.78-6.73 (s, 1H), 4.58-4.51 (t, J=7.0 Hz, 2H), 4.33-4.28 (q, J=7.1 Hz, 2H), 4.27-4.24 (d, J=7.4 Hz, 2H), 4.20-4.15 (d, J=7.4 Hz, 2H), 2.80-2.73 (t, J=7.0 Hz, 2H), 2.26-2.07 (ddq, J=27.5, 13.8, 6.9 Hz, 2H), 1.48-1.41 (s, 9H), 1.40-1.34 (t, J=7.1 Hz, 3H), 0.99-0.93 (d, J=6.7 Hz, 6H), 0.93-0.90 (d, J=6.7 Hz, 6H). MS-ESI (m/z): calculated for $C_{32}H_{44}N_6O_8$ (M+H):

641.3299 found 641.3297. Anal. Calcd for $C_{32}H_{44}N_6O_8$: C, 59.99; H, 6.92; N, 13.12; O, 19.98. Found C, 60.18; H, 6.99; N, 13.04.

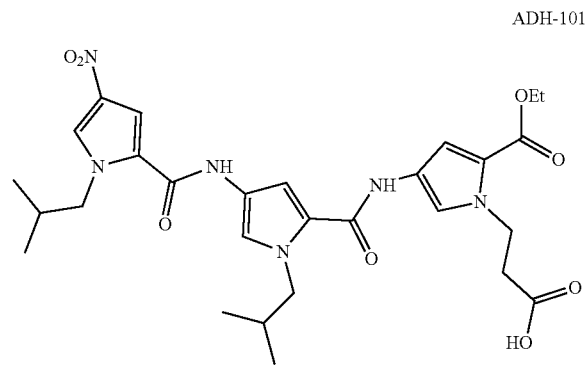 [SMILES: CCOC(=O)c1cc(NC(=O)c2cc(NC(=O)c3cc([N+](=O)[O-])cn3CC(C)C)cn2CC(C)C)cn1CCC(=O)O]

ADH-101

$^1$H NMR (600 MHz, Chloroform-d) δ 7.82-7.71 (s, 1H), 7.65-7.60 (d, J=1.9 Hz, 1H), 7.54-7.49 (s, 1H), 7.49-7.44 (d, J=2.2 Hz, 1H), 7.27-7.23 (d, J=1.9 Hz, 1H), 7.21-7.17 (d, J=1.9 Hz, 1H), 6.88-6.85 (d, J=2.1 Hz, 1H), 6.78-6.73 (s, 1H), 4.58-4.51 (t, J=7.0 Hz, 2H), 4.33-4.28 (q, J=7.1 Hz, 2H), 4.27-4.24 (d, J=7.4 Hz, 2H), 4.20-4.15 (d, J=7.4 Hz, 2H), 2.80-2.73 (t, J=7.0 Hz, 2H), 2.26-2.07 (ddq, J=27.5, 13.8, 6.9 Hz, 2H), 1.48-1.41 (s, 9H), 1.40-1.34 (t, J=7.1 Hz, 3H), 0.99-0.93 (d, J=6.7 Hz, 6H), 0.93-0.90 (d, J=6.7 Hz, 6H). MS-ESI (m/z): calculated for $C_{28}H_{37}N_6O_8$(M+H): 585.2673 found 585.2676. Anal. Calcd for $C_{28}H_{37}N_6O_8$: C, 57.52; H, 6.21; N, 14.38; O, 21.89. Found C, 57.63; H, 6.32; N, 14.34.

Example 2: ThT-Based Kinetic Assay

Figure 8A:
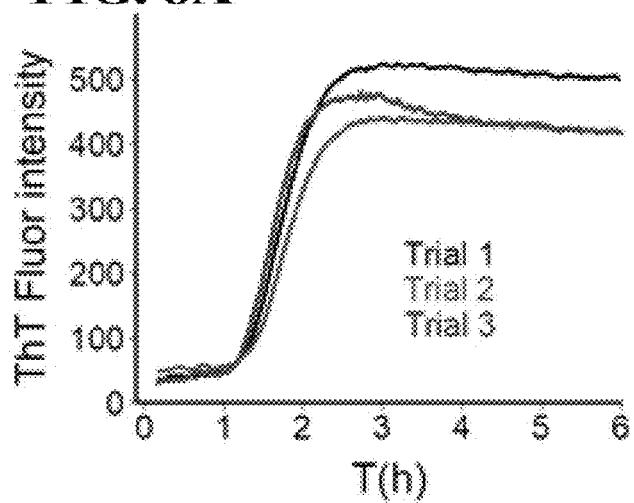
FIGS. 8(A)-8(C) illustrate how the kinetics of IAPP fibrillation were quantified using ThT dye.
Figure 8B:
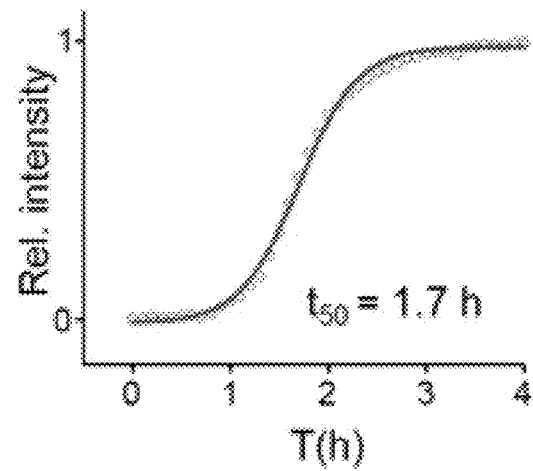
Figure 8C:
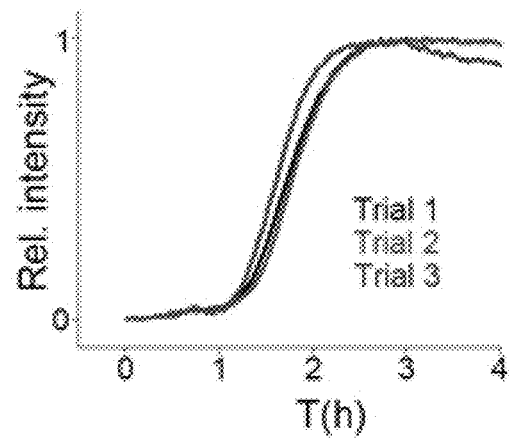

The aggregation kinetics of IAPP was probed using an exogenous reporter, Thioflavin T (ThT), which quantifies the amount of fibers in solution without perturbing the aggregation kinetics of IAPP (see Wolfe, L. S.; Calabrese, M. F.; Nath, A.; Blaho, D. V.; Miranker, A. D.; Xiong, Y. *Proc. Natl. Acad. Sci. U.S.A.* 2010, 107, 16863-16868; Levine, H. *Protein Sci.* 1993, 2, 404-410). As depicted in FIG. 2A, the aggregation kinetics of IAPP resulted in a sigmoidal curve which consists of a lag phase, a growth phase, and a saturation phase where most of the protein is in the amyloid state. The kinetics of IAPP fibrillation was quantified using the reaction midpoint, $t_{50}$, which is the time required to reach 50% fluorescence in the fibrillation reaction (FIG. 8).

Kinetic assays were conducted on a FlexStation 3 Multi-Mode Microplate reader from Molecular Devices (Sunnyvale, Calif.). Experiments were conducted in triplicate in a 96-well plate with a final volume of 200 μL per well. Every measurement was an average of 50 readings. The aggregation of IAPP was initiated by its addition from a stock solution (1 mM in DMSO) to phosphate buffer. The stoichiometry ratio for ThT to IAPP was 0.5:1. Peptide aggregation was monitored by ThT fluorescence ($\lambda_{ex}$=445 nm and $\lambda_{em}$=485 nm). The blank sample contained all the components of the peptide samples except peptide. The sample data were processed by subtracting the blank and renormalizing the fluorescence intensity by setting the maximum value to 1.

Kinetic assays in the presence of the compounds of the invention were conducted under the same conditions. Small molecules were added from a stock solution (1 mM or 10 mM in DMSO) to keep the final concentration of DMSO less than 1.0% (v/v). Small molecules were added to the wells with ThT and buffer and mixed gently with a pipette before adding IAPP. To keep the conditions identical, an equal amount of DMSO was added to the wells with IAPP only reactions. For the aggregation kinetics of $A\beta_{42}$, the peptide was dissolved in 1N NaOH (0.5-1 mM) and vortexed for 2 min. to ensure the complete solubility. The aggregation of 3 μM $A\beta_{42}$ was initiated by addition of peptide from a stock solution (in 1 N NaOH, 0.5-1 mM) to phosphate buffer.

Kinetic profiles were processed using Origin (version 9.1). Kinetic curves were fit using the built-in sigmoidal fit. Each run was fit independently to extract the $t_{50}$ (time required to reach 50% of the maximum fluorescence intensity). Error bars represent standard deviations from the mean of at least three independent experiments.

Figure 5B:
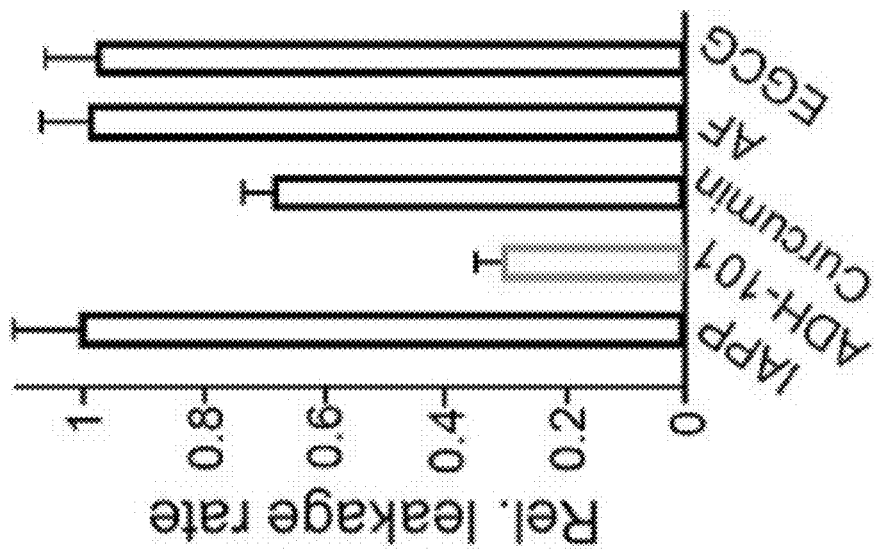
FIGS. 5(A)-5(B) illustrate the effect of ADH-101 on IAPP-induced lipid membrane poration.

As can be seen from the ThT-based kinetic assays depicted by FIGS. 2 and 5, ADH-101, a tripyrrole, was one of the most effective antagonists of IAPP fibrillation under both lipid free and lipid catalyzed conditions (FIG. 2). The $t_{50}$ for IAPP fibrillation was 1.7±0.2 h and 5.8±0.6 h under lipid membrane system and de novo conditions, respectively. At an equimolar ratio, ADH-101 delays the kinetics of lipid catalyzed aggregation of IAPP with a relative $t_{50}$ that is 2.7 fold higher than the control reaction (FIGS. 2A and 2B). ADH-101 completely inhibits IAPP fibrillation at a stoichiometric ratio of 10:1 (ADH-101:IAPP). Under de novo conditions (no lipid membrane), ADH-101 delays the kinetics of IAPP fibrillation with a relative $t_{50}$ that is 4.4 fold higher than the control reaction at an equimolar ratio (FIG. 2B) and completely abolishes IAPP aggregation at fivefold excess (FIG. 2B).

ADH-201, shown below, an analogous tripyridylamide with the same surface functionalities as ADH-101.

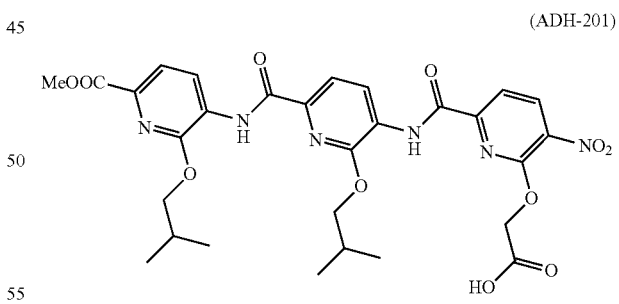

(ADH-201)

ADH-201 is also an effective inhibitor of IAPP aggregation with $t_{50}$=1.4 fold (FIG. 2D), although less effective than ADH-101. ADH-101 ($t_{50}$=2.7 fold) was also better inhibitor than ADM-11 ($t_{50}$=1.9 fold), an oligopyridylamide, and one of the most potent inhibitor reported for IAPP aggregation (FIG. 2D), see Kumar, S.; Birol, M.; Miranker, A. D. Chem. Commun. 2016, 52, 6391-6394.

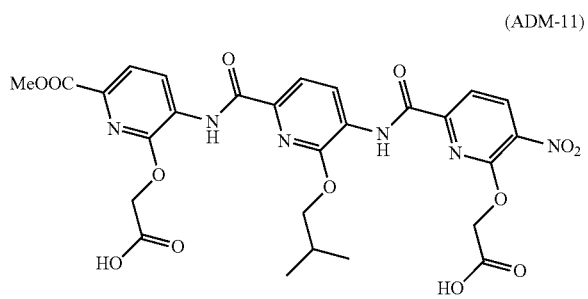 [SMILES: COC(=O)c1ccc(NC(=O)c2ccc(NC(=O)c3ccc([N+](=O)[O-])c(OCC(=O)O)n3)c(OCC(C)C)n2)c(OCC(=O)O)n1]

(ADM-11)

The partition coefficient for ADH-101 and ADM-11 are 2.2 and −0.8 respectively, making the former a better cell penetrating ligand, which is advantageous since one of the proposed mechanisms for IAPP cytotoxicity involves its intracellular colocalization at the mitochondria and impairs β-cell functions.

ADH-101 was also a better inhibitor of IAPP fibrillation than previously reported inhibitors including EGCG, Curcumin, and Acid fuchsin. Under lipid catalyzed conditions, ADH-101 was 2.2, 3.3, and 3.5 fold better inhibitor than Curcumin, EGCG, and Acid Fuchsin.

A range of structurally related pyrroles was tested against the aggregation kinetics of IAPP to assess the specificity of ADH-101 towards IAPP (see FIG. 2C). The monomeric building blocks of ADH-101, ADH-113 and ADH-117 were ineffective in inhibiting IAPP fibrillation. The dipyrroles were weak inhibitors of IAPP fibrillation (FIG. 2C). A tripyrrole, ADH-105, with three N-isobutyl functionalities was moderately effective in delaying the aggregation kinetics of IAPP under lipid free (2.6 fold) and lipid membrane conditions (1.5 fold) at an equimolar ratio. The above results suggest that inhibition of IAPP fibrillation is specific to the functionalities presented on the surface of the oligopyrroles. Taken together, the study implies that the precise location and chemical nature of the side chain functionalities are essential to confer optimum inhibitory activity against IAPP fibrillation.

Figure 9B:
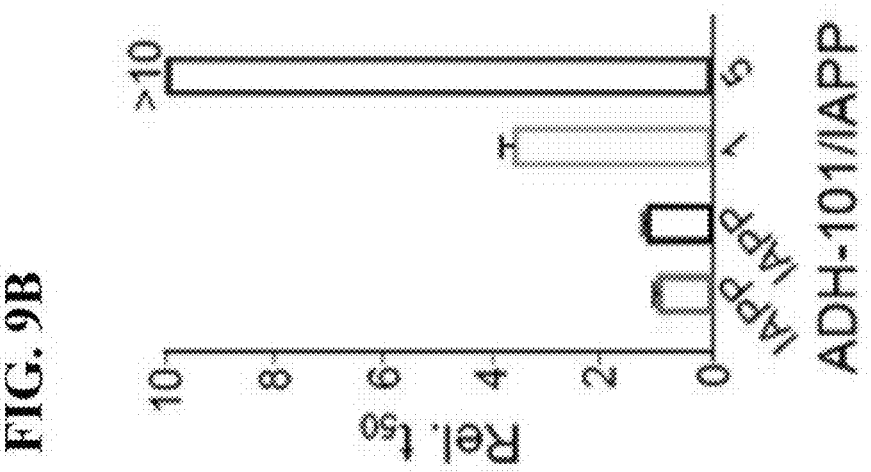
FIG. 9(B) shows the statistical analysis of the amyloid kinetics performed in FIG. 9(A). The error bars reported for the kinetic assays are the standard deviations from three independent experiments.
Figure 9A:
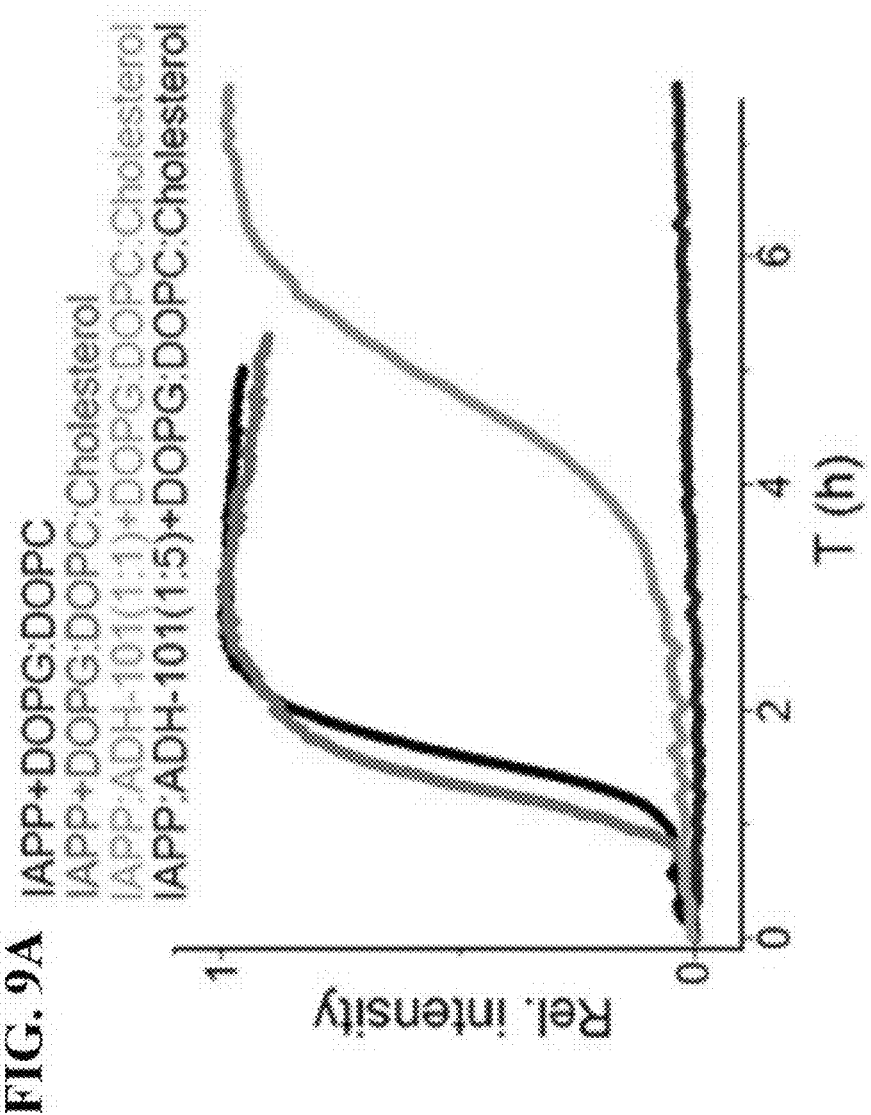
FIG. 9(A) depicts representative normalized amyloid kinetic profiles of 15 μM IAPP in the presence of LUVs (750 μM) and ADH-101 at an equimolar ratio. LUVs were synthesized in the absence and presence of Cholesterol. LUVs without Cholesterol were synthesized using a mixture of DOPG:DOPC (3:7, d=100 nm) and LUVs with Cholesterol were synthesized using a mixture of DOPG:DOPC (3:7, 30% Cholesterol, w/w, d=100 nm).
Figure 10:
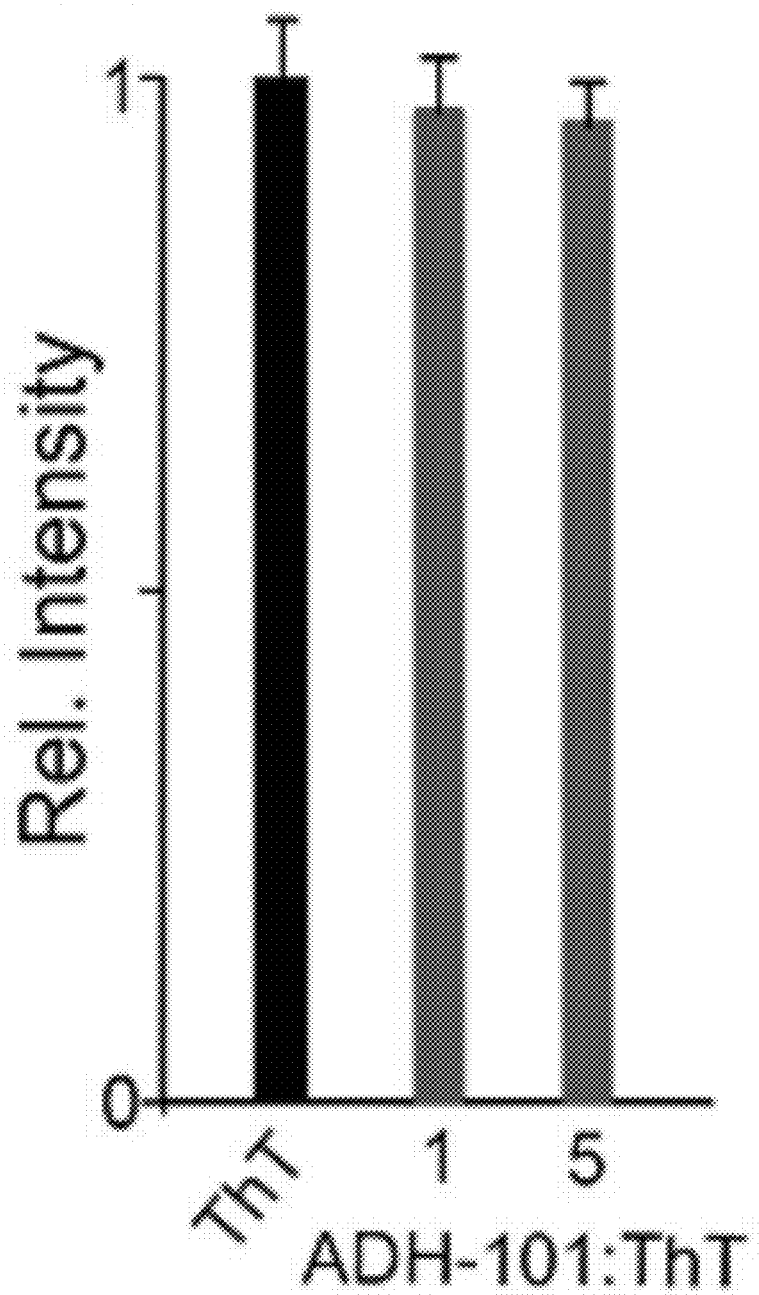
FIG. 10 illustrates the effect of ADH-101 on the fluorescence intensity of ThT. All the conditions are identical as described in FIG. 2 except the protein (IAPP) is absent in FIG. 10. Buffer conditions: 150 mM KCl, 50 mM NaPi, pH 7.4, [ThT]=2 μM, [ADH-41]=2 and 10 μM.

ThT amyloid assays under the more physiological conditions of cholesterol-containing LUVs (LUVs, DOPG:DOPC, 1:1, 30% cholesterol, d=100 nm) more closely matching mammalian plasma cell membranes (30-50 mol %), were also conducted. The $t_{50}$ for 15 μM IAPP in the presence of LUVs (LUVs, DOPG:DOPC, 1:1, 30% cholesterol, d=100 nm) was 1.25±0.2 h (FIG. 9). ADH-101 was equally effective in inhibiting IAPP fibrillation as it delayed the amyloid kinetics by a factor of 3.6 at an equimolar ratio (FIG. 9). Clearly, ADH-101 is a potent inhibitor of IAPP fibrillation under a range of conditions including de novo, lipid membranes, and membranes with cholesterol. Under identical conditions (without IAPP), no significant change in the intensity of ThT was observed in the presence of ADH-101, which suggests that no interaction occurs between ADH-101 and ThT (FIG. 10). As shown above, ADH-101 inhibits the oligomerization of IAPP.

Example 3: Seed-Catalyzed Kinetic Assay

Seeds of IAPP were prepared by incubating 100 μM of IAPP in phosphate buffer at room temperature and aged for 24 hours. The formation of fibers was confirmed by TEM and ThT stain before storage at −20° C. until use. For the seed catalyzed aggregation kinetics of IAPP, 10% (based on the monomeric IAPP, v/v) seeds were added with ThT in phosphate buffer to the 96-well plate. The aggregation was initiated by the addition of fresh IAPP followed by gentle mixing. Kinetic assays in the presence of the compounds of the invention were conducted under the same conditions except that the compounds were added from a stock solution (1 mM or 10 mM in DMSO) to keep the final concentration of DMSO less than 1.0% (v/v).

Figure 4:
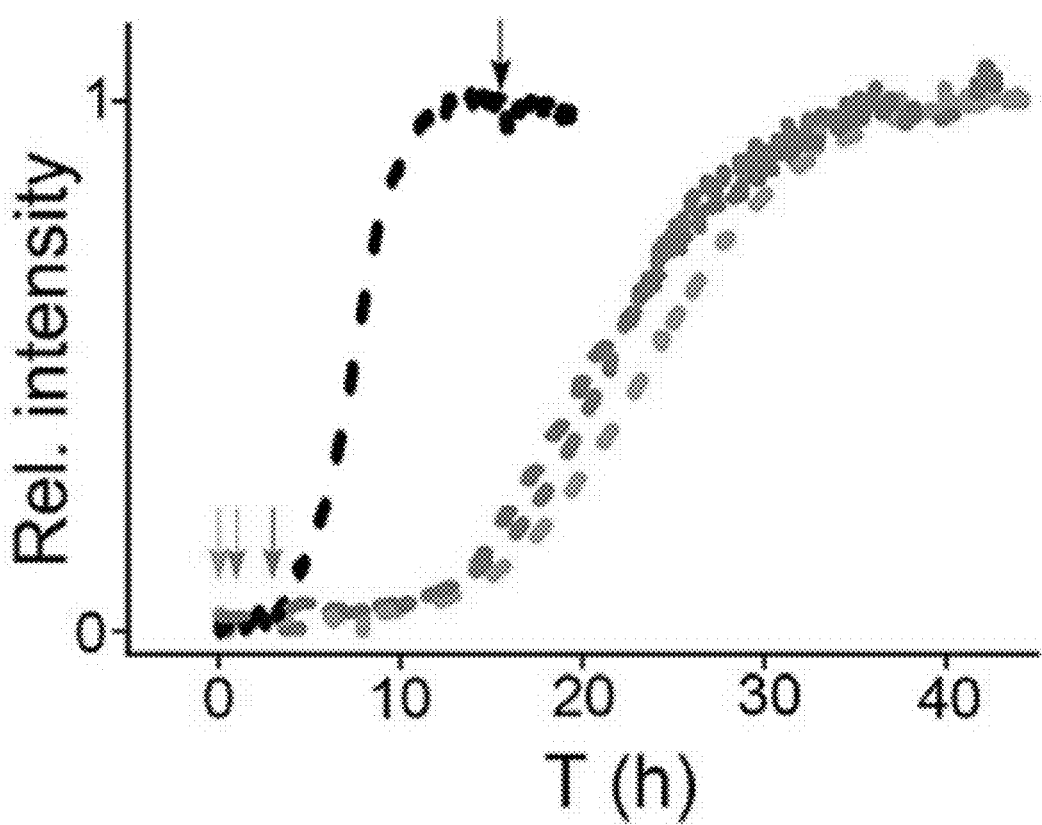
FIG. 4 illustrates inhibition of IAPP amyloid formation by ADH-101 when ADH-101 is added during the lag phase. Representative kinetic profiles of 15 μM IAPP in the absence and presence of ADH-101 at an equimolar ratio. The arrows represent the time of addition of ADH-101 during the kinetic reaction of IAPP fibrillation. ADH-101 was added at 0, 1, 3, and 15 h indicated by orange, green, violet, and black arrows, respectively. Buffer: 50 mM NaPi, 150 mM KCl, pH 7.4.
Figure 13A:
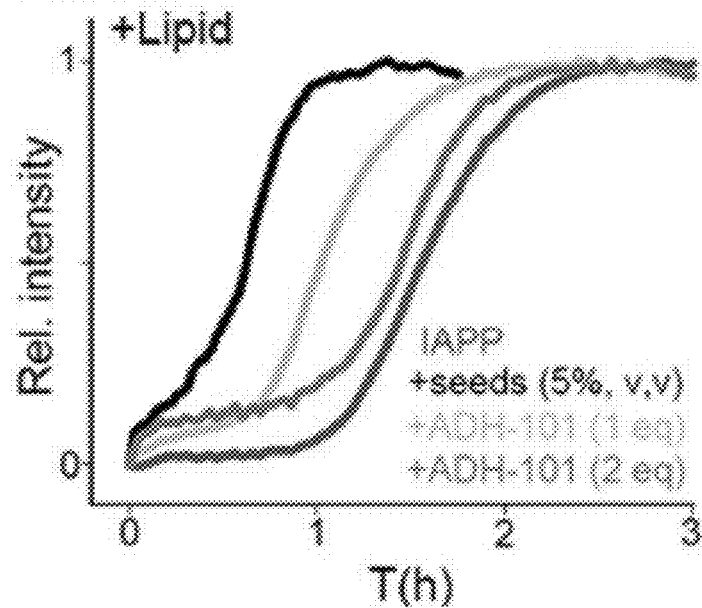
FIGS. 13(A)-13(D) illustrate the dose dependent effect of ADH-101 on the seed catalyzed aggregation kinetics of IAPP under lipid membrane system.
Figure 13B:
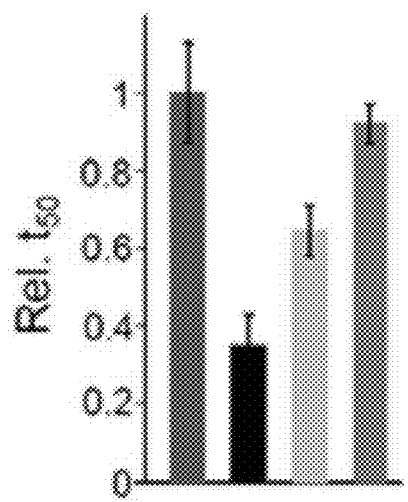
Figure 13C:
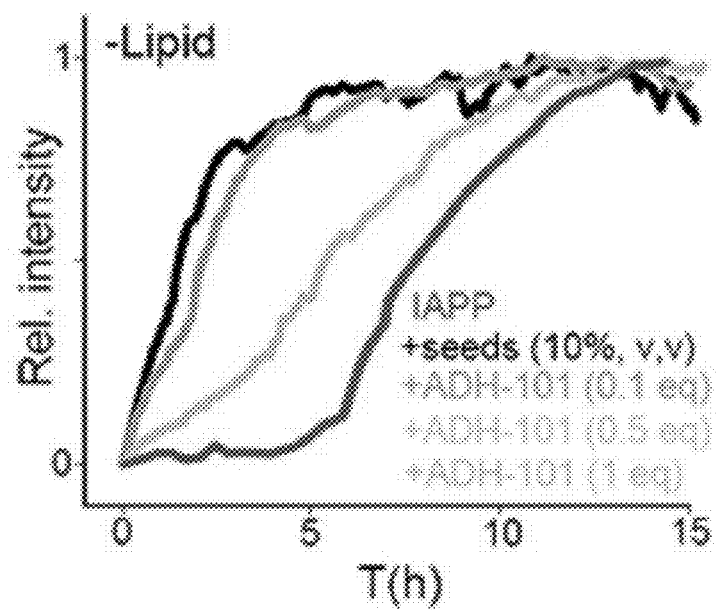
Figure 13D:
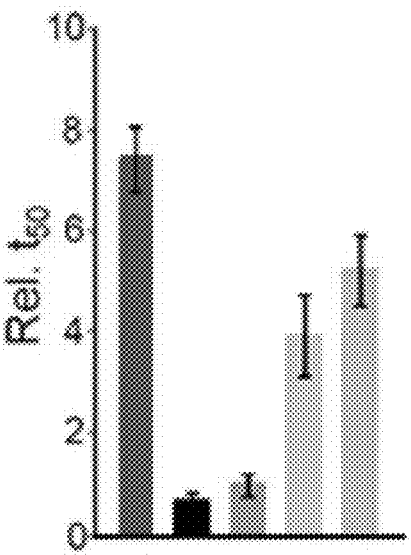

The effect of ADH-101 on preformed IAPP oligomers has been investigated. ADH-101 was added during the lag phase of IAPP amyloid kinetics at 1 h and 3 h at an equimolar ratio (IAPP:ADH-101, 1:1, 10 μM IAPP). In comparison to premixed incubation of ADH-101 with IAPP (t=0 h), ADH-101 was equally effective in inhibiting IAPP fibrillation when added during the lag phase at 1 h and 3 h (FIG. 4). Additionally, ADH-101 has no effect on IAPP amyloid fibers. No change in ThT fluorescence intensity was observed when ADH-101 added to the fibers (FIG. 4, black arrow). ADH-101 presumably disrupts the oligomerization and consequently inhibits IAPP fibrillation. ADH-101 is an effective antagonist of the elongation processes that can be directly seen by using preformed fibers in the aggregation reaction of IAPP. The kinetics of IAPP fibrillation is dominated by the secondary nucleation which is reflected in the disappearance of the lag phase (FIG. 13). The $t_{50}$ for the seed catalyzed (5%, v/v) aggregation kinetics of 15 μM IAPP (lipid membrane, DOPG:DOPC, 3:7, 750 μM) is 0.55±0.13 h which is ~2.3 fold faster than the de novo conditions ($t_{50}$=1.55±0.20 h, FIGS. 13A and 13B). ADH-101 delays the seed catalyzed fibrillation by a relative $t_{50}$ that is 1.8 fold and 2.6 fold at stoichiometric ratios of 1:1 and 2:1 (ADH-101:IAPP), respectively (FIGS. 13A and 13B). The $t_{50}$ for the seed catalyzed (10%, v/v) aggregation of 15 μM IAPP is 0.86±0.19 h, which is ~10 fold faster than the de novo conditions ($t_{50}$=8.7±0.8 h, FIGS. 13C and 13D). ADH-101 retards the seed catalyzed aggregation kinetics of IAPP by factors of 1.4, 5.4, and 7.1 at stoichiometric ratios of 1:0.1, 1:0.5, and 1:1 (IAPP:ADH-101), respectively (FIGS. 13C and 13D). It is postulated that ADH-101 modulates IAPP conformation and attenuates its ability for oligomerization and fibrillation.

Example 4: Preparation of Large Unilamellar Vesicles (LUVs)

The membrane model system selected for the amyloid assays is a mixture of DOPG (dioleoylphosphatidylglycerol) and DOPC (dioleoylphosphatidylcholine) at 3:7 molar ratio, which mimics physiological conditions (Ono, K.; Condron, M. M.; Teplow, D. B. *Proc. Natl. Acad. Sci. U.S.A.* 2009, 106, 14745-14750). The lipid catalyzed aggregation of IAPP was initiated by adding freshly prepared 15 μM IAPP (1 mM stock solution in DMSO) to the phosphate buffer (50 mM NaPi, 150 mM KCl, pH 7.4) containing 15 μM ThT and 750 μM of unilamellar liposomes (LUVs, DOPG:DOPC, 3:7, d=100 nm).

LUVs were prepared using dioleoylphosphatidylglycerol (DOPG) and dioleoylphosphatidylcholine (DOPC) at stoichiometric ratio of 3:7 (DOPG:DOPC). The solution of DOPG and DOPC (6 mg and 14 mg) in chloroform (10 mg/L) was mixed, dried over a stream of argon (g) for 2 hours, and then lyophilized for 12 hours (0.1×10⁻³ bar). The solid was rehydrated in 1 mL phosphate buffer for 30 min. The turbid solution (6 mg:14 mg, 3:7, DOPG:DOPC) was then extruded (21 times) through 100 nm diameter filters (Whatman, GE Healthcare, Marlborough, Mass.). The concentration of the phospholipid content in the extruded material was confirmed by calculating total phosphorus using total phosphate assay as described in Chen, P. S.; Toribara, T. Y.; Warner, H. *Anal. Chem.* 1956, 28, 1756-1758.

Example 5: Transmission Electron Microscopy (TEM) Analysis

IAPP (10 µM) was incubated in phosphate buffer in the absence and presence of ADH-101 at equimolar ratio for 12 hours. Aliquots of these samples were then applied to glow-discharged carbon-coated 300-mesh copper grids for 2 min and dried. Grids were negatively stained with uranyl acetate (2%, w/v) and dried. Micrographs of grids were examined on a Phillips CM12 Cryoelectron Microscope equipped with Gatan 4 k×2.7 k CCD camera at 120-kV accelerating voltage.

Figure 11:
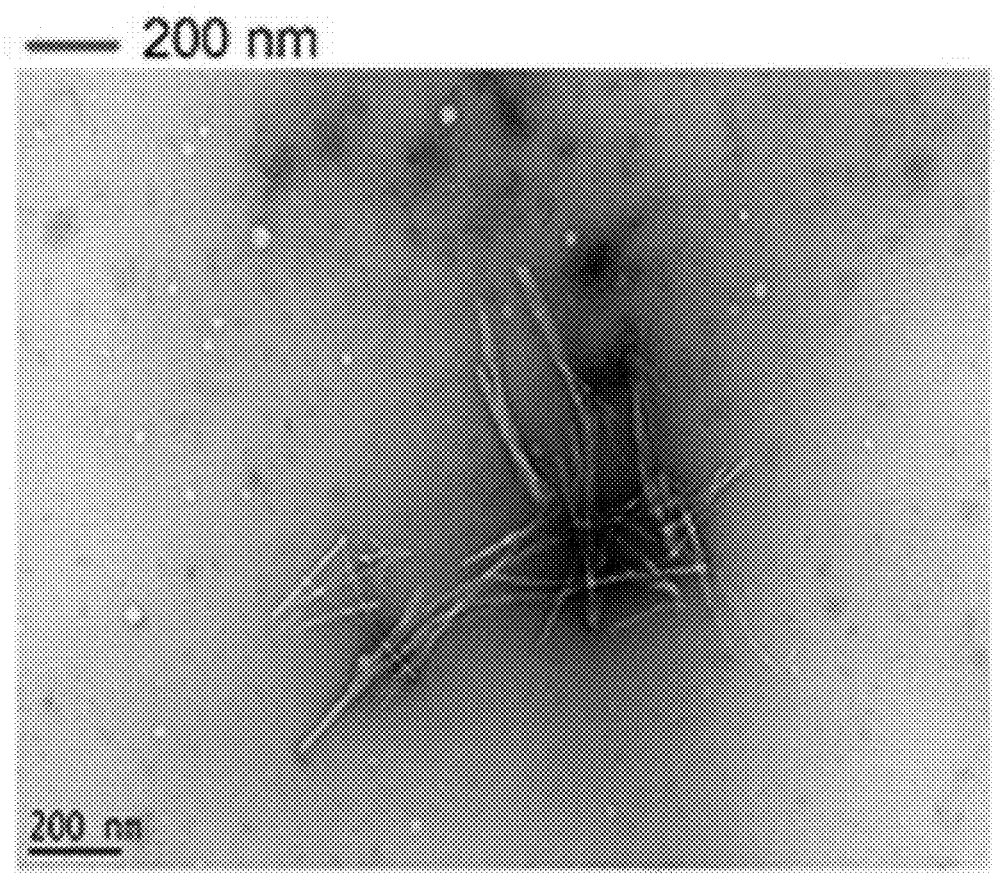
FIG. 11 is a visual analysis of the effect of ADH-101 on the kinetics of IAPP fibrillation using TEM. TEM image of 10 μM IAPP in the presence of ADH-101 at an equimolar ratio after 24 hours. Buffer conditions: 150 mM KCl, 50 mM NaPi, pH 7.4.

Transmission electron microscopy (TEM) was employed to validate the results from ThT assays. The negatively stained TEM image of 10 µM IAPP after 12 hours of incubation was rich in fibers (FIG. 2F); however, no formation of fibers was observed in the presence of ADH-101 at an equimolar ratio after 12 hours (FIG. 2G). The formation of amorphous fibers was observed for ADH-101-IAPP solution after 24 h of incubation (FIG. 11). These results imply that ADH-101 inhibits the aggregation kinetics by modulating the prefibrillar structures of IAPP.

Example 6: Circular Dichroism (CD) Spectroscopy

A freshly prepared stock solution of IAPP (500 µM in water) was diluted to 15 µM in phosphate buffer for CD measurements. The spectra of IAPP were recorded at 0.5 nm intervals from 190 to 260 nm with an averaging time of 10 sec. and an average of three repeats on an Aviv Stopped Flow CD Spectropolarimeter (Model 202SF). Spectra were recorded using the identical method as described above. ADH-101 was added to the solution of IAPP at an equimolar ratio. The CD spectra of lipid catalyzed IAPP kinetics were recorded under the same conditions with the addition of DOPG:DOPC (3:7, 750 µM, d=100 nm).

Circular dichroism was employed to monitor the effect of ADH-101 on the conformation of IAPP. The time dependent CD spectra of 15 µM IAPP in the absence of the inventive compound revealed the expected structural transition from a random coil conformation to a β-sheet conformation characterized by a minima around 220 nm within 8 hours (FIG. 3A). In marked contrast, no β-sheet conformation was observed in the presence of ADH-101 at an equimolar ratio after 8 hours (FIG. 3B).

Figure 3B:
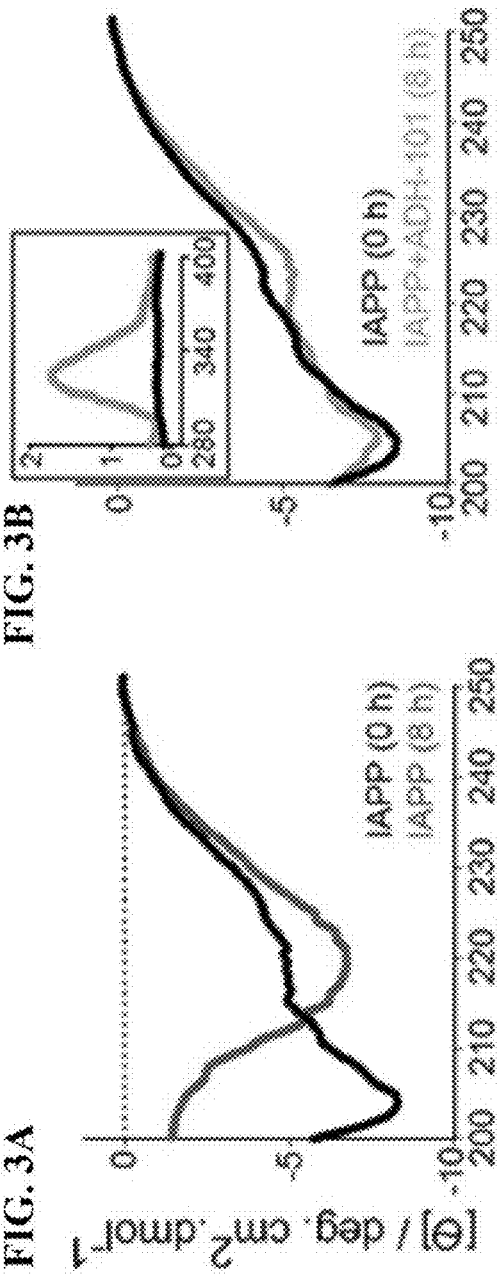
Figure 3C:
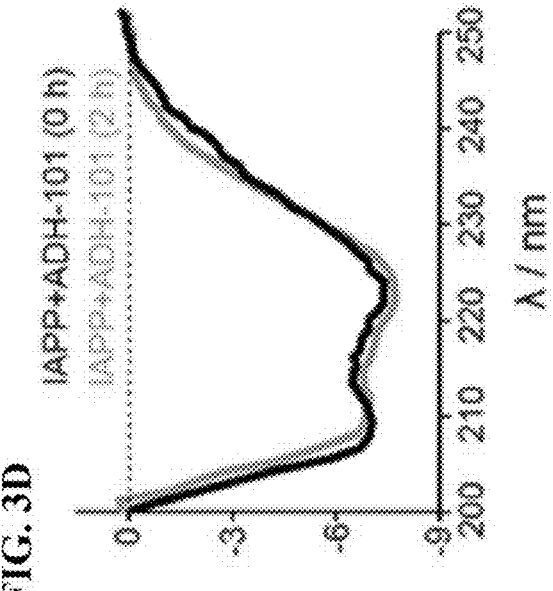
Figure 3D:
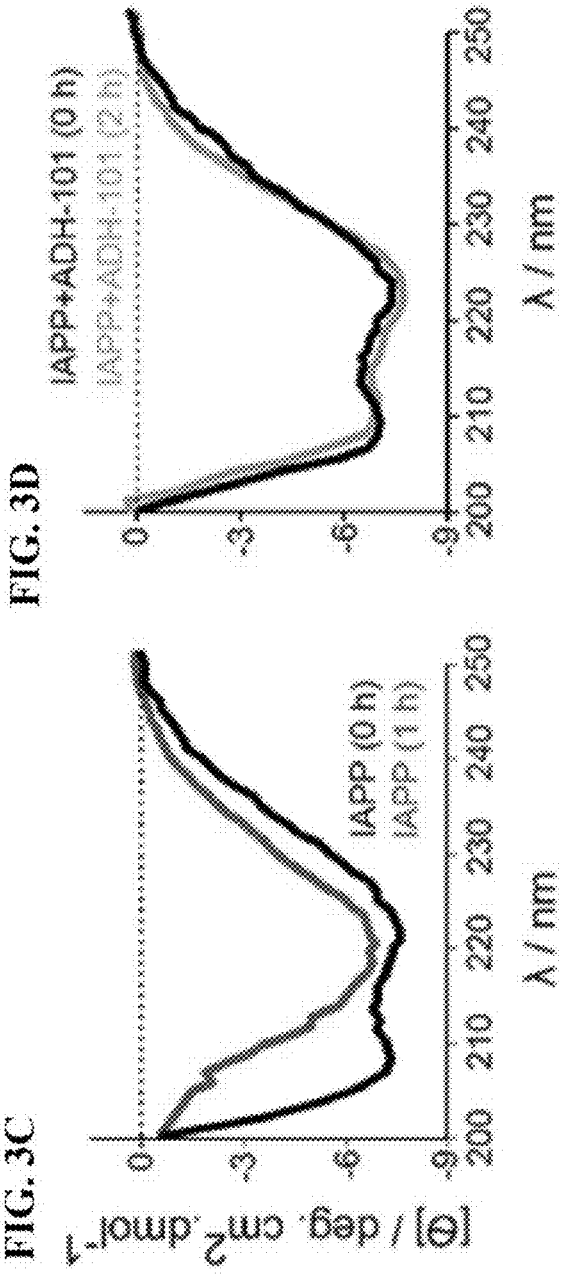

Under lipid membrane conditions (600 µM, DOPG:DOPC, 3:7, 100 nm), 15 µM IAPP exhibits α-helical structure characterized by two minima at ~208 and ~222 nm in the CD spectrum (FIG. 3C). The conformation of IAPP switches from an α-helix to β-sheet in 1 hour (FIG. 3C). In marked contrast, IAPP stays in an α-helical state after 1 hour in the presence of ADH-101 at an equimolar ratio (FIG. 3D). A characteristic CD signal arises at the wavelength around 340 nm contributed by polyamides when they bind in the minor groove of DNA duplexes. No CD signal was detected for ADH-101 alone; however, a positive induced CD signal was observed when ADH-101 was incubated with IAPP at an equimolar ratio (FIG. 3B, inset). CD data suggests that ADH-101 induces secondary structure in IAPP by altering the conformation of IAPP.

As the above data demonstrate, ADH-101 surprisingly and unexpectedly induces an α-helical conformation in IAPP (FIG. 3B). Without wishing to be bound by any theory, it is postulated that ADH-101 alters the conformation of IAPP, which modulates its oligomerization and/or fibrillation properties.

Example 7: Photo-Induced Cross-Linking of Unmodified Proteins (PICUP) SDS-PAGE Gel The effect of ADH-101 on the oligomerization of IAPP was evaluated using performance photo-induced cross-linking of unmodified proteins (PICUP) SDS-PAGE-silver staining as described in Ono, K.; Condron, M. M.; Teplow, D. B. *Proc. Natl. Acad. Sci. U.S.A.* 2009, 106, 14745-14750 (FIG. 2E). IAPP was incubated in a buffer in the presence and absence of ADH-101 at an equimolar ratio, and the solutions were then treated with the cross-linking agent at various time intervals (FIG. 2E). IAPP forms oligomers of varying sizes as a function of time (FIG. 2E, Lane i-iv). In marked contrast, ADH-101 completely inhibits the formation of large aggregates up to 300 min (FIG. 2E, Lane vi-x). Without wishing to be bound by any theory, it is postulated that ADH-101 forms a complex with monomeric IAPP and abolishes the oligomerization of IAPP.

Example 8: Liposome Leakage Assay

Figure 5A:
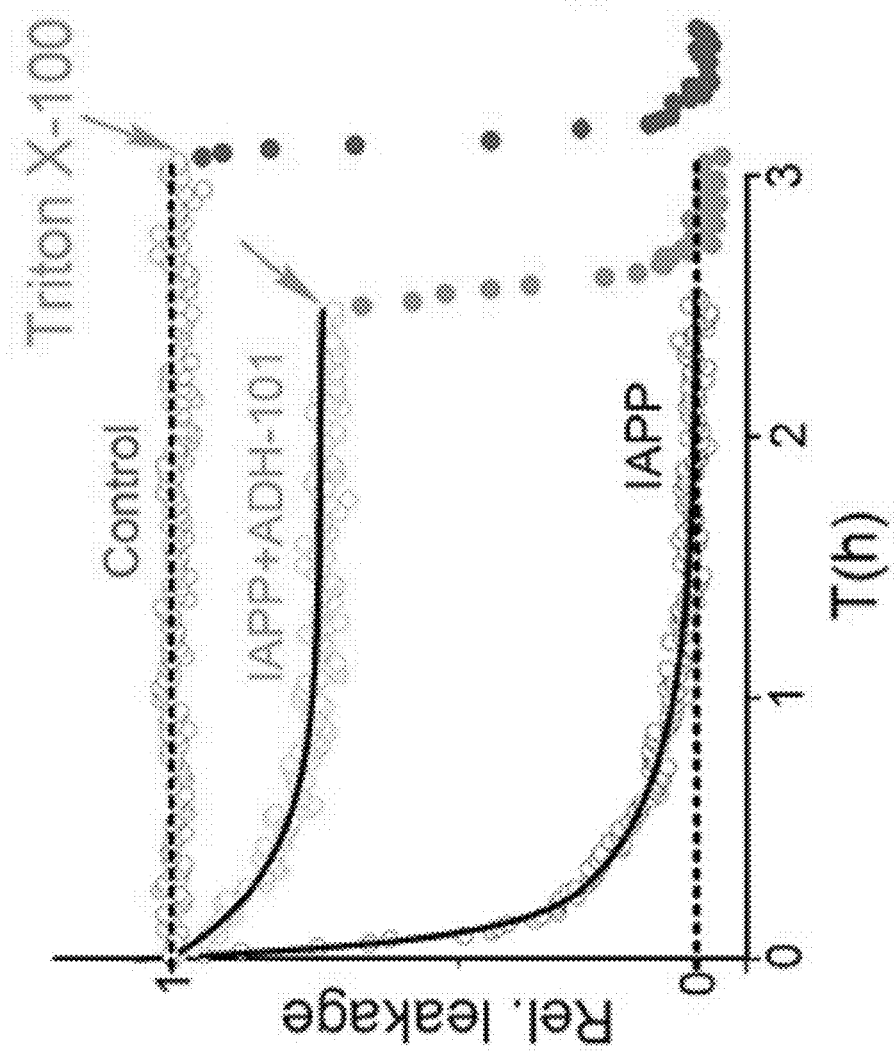

Colocalization of IAPP at the mitochondrial membrane and the subsequent membrane poration is considered to be one of the potential contributors to β-cell toxicity. Therefore, a liposome leakage assay could serve as a surrogate marker for IAPP induced cytotoxicity (see Last, N. B.; Miranker, A. D. *Proc. Natl. Acad. Sci. U.S.A.* 2013, 110, 6382-6387; and Last, N. B.; Rhoades, E.; Miranker, A. D. *Proc. Natl. Acad. Sci. U.S.A.* 2011, 108, 9460-9465). A previously reported fluorescein-based liposome leakage assay was employed to test the effect of ADH-101 on membrane associated α-helical intermediates of IAPP. Briefly, fluorescein-dextran conjugate (MW=70 kDa) was encapsulated in unilamaller extruded lipid vesicles (DOPG:DOPC, 3:7, d=100 nm). The size of fluorescein-dextran conjugate allows it to stay inside the lipid vesicles during IAPP mediated membrane poration. The leakage kinetics was probed by the quenching of fluorescence using a fluorescent quencher, DPX (p-xylene-bis-pyridinium iodide bromide). The kinetic profiles of leakage are single exponential with a decrease in fluorescence as a function of time. The leakage reaction was initiated by introducing 200 µM liposome into a solution of 4 µM IAPP and 6 mM of DPX. The introduction of the excess ionic concentration by DPX was counterbalanced by adjusting the buffer concentration. The kinetics of the leakage mediated by IAPP yielded a single exponential profile with a leakage rate of $7.3 \pm 1.1 \times 10^{-3}$ s$^{-1}$ (FIG. 5A).

Figure 14:
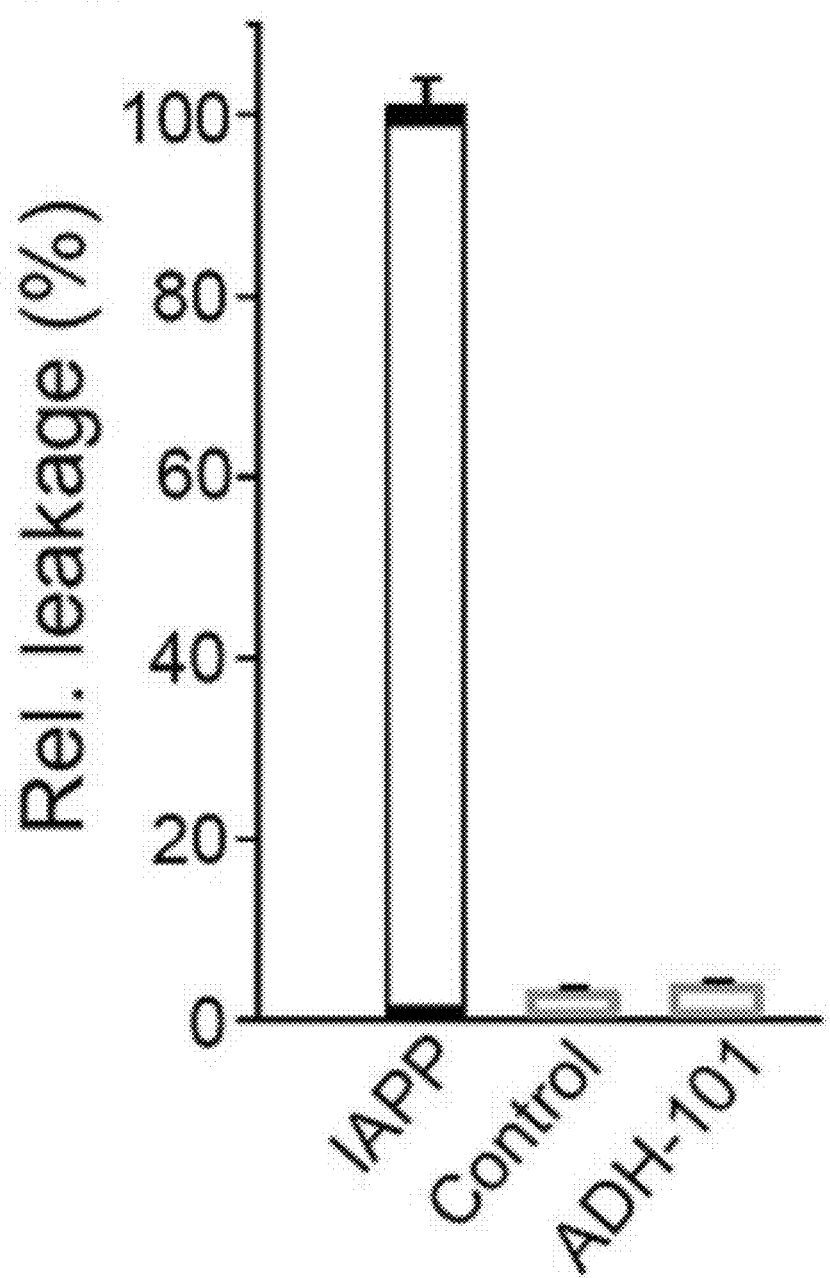
FIG. 14 shows the effect of ADH-101 on the liposome leakage. A sample of 4 μM of ADH-101 in buffer was assayed in our leakage assay conditions (see Example 8). For reference, leakage induced by 4 μM IAPP and by the control (buffer only) is also shown. All kinetic experiments were conducted at least in triplicate with errors reported as standard deviations (SD).

The kinetics of liposome leakage induced by IAPP was monitored on QuantaMaster C-61 fluorescence spectrometer (Photon Technology International, Edison, N.J.) at 25° C. The excitation and emission were observed at 480 nm and 526 nm respectively with 3 nm slit widths. The stock solution of IAPP used in the measurements was kept in water at a concentration of 1 mM. The stock solution of water soluble quencher, DPX (p-xylene-bis-pyridinium bromide) was prepared in buffer (100 mM KCl, 50 mM NaPi, pH 7.4) at a concentration of 100 mM. The small molecules used in the leakage assay were dissolved in DMSO with a concentration range of 10-20 mM. The final concentration of dye encapsulating liposome, DPX, human IAPP, and small molecules were 200, 6000, 4, and 4 µM respectively. The final buffer concentration was corrected using higher concentration of buffer to keep the osmolality balanced. The final concentration of DMSO used in the assay was less than 0.4%. The negative control (no leakage) sample contained everything except IAPP. For positive control (100% leakage), the negative control sample was treated with Triton X-100 (Sigma-Aldrich, St. Louis, Mo.). To determine the leakage rate constant, first the fluorescence was normalized and corrected by subtracting it from normalized fluorescence of control reaction. The corrected fluorescence was fit using equation given below (using Origin 9.1). All the experiments were performed in triplicate and the error values presented are standard deviations.

$$a*\exp(-b*x)+c \qquad (2)$$

a=amplitude from 100% unleaked to 0% leaked
c=final fraction of unleaked liposome
y=change in fluorescence
b=leakage rate constant ADH-101 retards the kinetics of IAPP-induced lipid membrane leakage. The leakage rate of 4 µM IAPP in the presence of ADH-101 was ~3.5 times slower than the control reaction (IAPP only, FIGS. 4A, 4B). The rank order for delaying the leakage kinetics was ADH-101>Curcumin>EGCG≥AF. ADH-101 alone did not have any effect on the integrity of the liposomes (FIG. 14). The ThT assays under our conditions demonstrate that Curcumin, EGCG, and AF exhibit moderate inhibition capacity towards IAPP fibrillation however, they were unable to effect IAPP induced liposome leakage (FIG. 4B). It is not surprising as the antagonist activity of EGCG stems, at least in part, from the remodeling of IAPP fibers. 31, 32 Curcumin moderately delays IAPP mediated leakage kinetics (FIG. 4B). It has been reported that Curcumin acts as an antagonist by disintegrating α-helix conformation of IAPP which leads the modulation of IAPP self-assembly (see Sparks, S.; Liu, G.; Robbins, K. J.; Lazo, N. D. *Biochem. Biophys. Res. Comm.*, 2012, 422, 551-555). As a result, its effect on IAPP mediated leakage is not surprising. Collectively, the CD and leakage data suggest that the ADH-101 induced conformation in IAPP is not leakage competent. IAPP-mediate membrane poration is an upstream event and is considered to be one of the main culprits in inducing cytotoxicity in pancreatic β-cells.

Example 9: Cell Culture

For cell toxicity assays, Rat insulinoma cells (RIN-m) were as they are considered to be a good model for pancreatic β-cells (see Huang, C.; Lin, C.; Haataja, L., Gurlo, T., Butler, A. E., Rizza, R. A., and Butler, P. C. *Diabetes*, 2007, 56, 2016-2027). Rat insulinoma RIN-m cells (ATCC, Manassas, Va.) were cultured in RPMI medium supplemented with 10% fetal bovine serum, 1% penicillin/streptomycin, 100 mM sodium pyruvate, and 50 mM β-mercaptoethanol (Life Technologies, Carlsbad, Calif.) at 37° C. and 5% $CO_2$. Upon reaching ~95% confluence, cells were washed with phosphate buffered saline (VWR, Radnor, Pa.), split using 0.25% Trypsin-EDTA (Life Technologies), and plated in clear 96-well plates (Corning, Glenview, Ill.) for cell viability assays.

Example 10: Cell Viability

Since ADH-101 effectively inhibits liposome leakage, its effect on IAPP mediated cytotoxicity was investigated.

Cell viability was measured using the CellTiter Blue (CTB, Promega, Madison, Wis.) fluorescence-based assay. Cells were plated at a density of 20,000 cells per well in 96 well plates. After 48 h of incubation at 37° C. and 5% $CO_2$, cells were washed with 100 µL of PBS. ADH-101 and hIAPP were pre-mixed in 1×PBS (ThermoFisher, Waltham, Mass.) for 5 min and added to cells with complete RPMI growth medium. Cells were incubated for an additional 48 h. 20 µL of CellTiter Blue reagent was added to each well and incubated for 2.5-3.5 h. Fluorescence of the dye was measured on a FlexStation3 microplate reader (Molecular Devices, Sunnyvale, Calif.). Positive control wells contained 10% DMSO, whereas negative control wells contained water and 0.3% DMSO to account for the peptide and ADH-101 vehicles, respectively. Percent viability was calculated as per the following equation:

$$\% \text{ Viability}=100*[(<S>-<P>)/(<N>-<P>)]$$

Where <S>, <P>, and <N> are the average fluorescence intensities of the sample, positive control, and negative control, respectively.

Figure 6:
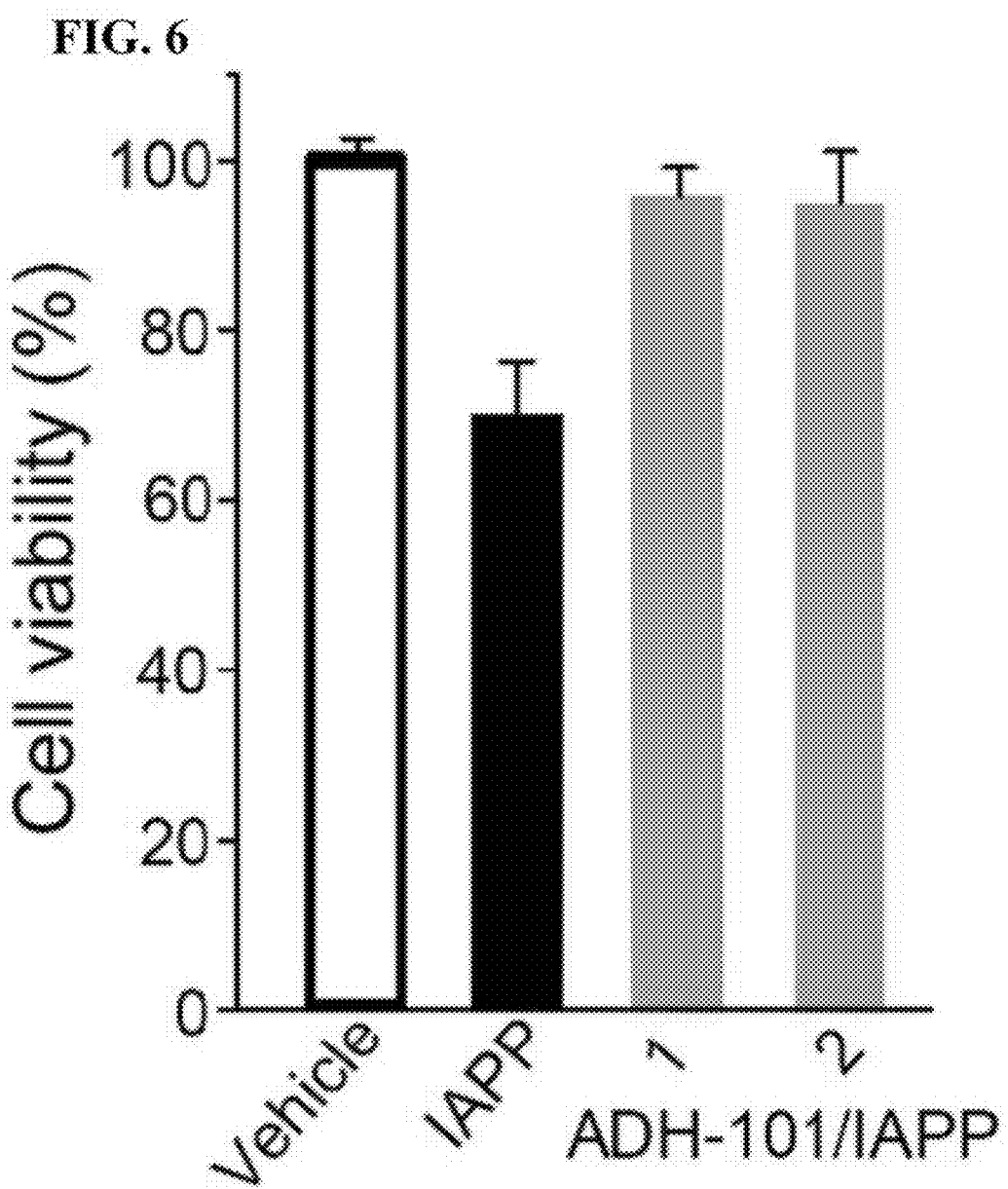
FIG. 6 illustrates the inhibition of IAPP-mediated cytotoxicity in rat insulinoma cells by ADH-101. Statistics of cell viability of 6 μM IAPP in the absence and presence of ADH-101 at the indicated molar ratios'. Error bars reflect variability across 4-8 technical replicates within a single execution of the assay.
Figure 15:
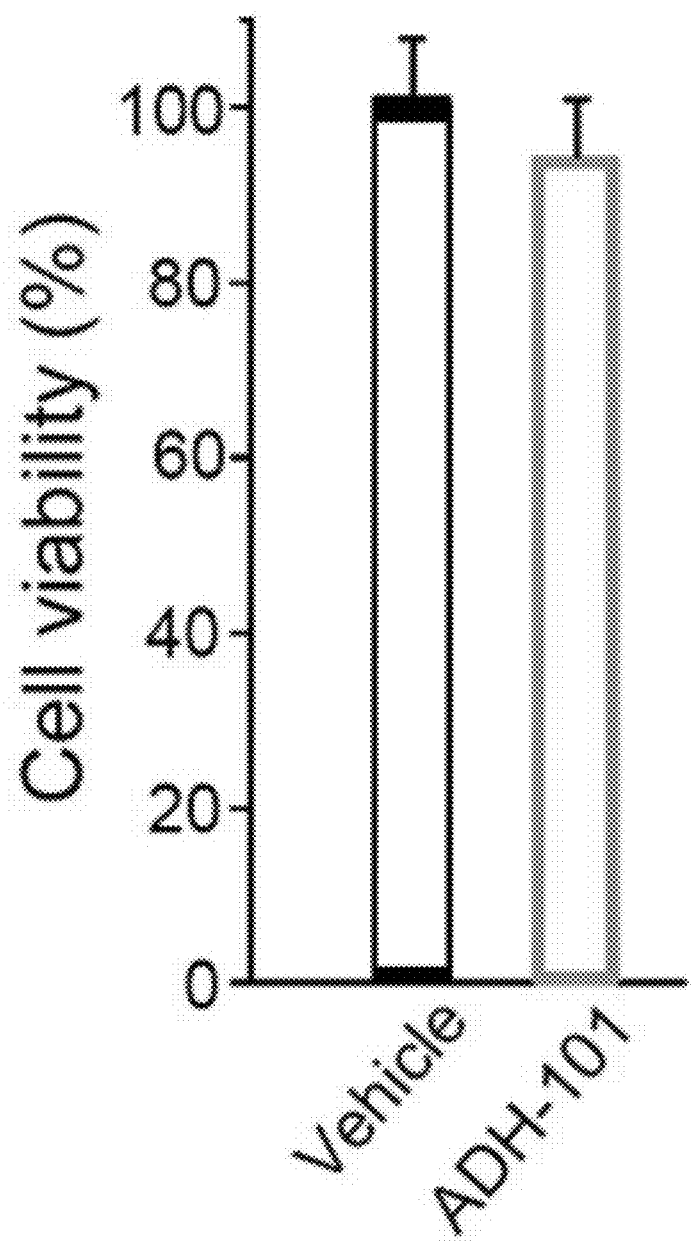
FIG. 15 shows the effect of ADH-101 on the cell viability. Comparison of the effect of IAPP-free solution and ADH-101 on the cell viability of RIN-m cells. The experimental conditions were similar to the cell-viability assay presented in FIG. 6 except that no IAPP was present. Error bars reflect variability across 4-8 technical replicates within a single execution of the assay.
Figure 16:
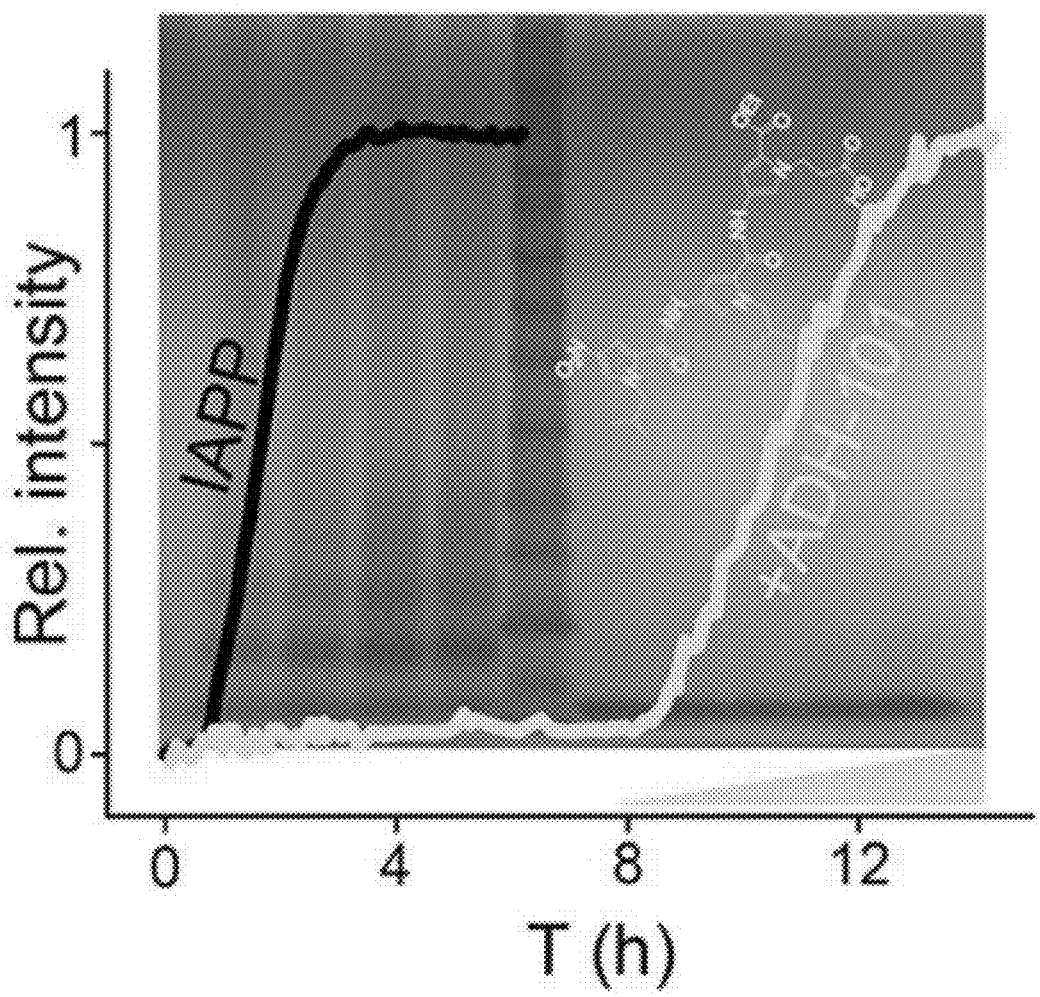
FIG. 16 depicts representative kinetic curves of IAPP aggregation in the absence and presence of ADH-101.
Figure 17:
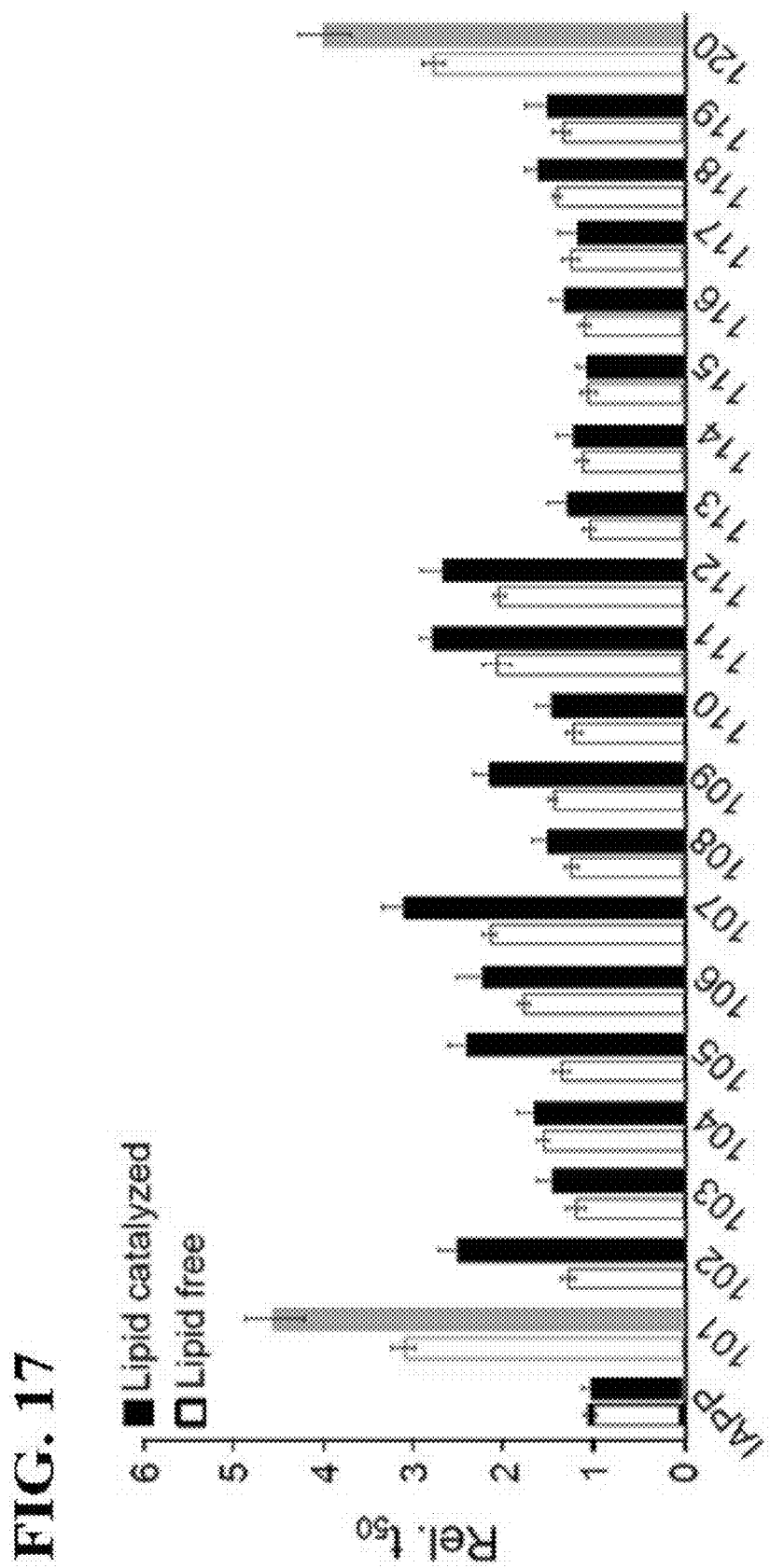
FIG. 17 depicts the antiamyloidogenic effect of select compounds according to the disclosure on the aggregation kinetics of IAPP under lipid free and lipid membrane conditions. The $t_{50}$ for the aggregation kinetics of 15 μM IAPP under lipid free and lipid catalyzed (750 LUVs, DOPG:DOPC, 3:7, d=100 nm) conditions in the absence and presence of the compounds of the disclosure at equimolar ratio.

In the presence of 6 µM IAPP, the cell viability decreased from 100% to ~68% (FIG. 6). The cell viability was normalized by keeping IAPP-free (vehicle) cells as 100%. In marked contrast, the cell viability was completely restored to 100% in the presence of ADH-101 at stoichiometric ratio of 1:1 and 1:2 (IAPP:ADH-101, FIG. 6). ADH-101 was not toxic to the cells under the concentrations used for cell viability assays (FIG. 15).

Clearly, the data form CD, liposome leakage, and cell viability assays suggest that ADH-101 induces a secondary structure in IAPP which is leakage incompetent and has no toxic nature.

Example 11: Specificity Assay

Figure 7B:
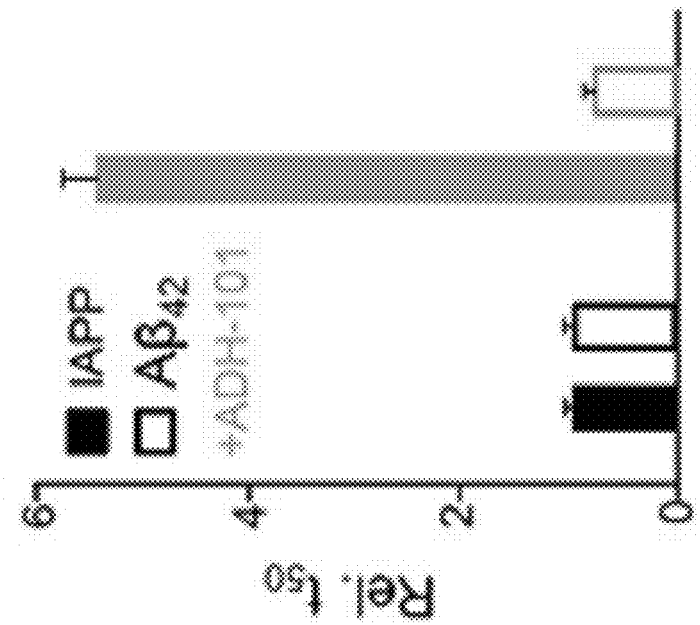
FIGS. 7(A)-7(B) show that the amyloid inhibition by ADH-101 is specific to IAPP.
Figure 7A:
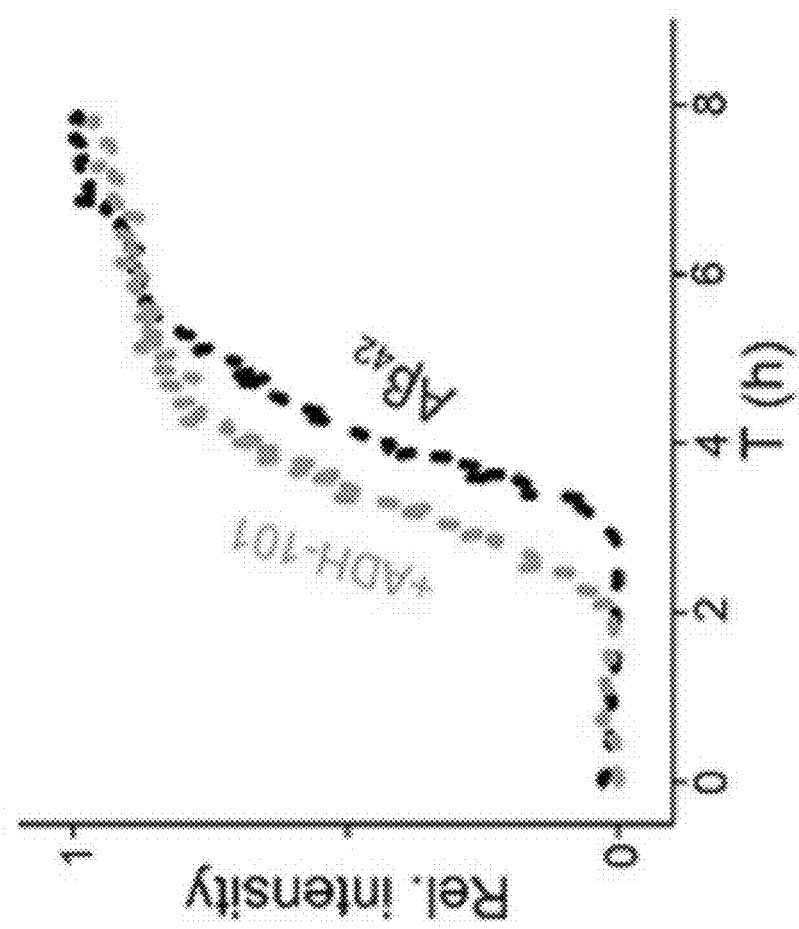

To test the specificity of ADH-101 towards IAPP, the binding interaction of ADH-101 with Aβ peptide was investigated. Aβ is another amyloidogenic peptide whose misfolding is associated with the onset of Alzheimer's disease (Hardy, J.; Selkoe, D. J. *Science* 2002, 297, 353-356; Hardy, J. A.; Higgins, G. A. *Science* 1992, 256, 184-185). IAPP and Aβ share a sequence similarity of ~50% with ~25% identical positioning of the amino acid residues (Yan, L.; Velkova, A.; Tatarek-Nossol, M.; Andreetto, E.; Kapurniotu, A. *Angew. Chem. Int. Ed.* 2007, 46, 1246-1252; Andreetto, E.; Yan, L.; Tatarek-Nossol, M.; Velkova, A.; Frank, R.; Kapurniotu, A. *Angew. Chem. Int. Ed.* 2010, 49, 3081-3085). For instance, Aβ(15-21) and Aβ(26-32) sequences share high degree of sequence similarity and commonality with IAPP(10-16) and IAPP(21-27), respectively. Under identical conditions (to IAPP), the $t_{50}$ for 3 µM Aβ$_{42}$ was 4.22±0.51 h. On the contrary, surprisingly and unexpectedly ADH-101 acts as a weak agonist of Aβ$_{42}$ fibrillation. At equimolar ratio, the $t_{50}$ for the amyloid kinetics of Aβ$_{42}$ in the presence of ADH-101 was 3.41±0.32 h (FIG. 7A). The $t_{50}$ for Aβ$_{42}$ amyloid fiber formation decreased to 0.8 fold in the presence of ADH-101 at an equimolar ratio (FIG. 7B). Clearly, ADH-101 is a conformation specific ligand which with high specificity for IAPP fibrillation inhibition.

Example 12

Figure 12B:
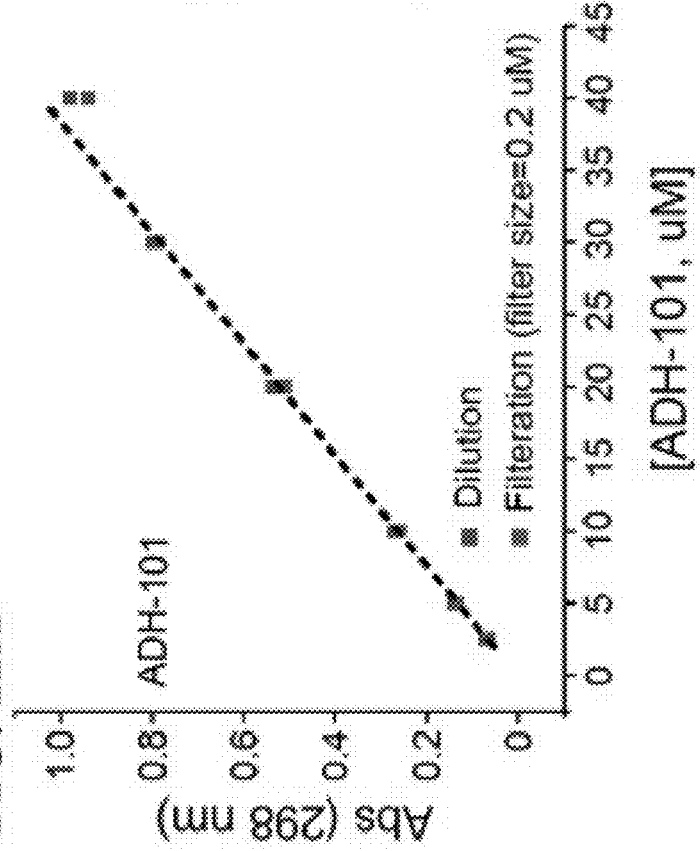
FIGS. 12(A)-12(B) illustrate the analysis of the self-aggregation of ADH-101 using absorbance and DLS.
Figure 12A:
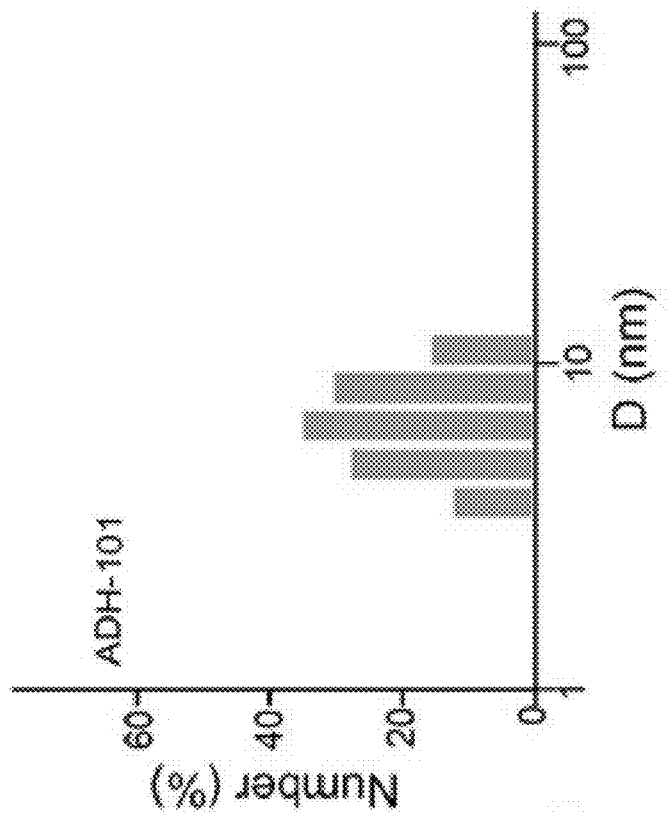

ADH-101 contains hydrophobic and negatively charged groups and presents a possibility for self-aggregation. It has been shown that the small molecules with self-aggregation tendencies can inhibit amyloid formation in a non-specific manner. Therefore, UV, centrifugation, and DLS were used to explore the self-aggregation properties of ADH-101 (FIG. 12A). ADH-101 did not self-assemble up to a concentration of 40 µM, which is about 4 times the concentration used for all the assays. DLS shows the formation of very small species with diameter less than 10 nm 50 µM under phosphate buffer conditions (150 mM KCl, 50 mM NaPi, pH 7.4), arguing against the formation of colloidal aggregates of ADH-101 (FIG. 12B). Therefore, IAPP amyloid inhibition appears to be the result of a specific interaction between IAPP and ADH-101 and does not stem from the self-aggregation of ADH-101.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

All patents, applications, publications, test methods, literature, references, and other materials cited herein are hereby incorporated by reference in their entirety as if physically present in this specification.

REFERENCES

1. Chiti, F.; Dobson, C. M. Annu. Rev. Biochem. 2006, 75, 333-366.
2. Chiti, F.; Dobson, C. M. Nat Chem Biol 2009, 5, 15-22.
3. Jahn, T. R.; Makin, O. S.; Morris, K. L.; Marshall, K. E.; Tian, P.; Sikorski, P.; Serpell, L. C. J. Mol. Biol. 2010, 395, 717-727.
4. Kayed, R.; Head, E.; Thompson, J. L.; McIntire, T. M.; Milton, S. C.; Cotman, C. W.; Glabe, C. G. Science 2003, 300, 486.
5. Westermark, P.; Andersson, A.; Westermark, G. T. Physiol. Rev. 2011, 91, 795.
6. Ashcroft, F.; Rorsman, P. Cell 2012, 148, 1160-1171.
7. Abedini, A.; Schmidt, A. M. FEBS Lett. 2013, 587, 1119-1127.
8. Cao, P.; Abedini, A.; Wang, H.; Tu, L.; Zhang, X.; Schmidt, A. M.; Raleigh, D. P. Proc. Natl. Acad. Sci. U.S.A. 2013, 110, 19279-19284.
9. Knight, J. D.; Hebda, J. A.; Miranker, A. D. Biochemistry 2006, 45, 9496-9508.
10. Magzoub, M.; Miranker, A. D. FASEB J. 2012, 26, 1228-1238.
11. Abedini, A.; Plesner, A.; Cao, P.; Ridgway, Z.; Zhang, J.; Tu, L.; Middleton, C. T.; Chao, B.; Sartori, D. J.; Meng, F.; Wang, H.; Wong, A. G.; Zanni, M. T.; Verchere, C. B.; Raleigh, D. P.; Schmidt, A. M. eLife 2016, 5, e12977.
12. Kumar, S.; Birol, M.; Miranker, A. D. Chem. Commun. 2016, 52, 6391-6394.
13. Kumar, S.; Schlamadinger, D.; Brown, M.; Dunn, J.; Mercado, B.; Hebda, J.; Saraogi, I.; Rhoades, E.; Hamilton, A.; Miranker, A. Chem. Biol. 2015, 22, 369-378.
14. Kulikov, O. V.; Kumar, S.; Magzoub, M.; Knipe, P. C.; Saraogi, I.; Thompson, S.; Miranker, A. D.; Hamilton, A. D. Tetrahedron Lett. 2015, 56, 3670-3673.
15. Hebda, J. A.; Saraogi, I.; Magzoub, M.; Hamilton, A. D.; Miranker, A. D. Chem. Biol. 2009, 16, 943-950.
16. Saraogi, I.; Hebda, J.; Becerril, J.; Estroff, L.; Miranker, A.; Hamilton, A. Angew. Chem. Intl. Ed. 2010, 49, 736-739.
17. Kumar, S.; Miranker, A. D. Chem. Commun. 2013, 49, 4749-4751.
18. Kumar, S.; Brown, M.; Nath, A.; Miranker, A. Chem. Biol. 2014, 21, 775-781.
19. Kumar, S.; Birol, M.; Schlamadinger, D. E.; Wojcik, S. P.; Rhoades, E.; Miranker, A. D. Nat Commun 2016, 7, 1-11.
20. Peacock, H.; Luo, J.; Yamashita, T.; Luccarelli, J.; Thompson, S.; Hamilton, A. D. Chem. Sci., 2016, 7, 6435-6439.
21. Pithadia A., Brender J. R., Fierke C. A., and Ramamoorthy A. J Diabetes Res. 2016, 1-12.
22. Meng, F.; Abedini, A.; Plesner, A.; Middleton, C. T., Potter, K. J.; Zanni, M. T.; Verchere, C. B.; Raleigh, D. P. J. Mol. Biol. 2010, 400, 555-566.
23. Yan, L.; Tatarek-Nossol, M.; Velkova, A.; Kazantzis, A.; Kapurniotu, A. Proc. Natl. Acad. Sci. U.S.A. 2006, 103, 2046-2051.
24. Wade, W. S.; Mrksich, M.; Dervan, P. B. J. Am. Chem. Soc. 1992, 114, 8783-8794.
25. Chenoweth, D. M.; Meier, J. L.; Dervan, P. B. Angew. Chem. Intl. Ed. 2013, 52, 415-418.
26. Dervan, P. B.; Baird, E. United states patent 2000. US006090947A.
27. Uytterhoeven, K.; Sponer, J.; Van Meervelt, L. Eur. J. Biochem. 2002, 269, 2868-2877.
28. Wolfe, L. S.; Calabrese, M. F.; Nath, A.; Blaho, D. V.; Miranker, A. D.; Xiong, Y. Proc. Natl. Acad. Sci. U.S.A. 2010, 107, 16863-16868.
29. Levine, H. Protein Sci. 1993, 2, 404-410.
30. Rustenbeck, I.; Matthies, A.; Lenzen S. Lipids 1994, 10, 685-92.
31. Cao, P.; Raleigh, D. P. Biochemistry, 2012, 51, 2670-2683.
32. Meng, F.; Abedini, A.; Plesner, A.; Verchere, C. B.; Raleigh, D. P. Biochemistry, 2010, 49, 8127-8133.
33. Daval, M.; Bedrood, S.; Gurlo, T.; Huang, C.-J.; Costes, S.; Butler, P. C.; Langen, R. Amyloid, 2010, 17, 118-128.
34. Meng, F.; Abedini, A.; Plesner, A.; Middleton, C. T.; Potter, K. J.; Zanni, M. T.; Verchere, C. B.; Raleigh, D. P. J. Mol. Biol. 2010, 400, 555-566.
35. Hao, M.; Lin, S. X.; Karylowski, O. J.; Wüstner, D.; McGraw, T. E.; Maxfield, F. R. J. Biol. Chem. 2002, 277, 609-617.
36. Warnock, D. E.; Roberts, C.; Lutz, M. S.; Blackburn, W. A.; Young Jr., W. W.; Baenziger, J. U. J. Biol. Chem. 1993, 268, 10145-10153.
37. Sciacca, M. F. M.; Lolicato, F. Mauro, G. D.; Milardi, D.; D'Urso, L.; Satriano, C.; Ramamoorthy, A.; Rosa C. L. Biophy. J. 2016, 111, 140-151.
38. Ono, K.; Condron, M. M.; Teplow, D. B. Proc. Natl. Acad. Sci. U.S.A. 2009, 106, 14745-14750.
39. Feng, B. Y.; Toyama, B. H.; Wille, H.; Colby, D. W.; Collins, S. R.; May, B. C. H.; Prusiner, S. B.; Weissman, J.; Shoichet, B. K. Nature Chem Biol 2008, 4, 197-199.

40. Pilch, D. S.; Poklar, N.; Gelfand, C. A.; Law, S. M.; Breslauer, K. J.; Baird, E. E.; Dervan, P. B. Proc. Natl. Acad. Sci. U.S.A. 1996, 93, 8306-8311.
41. Last, N. B.; Miranker, A. D. Proc. Natl. Acad. Sci. U.S.A. 2013, 110, 6382-6387.
42. Last, N. B.; Rhoades, E.; Miranker, A. D. Proc. Natl. Acad. Sci. U.S.A. 2011, 108, 9460-9465.
43. Sparks, S.; Liu, G.; Robbins, K. J.; Lazo, N. D. Biochem. Biophys. Res. Comm., 2012, 422, 551-555.
44. Huang, C.; Lin, C.; Haataja, L., Gurlo, T., Butler, A. E., Rizza, R. A., and Butler, P. C. Diabetes, 2007, 56, 2016-2027.
45. Hardy, J.; Selkoe, D. J. Science 2002, 297, 353-356.
46. Hardy, J. A.; Higgins, G. A. Science 1992, 256, 184-185.
47. Yan, L.; Velkova, A.; Tatarek-Nossol, M.; Andreetto, E.; Kapurniotu, A. Angew. Chem. Int. Ed. 2007, 46, 1246-1252.
48. Andreetto, E.; Yan, L.; Tatarek-Nossol, M.; Velkova, A.; Frank, R.; Kapurniotu, A. Angew. Chem. Int. Ed. 2010, 49, 3081-3085.
49. Chen, P. S.; Toribara, T. Y.; Warner, H. Anal. Chem. 1956, 28, 1756-1758.

What is claimed is:
1. A compound according to formula (IV):

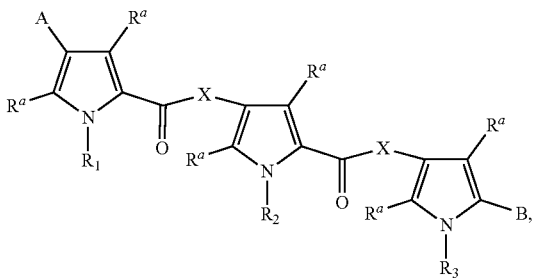

wherein $R^a$ is independently selected at each occurrence from hydrogen, $C_1$-$C_{12}$ hydrocarbons, —F; —Cl; —Br; —I; —OH, —OR*; —SO$_3$H; —NO; —NO$_2$; —NO$_3$; —O—NO; —N$_3$; —NH$_2$; —NHR*; and —N(R*)$_2$;

X is independently at each occurrence selected from —O—; —S—; —NH—; —NR*—; and C(R*)$_2$;

$R_1$ is selected from hydrogen or a straight chained $C_2$-$C_{20}$ hydrocarbon, or branched or cyclic aliphatic $C_3$-$C_{20}$ hydrocarbon; an aromatic $C_6$-$C_{20}$ hydrocarbon; a heteroaromatic $C_2$-$C_{20}$ hydrocarbon; and a $C_2$-$C_{12}$ perfluorocarbon, or a combination thereof, each of which is optionally substituted with one or more of —F; —Cl; —Br; —I; —OH, —NO; —NO$_2$; —NO$_3$; —O—NO; —N$_3$; —NH$_2$; —NHR*; —N(R*)$_2$; —N(R*)$_3$$^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_3$H; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; and —P(=O)(OR*)$_2$; or combinations thereof;

$R_2$ is independently at each occurrence selected from hydrogen or a straight chained $C_2$-$C_{20}$ hydrocarbon, or branched or cyclic aliphatic $C_3$-$C_{20}$ hydrocarbon; an aromatic $C_6$-$C_{20}$ hydrocarbon; a heteroaromatic $C_2$-$C_{20}$ hydrocarbon; and a $C_2$-$C_{12}$ perfluorocarbon, or a combination thereof, each of which is optionally substituted with one or more of —F; —Cl; —Br; —I; —OH, —NO; —NO$_2$; —NO$_3$; —O—NO; —N$_3$; —NH$_2$; —NHR*; —N(R*)$_2$; —N(R*)$_3$$^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_3$H; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; and —P(=O)(OR*)$_2$; or combinations thereof;

$R_3$ is selected from hydrogen or a straight chained $C_2$-$C_{20}$ hydrocarbon, or branched or cyclic aliphatic $C_3$-$C_{20}$ hydrocarbon; an aromatic $C_6$-$C_{20}$ hydrocarbon; a heteroaromatic $C_2$-$C_{20}$ hydrocarbon; and a $C_2$-$C_{12}$ perfluorocarbon, or a combination thereof, each of which is optionally substituted with one or more of —F; —Cl; —Br; —I; —OH, —NO; —NO$_2$; —NO$_3$; —O—NO; —N$_3$; —NH$_2$; —NHR*; —N(R*)$_2$; —N(R*)$_3$$^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_3$H; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; and —P(=O)(OR*)$_2$; or combinations thereof;

wherein at least one of $R_1$, $R_2$, and $R_3$ is substituted with one or more of —F; —Cl; —Br; —I; —OH, —NO; —NO$_2$; —NO$_3$; —O—NO; —N$_3$; —NH$_2$; —NHR*; —N(R*)$_2$; —N(R*)$_3$$^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$;

—(C=S)—NH₂; —(C=S)—N(R*)₂, —N(R*)—CHO; —N(R*)—(C=O)—R*; —SCN; —NCS; —NSO; —SSR*; —SO₂R*; —SO₃H; —SO₂—N(R*)₂; —S(=O)—OR*; —S(=O)—R*; —Si(R*)₃; —CF₃; —O—CF₃; —P(R*)₂; —O—P(=O)(OR*)₂; and —P(=O)(OR*)₂; or combinations thereof;

A is selected from —OH, —OR*; —NO; —NO₂; —NO₃; —O—NO; —N₃; —CN; —NC; —(C=O)—R*; —CHO; —CO₂H; —CO₂R*; —(C=O)—S—R*; —O—(C=O)—H; —O—(C=O)—R*; —S—(C=O)—R*; —(C=O)—NH₂; —(C=O)—N(R*)₂; —(C=O)—NHNH₂; —O—(C=O)—NHNH₂; —(C=S)—NH₂; —(C=S)—N(R*)₂; —SCN; —NCS; —NSO; —SSR*; —SO₂R*; —SO₃H; —SO₂—N(R*)₂; —S(=O)—OR*; —S(=O)—R*; —Si(R*)₃; —CF₃; —O—CF₃; —P(R*)₂; —O—P(=O)(OR*)₂; —P(=O)(OR*)₂; $C_1$-$C_8$ perfluorocarbon; an aliphatic $C_1$-$C_{12}$ hydrocarbon; an aromatic $C_3$-$C_{12}$ hydrocarbon; and a $C_2$-$C_{12}$ heteroaryl, with a proviso that A is not —N(R*)—(C=O)—H or —N(R*)—(C=O)—CH₃;

B is selected from hydrogen, —F; —Cl; —Br; —I; —OH, —OR*; —NO; —NO₂; —NO₃; —O—NO; —N₃; —NH₂; —NHR*; —N(R*)₂; —N(R*)₃⁺; —N(R*)—OH; —O—N(R*)₂; —N(R*)—O—R*; —CN; —NC; —(C=O)—R*; —CHO; —CO₂H; —CO₂R*; —(C=O)—S—R*; —O—(C=O)—H; —O—(C=O)—R*; —S—(C=O)—R*; —(C=O)—NH₂; —O—(C=O)—NHNH₂; —(C=S)—NH₂; —(C=S)—N(R*)₂; —N(R*)—CHO; —N(R*)—(C=O)—R*; —SCN; —NCS; —NSO; —SSR*; —SO₂R*; —SO₃H; —SO₂—N(R*)₂; —S(=O)—OR*; —S(=O)—R*; —Si(R*)₃; —CF₃; —O—CF₃; —P(R*)₂; —O—P(=O)(OR*)₂; —P(=O)(OR*)₂; $C_1$-$C_8$ perfluorocarbon; an aliphatic $C_1$-$C_{12}$ hydrocarbon; an aromatic $C_3$-$C_{12}$ hydrocarbon; and a $C_2$-$C_{12}$ heteroaryl;

R* is independently selected at each occurrence from hydrogen or $C_1$-$C_{12}$ hydrocarbons each of which optionally contains 1-8 heteroatoms selected from halogen, O, N, and S; or combinations thereof, or a pharmaceutically acceptable salt thereof.

2. The compound of claim 1 according to formula (V):

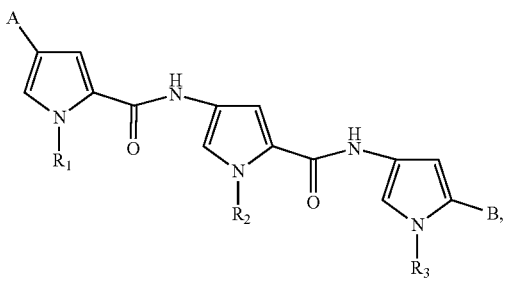

(V)

or a pharmaceutically acceptable salt thereof.

3. A compound having the structure of formula:

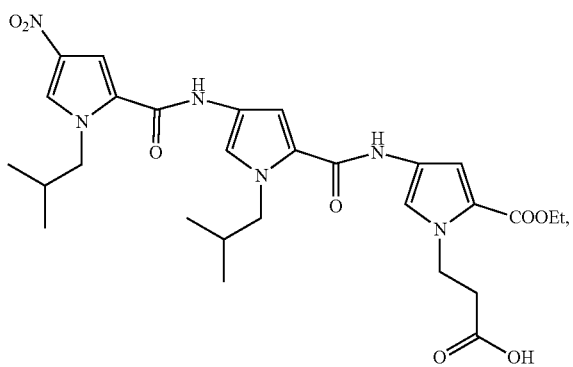

(ADH-101)

or a pharmaceutically acceptable salt thereof.

4. A compound having the structure of formula:

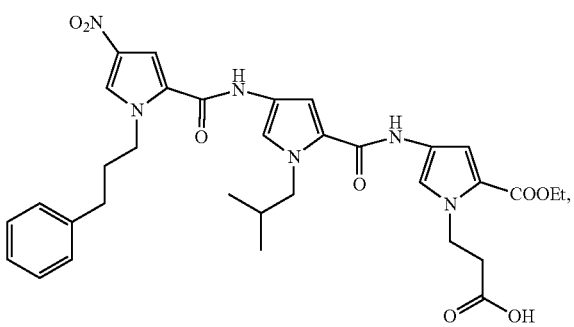

(ADH-120)

or a pharmaceutically acceptable salt thereof.

5. A pharmaceutical composition comprising the compound of claim 1 and a pharmaceutically acceptable carrier or excipient.

6. A pharmaceutical dosage form comprising the compound of claim 1.

7. A method of altering the structure of islet amyloid polypeptide (IAPP) comprising contacting said IAPP with an effective amount of the compound of claim 1.

8. A method of inhibiting oligomerization of islet amyloid polypeptide (IAPP) comprising contacting said IAPP with an effective of the compound of claim 1.

9. A method of inhibiting cytotoxicity of islet amyloid polypeptide (IAPP) in a subject in need thereof comprising administering to said subject an effective amount of the compound of claim 1.

10. A method of treating a disease in a subject in need of such treatment comprising administering to said subject an effective amount of the compound of claim 1, wherein said disease is selected from the group consisting of insulinoma, diabetes mellitus, hyperglycemia, islet rejection following pancreatic islet transplantation, Alzheimer's Disease, Mild Cognitive Impairment (MCI), Lewy body dementia, cerebral amyloid angiopathy, and Parkinson's Disease.

11. A method of treating diabetes mellitus in a subject in need of such treatment comprising administering to said subject an effective amount of the compound of claim 1, wherein said compound inhibits oligomerization of islet amyloid polypeptide (IAPP).

12. The method of claim 7, wherein the compound of Formula (IV) is selected from the group consisting of

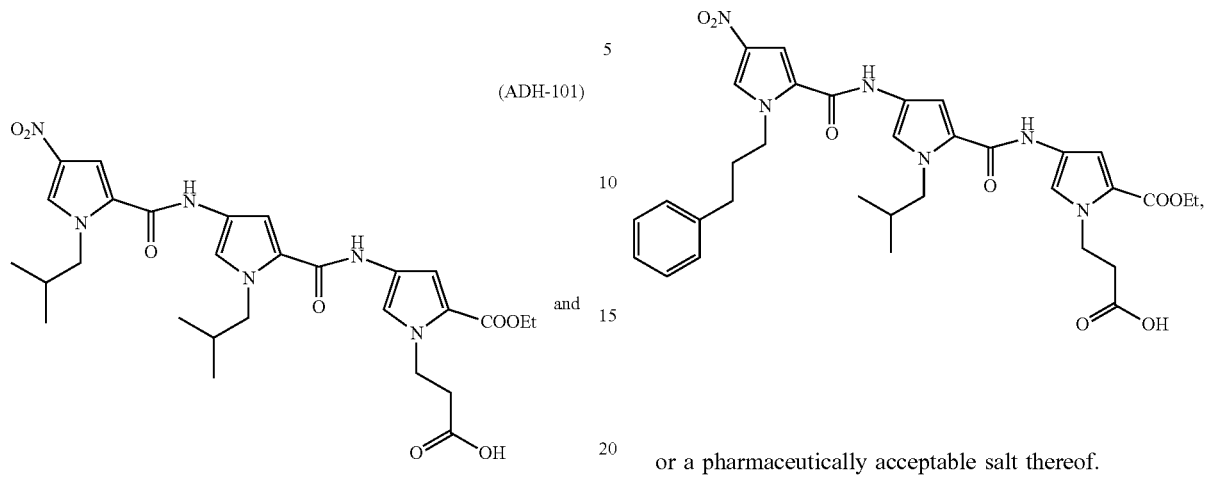

or a pharmaceutically acceptable salt thereof.

13. The method of claim 8, wherein the compound of Formula (IV) is selected from the group consisting of

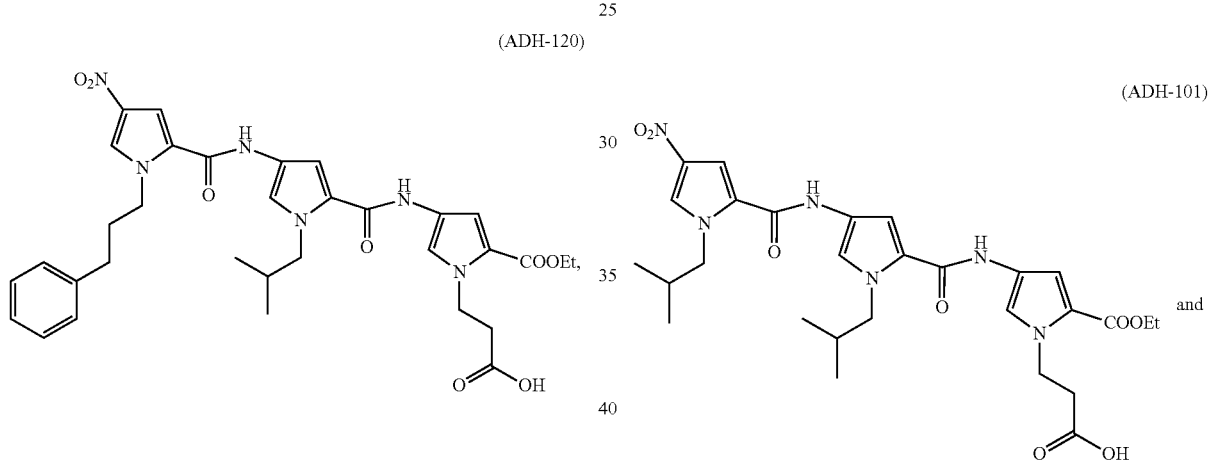

or a pharmaceutically acceptable salt thereof.

14. The method of claim 9, wherein the compound of Formula (IV) is selected from the group consisting of

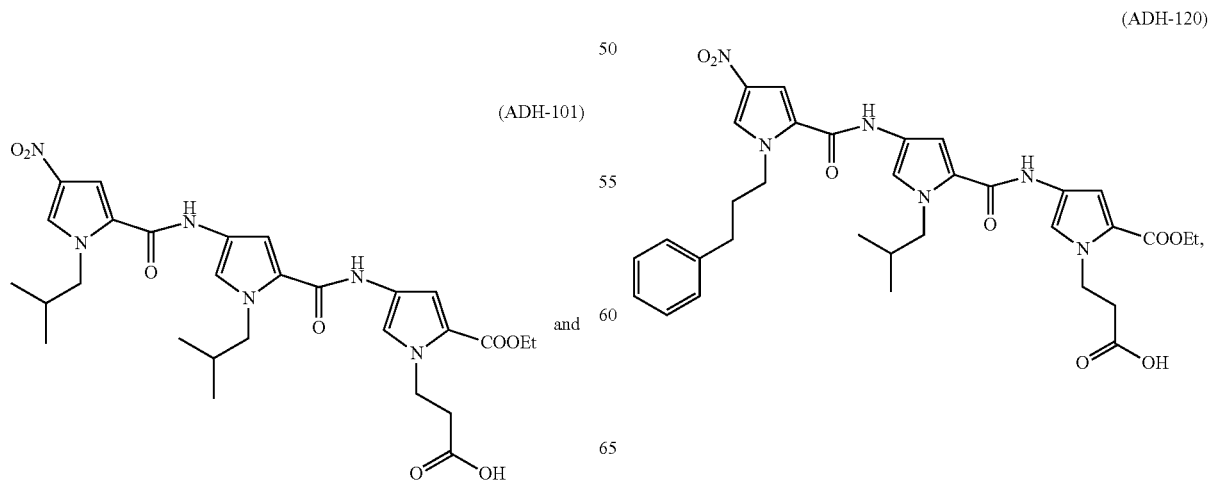

or a pharmaceutically acceptable salt thereof.

15. The method of claim 10, wherein the compound of Formula (IV) is selected from the group consisting of
16. The method of claim 11, wherein the compound of Formula (IV) is selected from the group consisting of
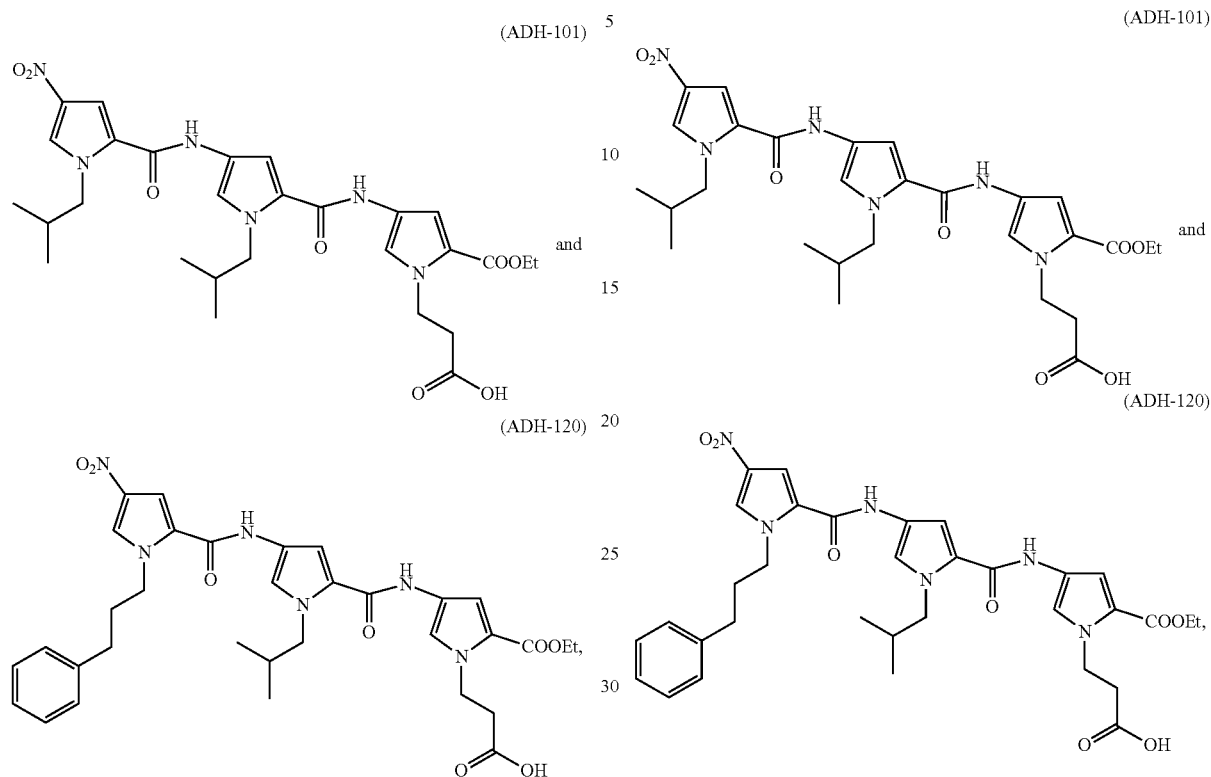
or a pharmaceutically acceptable salt thereof.
or a pharmaceutically acceptable salt thereof.
* * * * *